United States Patent [19]

Morimoto et al.

[11] Patent Number: 4,876,251

[45] Date of Patent: Oct. 24, 1989

[54] TRICYCLIC PENAM COMPOUNDS, THEIR PRODUCTION AND THEIR USE

[75] Inventors: Akira Morimoto; Nobuo Choh; Noriyoshi Noguchi, all of Osaka, Japan

[73] Assignee: Takeda Chemical Industries, Ltd., Japan

[21] Appl. No.: 59,951

[22] Filed: Jun. 9, 1987

[30] Foreign Application Priority Data

Jun. 17, 1986 [JP] Japan ................................. 61-142257

[51] Int. Cl.$^4$ .................... A61K 31/43; C07D 205/12; C07D 499/82
[52] U.S. Cl. ................................. 514/193; 540/200; 540/203; 540/305
[58] Field of Search ....................... 540/305, 200, 203; 514/193

[56] References Cited

U.S. PATENT DOCUMENTS

| | | | |
|---|---|---|---|
| 3,947,439 | 3/1976 | Wei et al. | 540/203 |
| 4,148,995 | 4/1979 | Petrzika et al. | 514/193 |
| 4,490,382 | 12/1984 | Jung et al. | 540/312 X |
| 4,508,723 | 4/1985 | Schaffner et al. | 540/312 X |

OTHER PUBLICATIONS

Chemical Abstracts, vol. 85, No. 25, Dec. 20, 1976, p. 555, abstract No. 192709n.
Chemical Abstracts, vol. 85, No. 5, Aug. 2, 1976, p. 399, abstract No. 32995z.
Chemical Abstracts, vol. 85, No. 25, Dec. 20, 1976, p. 555, abstract No. 192716n.

*Primary Examiner*—Werren B. Lone
*Assistant Examiner*—Vera C. Clarke
*Attorney, Agent, or Firm*—Wegner & Bretschneider

[57] ABSTRACT

The compounds, having a 4,10-dioxo-3-oxa-7-thia-1-azatricyclo[6,2,0,0$^{2,6}$]decane-2-carboxylic acid skeleton as the base structure, their esters and their salts, are useful antibacterial agents.

19 Claims, No Drawings

TRICYCLIC PENAM COMPOUNDS, THEIR PRODUCTION AND THEIR USE

The present invention relates to compounds having a 4,10-dioxo-3-oxa-7-thia-1-azatricyclo[6,2,0,0$^{2,6}$]decane-2-carboxylic acid skeleton and possessing antibacterial activities, their esters, their salts, the method of their production, its intermediates and use.

The novel antibiotic TAN-588 (hereinafter also referred to as "TAN-588"), which exhibits antibacterial activities on both gram-positive bacteria and gram-negative bacteria, has recently been obtained from new bacterial species belonging to the genera Empedobacter and Lysobacter as isolated from soil. In addition, its derivatives have been synthesized, which are disclosed in, for example, Japanese Patent Application No. 280139/1985.

The said antibiotic TAN-588 has a peculiar skeleton consisting of a 3-oxoisoxazolidine ring having 5-oxo-2-tetrahydrofurancarboxylic acid bonded to its nitrogen atom, which has been hitherto unknown.

On the other hand, penicillin still occupies an important position as an antibiotic; various investigations have been made of the substituents at the 2 and 6 positions of the penicillin skeleton and their configuration.

The purpose of the present invention is to provide a compound which has quite a novel base skeleton wherein a 5-oxotetrahydrofuran ring, a partial structure of TAN-588, is introduced into a penicillin skeleton, resulting in a totally novel and unique base skeleton which is far from not only the TAN-588 structure and the penicillin skeleton but also any of the other known tricyclic compounds, and which exhibits antibacterial activities.

The present inventors made investigations of various compounds having the TAN-588 skeleton or its partial structure, finding that tricyclic penam compounds having a penicillin skeleton into which the 5-oxo-tetrahydrofuran ring of TAN-588 is introduced can be chemically produced, and that such chemically produced compounds possess excellent antibacterial activities; the present inventors thus completed the present invention.

The present invention relates to:

(1) a compound having a 4,10-dioxo-3-oxa-7-thia-1-azatricyclo[6,2,0,0$^{2,6}$]decane-2-carboxylic acid skeleton, its ester or its salt, (2) a compound having a skeleton as defined in (1) having an amino group or organic residue bonded via nitrogen or carbon as a substituent specifically at the 9 position, (3) a compound represented by the formula:

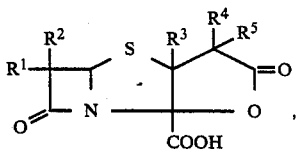

(I)

wherein R$^1$ represents hydrogen, an amino group or an organic residue bonded via nitrogen or carbon; R$^2$ represents hydrogen, a methoxy group or a formylamino group; R$^3$, R$^4$ and R$^5$ independently represent hydrogen or an organic residue, its esters or its salts.

(4) a method for producing a compound having a 4,10-dioxo-3-oxa-7-thia-1-azatricyclo[6,2,0,0$^{2,6}$]decane-2-carboxylic acid skeleton, its ester or its salt, characterized by the cyclization of a compound having a 2-oxo-3-(2-azetidinon-4-yl)thioglutaric acid skeleton, its ester, or a compound having a 3-(2-azetidinon-4-yl)thio-5-oxotetrahydrofuran-2-carboxylic acid skeleton having a leaving group at the 2nd position or its ester, (5) a compound having a 2-oxo-3-(2-azetidinon-4-yl)thioglutaric acid skeleton, its ester or its salt, (6) a compound having a 3-(2-azetidinon-4-yl)thio-5-oxo-tetrahydrofuran-2-carboxylic acid skeleton having a leaving group at the 2 position, its ester or its salt, and (7) an antibacterial composition containing a compound having a 4,10-dioxo-3-oxa-7-thia-1-azatricyclo[6,2,0,0$^{2,6}$]decane-2-carboxylic acid skeleton, its ester or its salt.

Of the compounds of the present invention, which have a novel 4,10-dioxo-2-oxa-7-thia-1-azatricyclo[6,2,0,0$^{2,6}$]decane-2-carboxylic acid skeleton consisting of a penam skeleton to which a 5-oxotetrahydrofurancarboxylic acid ring is introduced, preferred are a compound represented by the general formula:

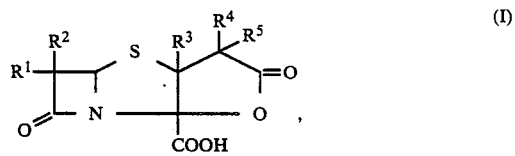

(I)

wherein, R$^1$ represents hydrogen, an amino group or an organic residue bonded via nitrogen or carbon; R$^2$ represents hydrogen, a methoxy group or a formylamino group; R$^3$, R$^4$ and R$^5$ independently represent either hydrogen or an organic residue, its ester or its salt.

As examples of organic residues bonded via nitrogen represented by R$^1$ in the above-shown general formula, mention may be made of amino groups substituted via carbon such as acylamino, alkenylamino, ureido, thioureido groups and groups having the group represented by the formula —CO—CO—NH—; thioamino; silylamino and phosphoamino groups.

As examples of acyl groups for the above acylamino groups, mention may be made of the conventionally known acyl groups such as acyl groups which are used as the substituent of the amino group at the 6-position of penicillin derivatives and the amino group at the 7-position of cephalosporin derivatives.

As examples of said acylamino groups, mention may be made of groups represented by the formula:

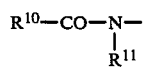

wherein R$^{10}$ represents hydrogen, alkyl* (In the description of respective groups in the present specification, groups marked with asterisk* may have a substituent.), alkenyl*, cycloalkyl*, aryl*, heterocyclic ring*, alkoxy*, or aryloxy*; R$^{11}$ represents either hydrogen or alkyl*; R$^{10}$ may be combined with R$^{11}$ to form a ring, groups represented by the formula:

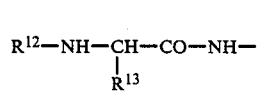

wherein R$^{12}$ represents hydrogen, an amino acid residue*, an amino-protecting group or a group represented by the formula $R^{14}$—$(CH_2)n$-$C(=Z)$—wherein $R^{14}$ represents heterocyclic ring*, alkoxy* or amino*; n represents 0, 1 or 2; and represents O or S; and $R^{13}$ represents alkyl*, aryl*, cycloalkenyl* or heterocyclic ring*, groups represented by the formula:

$$R^{15}—R^{16}—CO—NH—$$

wherein, $R^{15}$ represents a group represented by the formula

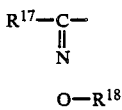

wherein $R^{17}$ represents alkyl*, heterocyclic ring* or aryl* and $R^{18}$ represents hydrogen, alkyl*, alkenyl*, cycloalkyl*, heterocyclic ring* or a group represented by the formula —$R^{19}$—$R^{20}$ wherein $R^{19}$ represents alkylene*, cycloalkylene* or alkenylene and $R^{20}$ represents aryl*, carboxyl, its esters or mono- or dialkylamide.; and $R^{16}$ represents a bonding hand or a group represented by the formula —CO—NH—

$$\begin{array}{c} CH—\\ |\\ R^{21} \end{array}$$

wherein $R^{21}$ represents alkyl*, aryl* or heterocyclic ring*, groups represented by the formula:

$$R^{22}—CH—CO—NH—\\ \hspace{1.5cm}|\\ \hspace{1.5cm}R^{23}$$

wherein $R^{22}$ represents aryl*, heterocyclic ring* or cycloalkenyl* and $R^{23}$ represents hydroxy, sulfamoyl, sulfo, sulfoxy or acyloxy*, or groups represented by the formula:

$$R^{24}—R^{25}—CH_2—CO—NH—$$

wherein $R^{24}$ and represents alkyl*, cyano, aryl* aryloxy*, alkenyl*, heterocyclic ring*, amino* or a group represented by the formula $R^{24}$, —C(=S) —wherein $R^{24}$, represents alkoxy. and $R^{25}$ represents a bonding hand or —S—. As examples of said ureido or thioureido, mention may be made of groups represented by the formula:

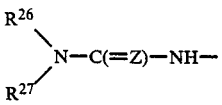

wherein $R^{26}$ and $R^{27}$ independently represent hydrogen, alkyl*, aryl*, heterocyclic ring* or cycloalkyl, and Z represents O or S.

The formula

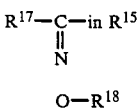

represents a syn isomer represented by the formula

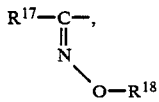

an anti isomer represented by the formula

or their mixture.

As examples of amino groups substituted via carbon exemplifying organic residues bonded via nitrogen represented by the above $R^1$, mention may be made of groups represented by the formula:

$$R^{28}—NH—$$

wherein $R^{28}$ represents alkyl*, aryl*, alkenyl* or heterocyclic ring*, groups represented by the formula:

wherein $R^{29}$ and $R^{30}$ each represent alkyl*, aryl* or alkenyl*, whether or not they are the same, $R^{29}$ and $R^{30}$ may be combined with each other, together with the adjacent nitrogen atom, to form a heterocyclic ring, and groups represented by the formula:

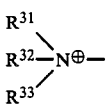

wherein $R^{31}$, $R^{32}$ and $R^{33}$ each represent alkyl*, aryl* or alkenyl*, whether identical or not; $R^{31}$ and either $R^{32}$ or $R^{33}$ may be combined with each other, together with the adjacent nitrogen atom, to form a heterocyclic ring.

As examples of alkenylamino groups exemplifying the organic residue bonded via nitrogen represented by the above $R^1$, mention may be made of groups represented by the formula:

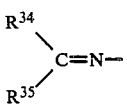

wherein $R^{34}$ and $R^{35}$ each represent hydrogen, alkyl*, aryl*, cycloalkyl, amino*, or heterocyclic ring*, whether identical or not; $R^{34}$ and $R^{35}$ may be combined with each other, together with the adjacent carbon atom, to form either cycloalkyl* or a heterocyclic ring*.

As examples of thioamino groups exemplifying the organic residue bonded via nitrogen represented by the above $R^1$, mention may be made of groups represented by the formula:

$$R^{36}-SO_n-NH-$$

wherein $R^{36}$ represents alkyl* or aryl* and n represents 0, 1 or 2.

As examples of silylamino groups exemplifying the organic residue bonded via nitrogen represented by the above $R^1$, mention may be made of groups represented by the formula:

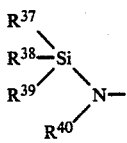

wherein $R^{37}$, $R^{38}$ and $R^{39}$ each represent alkyl* or aryl*, whether identical or not; they may together form a cyclic group; $R^{40}$ represents hydrogen of silyl*.

As examples of phosphoamino groups exemplifying the organic residue bonded via nitrogen represented by the above $R^1$, mention may be made of groups represented by the formula:

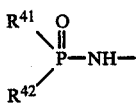

wherein $R^{41}$ and $R^{42}$ each represent alkyl*, aryl*, alkoxy*, or aryloxy*, whether identical or not; $R^{41}$ and $R^{42}$ may together form a heterocyclic ring*.

As examples of groups containing the group represented by the formula —CO—NH— exemplifying the organic residue bonded via nitrogen represented by the above $R^1$, mention may be made of groups represented by the formula:

$$R^{43}-CO-CO-NH-$$

wherein $R^{43}$ represents hydrogen, alkyl*, alkoxy*, aryl*, aryloxy*, heterocyclic ring* or amino*.

In the above formulae, organic residues bonded via carbon represented by $R^1$ include, for example, alkyl*, cycloalkyl*, alkenyl*, aryl*, acyl, cyano, carbamoyl, carboxyl which may be esterified or amidated and heterocyclic rings*.

In the above formulae, organic residues bonded via nitrogen or carbon represented by $R^1$ preferably have a molecular weight of, for example, up to 500.

Alkyls in groups represented by $R^1$ in the above formulae preferably have, for example, 1 to 6 carbon atoms in straight or branched chain. As examples of such alkyls, mention may be made of methyl, ethyl, n-propyl, isopropyl, n-butyl, isobutyl, sec-butyl, t-butyl, 1,1-dimethylpropyl, n-pentyl, isopentyl, n-hexyl and isohexyl.

Substituents which the said alkyl groups may have include halogen, oxo, thioxo, nitro, amino (which may have alkyl, alkenyl, cycloalkyl, aryl, acyl, carbamoyl or N-sulfocarbamoyl as a substituent), sulfo, cyano, hydroxy, carboxy (which may be esterified with alkyl), cycloalkyl, cycloalkenyl, alkoxy (which may have amino, hydroxy, carboxy, halogen, aryl, cycloalkyl or alkoxy as a substituent), aryl (which may have halogen, alkyl, alkoxy, alkylamino, amino, carbamoyl, sulfo, alkylsulfonyl, cyano, hydroxy, carboxy, nitro, acyloxy, aralkyloxy or sulfoxy as a substituent), arylcarbonyl which may have a substituent such as that mentioned above for aryl, aryloxy which may have a substituent such as that mentioned above for aryl, heterocyclic rings (which may have nitro, oxo, aryl, alkenylene, halogenoalkyl, alkylsulfonyl, alkyl, alkoxy, alkylamino, amino, halogen, carbamoyl, hydroxy, cyano, carboxy or sulfo as a substituent), acyl (which may have as a substituent arylcarbonylhydrazino which may have hydroxy, halogen, amino or nitro as a substituent), acyloxy, alkoxycarbonyl, alkoxycarbonyloxy (which may be substituted by halogen), acyloxy-ethoxy, aralkyl (which may have alkyl, alkoxy, halogen, amino, hydroxy, nitro, cyano, carbamoyl or sulfamoyl as a substituent), aralkyloxy (which may have acyloxy, alkyl, alkoxy, halogen, amino, hydroxy, nitro, cyano, carbamoyl or sulfamoyl as a substituent), hydroxysulfonyloxy, alkylsulfonyloxy, arylsulfonyloxy, alkylsulfonyl, aminosulfonyl, alkylsulfinyl, alkylthio (which may have cyano, halogen, carboxy, alkylamino, imino, carbamoyl or acylamino as a substituent), arylthio, heterocyclic ring-thio (which may have cyano, hydroxy, amino, alkylamino, alkyl, halogen or oxo as a substituent), heterocyclic rings (which may have cyano, hydroxy, amino, alkylamino, alkyl, halogen or oxo as a substituent)alkylthio, iminomethylamino, iminomethylamino, silyl (which may have alkyl or aryl as a substituent), silyloxy which may have a substituent similar to that mentioned above for silyl, phthalimido, succinimido, dialkylamino, dialkylaminocarbonyl, arylcarbonylamino, carbamoyl, carbamoyloxy, N-sulfocarbamoyloxy, alkylcarbonylcarbamoyloxy (which may be substituted by halogen), alkoxyimino and groups represented by the formula:

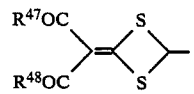

wherein $R^{47}$ and $R^{48}$ each represent a hydroxyl or amino group, whether identical or not.

In the above formulae, alkylenes represented by $R^{19}$ preferably have 1 to 6 carbon atoms. As examples of such alkylenes, mention may be made of methylene, ethylene, trimethylene, tetramethylene, pentamethylene and hexamethylene.

Substituents which the said alkylene groups may have include halogen, amino, hydroxy, alkoxy, carboxy, carbamoyl, cyano and nitro.

In the above formulae, cycloalkyls, cyclocalkyls in cycloalkyloxy and cycloalkyls formed by two or more groups being combined in groups represented by $R^1$, preferably have 3 to 8 carbon atoms. As examples of such cycloalkyls, mention may be made of cyclopropyl, cyclobutyl, cyclopentyl, cyclohexyl, cycloheptyl and cyclooctyl.

Substituents which the said cycloalkyl groups may have include halogen, nitro, amino, hydroxy, sulfo, cyano, carboxyl, oxo and thioxo.

Cycloalkylenes in groups in the above formulae include those consisting of the above cycloalkyl having another bonding hand such as cyclopropylene, cyclohexylene, etc.

Aryls for aryl, arylcarbonyl, aryloxycarbonyl, aryloxy or arylthio in groups represented by $R^1$ in the above formulae include phenyl, naphthyl, biphenyl, anthryl and indenyl.

Substituents which the said aryl groups may have include halogen, nitro, cyano, amino (which may have alkyl, alkenyl, cycloalkyl or aryl as a substituent), sulfo, mercapto, hydroxy, carboxy, acyl, sulfoxy, sulfamoyl, carbamoyl, alkyl (which may have amino, halogen, hydroxy, cyano or carboxy as a substituent), alkoxy, aralkyloxy, alkylsulfonamido, methylenedioxy, alkylsulfonyl and alkylsulfonylamino. They may form a fused ring together with a cycloalkyl (e.g. tetrahydronaphthyl, indanyl and acenaphthyl).

Alkoxys in groups represented by $R^1$ in the above formulae preferably have 1 to 6 carbon atoms. As examples of such alkoxys, mention may be made of methoxy, ethoxy, n-propoxy, i-propoxy, n-butoxy, i-butoxy, t-butoxy, n-pentyloxy and n-hexyloxy.

Substituents which the said alkoxy groups may have include halogen, nitro, amino, hydroxy, sulfo, cyano, carboxy, aryl (which may have nitro, amino, hydroxy, alkyl or alkoxy as substituents) and silyl (which may have alkyl, aryl or aralkyl as substituent).

Alkylthio groups in groups represented by $R^1$ in the above formulae preferably have 1 to 6 carbon atoms. As such alkylthio, for example, mention may be made of methylthio, ethylthio, n-propylthio, i-propylthio, n-butylthio, i-butylthio, n-pentylthio and n-hexylthio. Substituents which the said alkylthio groups may have include the same substituents as those mentioned above for alkoxy.

Alkenyls in groups represented by $R^1$ in the above formulae preferably have, for example, 1 to 6 carbon atoms. As examples of such alkenyls, mention may be made of methylene, vinyl, allyl, isopropenyl, 1-propenyl, 2-butenyl, 3-methyl-3-butenyl, 1,3-butadienyl, 1,3-pentadienyl, 4-pentenyl, 1,3-hexadienyl, ethylidene, propylidene, isopropylidene and butylidene.

Substituents which the said alkenyl groups may have include halogen, nitro, amino (which may have acyl as a substituent), sulfo, cyano, hydroxy, carboxy, carbamoyl, sulfamoyl, aryl and acyl.

Alkenylenes in groups represented by $R^1$ in the above formulae preferably have, for example, 2 to 6 carbon atoms. As examples of such alkenylenes, mention may be made of vinylene, 1-propenylene, 2-butenylene, 2-pentenylene and 1,3-hexadienylene.

Cycloalkenyls as represented by $R^{13}$ and $R^{22}$ in the above formulae preferably have, for example, 3 to 8 carbon atoms. As examples of such cycloalkenyls, mention may be made of 1-cyclopropenyl, 1-cyclobutenyl, 1-cyclopentenyl, 2-cyclopentenyl, 3-cyclopentenyl, 1-cyclohexenyl, 2-cyclohexenyl, 3-cyclohexenyl, 1-cycloheptenyl and 1,4-cyclohexadienyl.

Substituents which the said cycloalkenyl groups may have include halogen, nitro, amino, sulfo, cyano, hydroxy, carboxy, carbamoyl and sulfamoyl.

Heterocyclic rings in groups represented by $R^1$ in the above formulae or heterocyclic rings formed together by two or more of these groups include 5- to 7-membered heterocyclic groups containing 1 sulfur, nitrogen or oxygen atom, 5- to 6-membered heterocyclic groups containing 2 to 4 nitrogen atoms and 5- to 6-membered heterocyclic groups containg 1 to 2 nitrogen atoms and 1 sulfur or oxygen atom; these heterocyclic groups may be fused to a 6-membered cyclic group containing not more than 2 nitrogen atoms, a benzene ring or 5-membered cyclic group containing 1 sulfur atom.

As specific examples of the above heterocyclic groups, mention may be made of pyrid-(2-,3- or 4-y), pyrimid-(2-,4- or 5-yl), pyradin-2-yl, pyridazin-(3- or 4-yl), piperazin-1-yl, piperid-1-yl, pyrazol-(1,3- or 4-yl), 4H-pyran-3-yl, 4H-thiopyran-3-yl, thiazol-(2-,4- or 5-yl), isothiazol-(3-,4- or 5-yl), oxazol-(2-,4- or 5-yl), isoxazol-(3-,4- or 5-yl), pyrido[2,3-d]pyrimid-(2-,3-,4-,5- or 7-yl), benzo[1,2-b]-4H-pyran-3-yl, 1,8-naphthylid-(2-,3-,4-,5-,6- or 7-yl), 1,7-naphthylid-(2-,3-,4-,5-,6- or 7-yl), 1,6-naphthilid-(2-,3-,4-,5-,6-,7- or 8-yl), 1,5-naphthilid-(2-,3-,4-,6-,7- or 8-yl), 2,7-naphthilid-(1-,3-,4-,5-,6- or 8-yl), 2,6-naphthilid-(1-,3-,4-,5-,7- or 8-yl), quinol-(2-,3-,4-,5-,6-,7- or 8-yl), thieno[2,3-b]pyrid-(2- or 3-yl), tetrazol-(1- or 5-yl), 1,3,5-thiadiazol-(2- or 4-yl), 1,3,5-oxadiazol-(2- or 4-yl), triazin-2-yl, 1,2,3-triazol-(4- or 5-yl), 1,3,5-triazol-(2- or 5-yl), thiophen-(2- or 3-yl), pyrrol-(1-,2- or 3-yl), fur-(2- or 3-yl), pyrrolidin-1-yl, imidazolidin-(1-,2- or 4-yl), dithiethan-2-yl, tetrahydrofur-(2-,3- or 4-yl), benzo[1,2-b]thiophen-(2- or 3-yl), indol-(1-,2- or 3-yl) and isoindol-(1-,2- or 3-yl).

Substituents which the said heterocyclic groups may have include amino (which may have as a substituent acyl, halogen-substituted alkylacyl, phenyl or alkyl), halogen, nitro, sulfo, cyano, hydroxy, carboxy, oxo, thioxo, $C_{1-10}$-alkyl [which may have as a substituent aryl, halogen, amino, hydroxy, carboxy, alkoxy, alkylsulfonyl, dialkylamino or phosphono (which may have alkyl as a substituent)], cycloalkyl, alkoxy (which may have halogen or hydroxy as a substituent), acyl having 1 to 4 carbon atoms, aryl (which may have halogen, nitro, alkyl, alkoxy, amino, sulfo, hydroxy or cyano as a substituent), oxo, thioxo, amino acid residue-thio (as examples of amino acid residues, mention may be made of residues such as those mentioned below), $C_{1-10}$-alkylthio [which may have as a substituent aryl, halogen, amino, hydroxy, carboxy, alkoxy, alkylsulfonyl, dialkylamino or phosphono (which may have alkyl as a substituent)], heterocyclic ring (which may have alkyl, alkoxy, halogen, nitro, cyano, carboxy, formyl or alkylsulfonyl as a substituent) and groups represented by the formula $R^{50'}-CH=N-$ *wherein $R^{50'}$ represents a heterocyclic ring (which may have as a substituent alkyl, alkoxy, halogen, nitro, cyano, hydroxy, carboxy, formyl or alkylsulfonyl).*

In the above formulae, rings formed by $R^{11}$ together with $R^{10}$ include phthaloyl, succinyl, maleoyl, citraconoyl, glutaryl and adipoyl, as well as 2,2-dimethyl-5-oxo-4-phenyl-imidazolidine. Groups which the said cyclic groups may have as substituents include halogen, nitro, amino, hydroxy, sulfo, cyano and carboxy.

In the above formulae, acyls in acyloxys in groups represented by $R^1$ preferably have, for example, 1 to 4 carbon atoms. As examples of such acyls, mention may be made of formyl, acetyl, propionyl, butyryl and isobutyryl; substituents which may be contained as substituents in these acyls include alkyl (which may have amino, halogen, cyano, alkoxy, carboxy or hydroxy as a substituent).

In the above formulae, amino acid residues represented by $R^{12}$ include glycyl, alanyl, valyl, leucyl, isoleucyl, seryl, threonyl, cysteinyl, cystyl, methionyl, α- or β-aspargyl, α- or γ-glutamyl, lysyl, arginyl, phenylalanyl, phenylglycyl, thyrosyl, histidyl, triptophanyl and prolyl.

Substituents which the said amino acid residues may have include halogen, hydroxy, sulfo, carboxy, cyano, alkylamino, aralkyloxycarbonyl, aralkyloxy and guanidino.

Substituents which can be favorably used as protective groups for amino groups as represented by $R^{12}$ in the above formulae include those used for this purpose in the fields of, for example, β-lactam and peptide syntheses. As examples of such amino-protecting groups, mention may be made of aromatic acyl groups such as phthaloyl, 4-nitrobenzoyl, 4-tert-butylbenzoyl, 4-tert-butylbenzenesulfonyl, benzenesulfonyl and toluenesulfonyl; aliphatic acyl groups such as formyl, acetyl, propionyl, monochloroacetyl, dichloroacetyl, trichloroacetyl, methanesulfonyl, ethanesulfonyl, trifluoroacetyl, malonyl, and succinyl; esterified carboxyl groups such as methoxycarbonyl, ethoxycarbonyl, t-butoxycarbonyl, isopropoxycarbonyl, 2-cyanoethoxycarbonyl, 2,2,2-trichloroethoxycarbonyl, benzyloxycarbonyl, 4-nitrobenzyloxycarbonyl, 4-methoxybenzyloxycarbonyl, diphenylmethyloxycarbonyl, methoxymethylcarbonyl, acetylmethyloxycarbonyl, isobornyloxycarbonyl and phenyloxycarbonyl; methylene groups such as (hexahydro-1H-azepin-1-yl)methylene; sulfonyl groups such as 2-amino-2-carboxyethyl-sulfonyl; and amino-protecting groups other than acyl groups, such as trityl, 2-nitrophenylthio, benzylidene, 4-nitrobenzylidene, di- or trialkylsilyl, benzyl and 4-nitrobenzyl. There is no limitation on selecting protective groups in the present invention; particularly, however, monochloroacetyl, benzyloxycarbonyl, 4-methoxybenzyloxycarbonyl and 4-nitrobenzyloxycarbonyl are desirable.

Substituents which carboxyl in groups as represented by $R^1$ in the above formulae may have include alkyl (which may have halogen, cyano or hydroxy as a substituent), aryl (which may have alkyl, alkoxy, halogen, hydroxy, acyloxy, sulfo, cyano or sulfamoyl as a substituent), silyl (which may have alkyl, aryl or aralkyl as a substituent), heterocyclic rings (which may have amino, alkylamino, sulfamoyl, carbamoyl, halogen, cyano or nitro as a substituent) and amino (which may have alkyl, aryl, cycloalkyl, sulfo or aralkyl as a substituent and which may, together with nitrogen in the said amino group, form a 5- to 6-membered heterocyclic ring).

In the above formulae, esters in esterified carboxyl groups represented by $R^{20}$ include alkyl esters having 1 to 6 carbon atoms. As examples of such alkyl esters, mention may be made of methyl ester, ethyl ester, propyl ester, n-butyl ester, isobutyl ester and tert-butyl ester.

Substituents which amino groups in groups as represented by $R^1$ in the above formulae may have include amidino, iminomethyl, imino-(aryl-substituted) methyl, guanidylcarbonyl, heterocyclic rings* (which may have substituents such as those for the above-mentioned heterocyclic rings), imino (which is substituted by a heterocyclic ring) methyl, alkylcarbonyl, arylcarbonyl, hydroxyalkyl and alkyl.

Substituents which silyls in groups as represented by $R^1$ in the above formulae may have as substituents include alkyl, aryl and aralkyl.

The above $R^{37}$, $R^{38}$ and $R^{39}$ may, together with $R^{40}$, form a cyclic group. As examples of such a cyclic group, mention may be made of 2,5-disilylazacyclopentyl, and these groups may have, for example, alkyl or aryl as a substituent.

As examples of halogens in the description of the above-mentioned substituents, mention may be made of chlorine, bromine, fluorine and iodine.

Alkyls in the foregoing description of the substituents of groups as represented by $R^1$ preferably have 1 to 10, more preferably 1 to 6, still more preferably 1 to 4 carbon atoms unless otherwise specified. As examples of such alkyls, mention may be made of methyl, ethyl, n-propyl, i-propyl, n-butyl, i-butyl, t-butyl, sec-butyl, n-pentyl, isopentyl, n-hexyl, isohexyl, heptyl, octyl, nonyl and decyl.

Cycloalkyls as the above-mentioned substituents preferably have 3 to 6 carbon atoms unless otherwise specified. As examples of such cycloalkyls, mention may be made of cyclopropyl, cyclobutyl, cyclopentyl and cyclohexyl.

Alkoxys as the above-mentioned substituents preferably have 1 to 4 carbon atoms unless otherwise specified. As examples of such alkoxys, mention may be made of methoxy, ethoxy, n-propoxy, i-propoxy, n-butoxy, i-butoxy and t-butoxy.

Aryls as the above-mentioned substituents include phenyl and naphthyl.

Heterocyclic rings as the above-mentioned substituents include heterocyclic rings such as those mentioned above in respect to $R^1$.

Acyls as the above-mentioned substituents preferably have 1 to 6, preferably 1 to 4 carbon atoms unless otherwise specified. As examples of such acyls, mention may be made of formyl, acetyl, propionyl, butyryl, isobutyryl, valeryl, isovaleryl, pivaloyl and hexanoyl.

Aralkyls as the above-mentioned substituents include, for example, benzyl, phenethyl and phenyl-propyl.

Alkenyls as the above-mentioned substituents include alkenyls similar to those mentioned above.

Amino acid residues as the above-mentioned substituents include amino acid residues similar to those represented by $R^{12}$ as mentioned above.

5- to 6-membered heterocyclic rings formed by amino groups as the above-mentioned substituents with nitrogen in the said amino groups include piperidine, pyrrolidine, imidazolidine, morpholine and piperazine.

Not only each above-mentioned group but also each below mentioned group which may be substituted (with asterisk* marked) preferably has 1 to 3 substituents.

Among substituents which groups such as alkyl*, alkenyl*, cycloalkyl*, alkoxy*, aryloxy*, cycloalkenyl*, alkylene*, cycloalkylene* aryl*, aryloxy* and heterocyclic ring* may have, preferred are halogen, amino, hydroxy, carboxy, cyano and nitro. As the substituents of aryl*, aryloxy and heterocyclic ring* groups, also preferred are alkyl, alkoxy, halogen-substituted alkylacylamino, alkylamino. Among substituents of an amino acid residue*, preferred are halogen, alkylamino, hydroxy, carboxy. As the substituents of an amino group, alkylcarbonyl, arylcarbonyl and alkyl are preferred, as those of acyloxy, preferred is alkyl which may be substituted by the above-mentioned preferred substituents.

As specific examples of acylamino groups represented by the formula

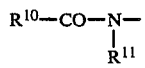

in the above acyl groups, mention may be made of 3-(2,6-dichlorophenyl)-5-methylisoxazol-4-yl-carbonylamino, 4-ethyl-2,3-dioxo-1-piperazino-carbonylamino, 3-phenyl-5-methylisoxazol-4-yl-carbonylamino, 3-(2-chlorophenyl)-5-methylisoxazol-4-yl-carbonylamino, 3-(2-chloro-6-fluorophenyl)-5-methylisoxazol-4-yl-carbonylamino, nicotinylamino, benzoylamino, 4-bromobenzoylamino, 2,6-dimethoxybenzoylamino, formylamino, acetylamino, propionylamino, butyrylamino, isobutyrylamino, pivaloylamino, methoxycarbonylamino, benzyloxycarbonylamino, 1-aminocyclohexylcarbonylamino, 2-amino-cyclohexylcarbonylamino, 3-ethoxynaphthoylamino, 2-(2-amino-4-thiazolyl)-2-ethylideneacetylamino, 2-(2-amino-4-thiazolyl)-2-chloromethyleneacetylamino, phthalimido, succinimido, 1,2-cyclohexanedicarboximide, 2-(trimethylsilyl)ethoxycarbonylamino, 2,2-dimethyl-5-oxo-4-phenylimidazolidine and 4-(carbamoylcarboxymethylene)-1,3-dithiethan-2-yl-carbonylamino.

As specific examples of acylamino groups represented by the formula

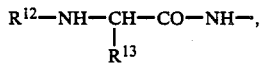

mention may be made of D-alanylamino, benzyl-N-carbobenzoxy-γ-D-glutamyl-D-alanylamino, D-phenylglycyl-D-alanylamino, N-carbobenzoxy-D-alanylamino, N-carbobenzoxy-D-phenylglycylamino, D-analyl-D-phenylglycylamino, γ-D-glutamyl-D-alanylamino, 2-(4-ethyl-2,3-dioxo-1-piperazinocarboxamido)-2-phenylacetylamino, 2-(4-cyclohexyl-2,3-dioxo-1-piperazinocarboxamido)-2-phenylacetylamino, 2-(4-ethyl-2,3-dioxo-1-piperazinocarboxamido)-2-(4-sulfoxyphenyl)-acetylamino, N-(4-ethyl-2,3-dioxo-1-piperazinocarbonyl)-D-alanylamino, N-(4-ethyl-2,3-dioxo-1-piperazinocarbonyl)-D-phenylglycylamino, 2-(2-amino-4-thiazolyl)-2-(4-ethyl-2,3-dioxo-1-piperazinocarboxamido)acetylamino, 2-(4-hydroxy-6-methylnicotinamido)-2-phenylacetylamino, 2-(4-hydroxy-6-methylnicotinamido)-2-(4-hydroxyphenyl)acetylamino, 2-{5,8-dihydro-2-(4-formyl-1-piperazinyl)-5-oxopyrido[2,3-d]pyrimidine-6-carboxamido}-2-phenylacetylamino, 2-(3,5-dioxo-1,2,4-triazine-6-carboxamido)-2-(4-hydroxyphenyl)acetylamino, 2-(3-furfurylideneamino-2-oxoimidazolidine-1-carboxamido)-2-phenylacetylamino, 2-(coumarin-3-carboxamido)-2-phenylacetylamino, 2-(4-hydroxy-7-methyl-1,8-naphthylidene-3-carboxamido)-2-phenylacetylamino, 2-(4-hydroxy-7-trifluoromethylquinoline-3-carboxamido)-2-phenylacetylamino, N-[2-(2-amino-4-thiazolyl)acetyl]-D-phenylglycylamino, 2-(6-bromo-1-ethyl-1,4-dihydro-4-oxothieno[2,3-b]pyridine-3-carboxamido)-2-phenylacetylamino, 2-(4-ethyl-2,3-dioxo-1-piperazinocarboxamido)-2-thienylacetylamino, 2-(4-n-pentyl-2,3-dioxo-1-piperazinocarboxamido)-2-thienylacetylamino, 2-(4-n-octyl-2,3-dioxo-1-piperazinocarboxamido)-2-thienylacetylamino, 2-(4-cyclohexyl-2,3-dioxo-1-piperazinocarboxamido)-2-thienyl-acetylamino, 2-[4-(2-phenylethyl)-2,3-dioxo-1-piperazinocarboxamido]-2-thienylacetylamino, 2-(3-methylsulfonyl-2-oxoimidazolidine-1-carboxamido)-2-phenylacetylamino, 2-(3-furfurylideneamino-2-oxoimidazolidine-1-carboxamido)-2-(4-hydroxyphenyl)acetylamino, 2-(4-ethyl-2,3-dioxo-1-piperazinocarboxamido)-2-(4-benzyloxyphenyl)acetylamino, 2-(4-ethyl-2,3-dioxo-1-piperazinocarboxamido)-2-(4-methoxyphenyl)acetylamino, 2-(8-hydroxy-1,5-naphthylidine-7-carboxamido)-2-phenylacetylamino, 2-(2-amino-4-thiazolyl)-2-formamidoacetylamino, 2-(2-amino-4-thiazolyl)-2-acetamidoacetylamino, 2-phenyl-2-ureidoacetylamino, 2-phenyl-2-sulfoureidoamino, 2-thienyl-2-ureidoacetylamino, 2-amino-3-sulfamoylpropionylamino, 2-amino-2-(1H-indole-3-yl)acetylamino, 2-amino-2-(3-benzo[b]-thienyl)acetylamino, 2-amino-2-(2-naphthyl)acetylamino, D-phenylglycyl, D-2-amino-(4-hydroxyphenyl)acetylamino, D-2-amino-2-(1,4-cyclohexadienyl)acetylamino, D-2-amino-2-(1-cyclohexenyl)acetylamino, D-2-amino-2-(3-chloro-4-hydroxyphenyl)acetylamino, 2-hydroxymethylamino-2-phenylacetylamino, 2-(1-cyclohexenyl)-2-(4-ethyl-2,3-dioxo-1-piperazinocarboxamido)acetylamino, N-[2-(4-ethyl-2,3-dioxo-1-piperazinocarbonyl)]-D-threonylamino, 2-guanylcarboxamido-2-phenylacetylamino, 2-(4-ethyl-2,3-dioxo-1-piperazinocarboxamido)-2-(3,4-dihydroxyphenyl)acetylamino, 2-(4-carboxy-5-imidazolylcarboxamido)-2-phenylacetylamino and 2-amino-2-(3-methylsulfonamidophenyl)acetylamino.

As specific examples of acylamino groups represented by the formula $R^{15}-R^{16}-CO-NH-$, mention may be made of N-[2-(2-amino-4-thiazolyl)-2-methoxyiminoacetyl]-D-alanylamino, N-[2-(2-amino-4-thiazolyl)-2-methoxyiminoacetyl]-D-phenylglycylamino, 2-(2-amino-4-thiazolyl)-2-methoxyiminoacetylamino, 2-(2-chloroacetamido-4-thiazolyl)-2-methoxyiminoacetylamino, 2-(2-amino-4-thiazolyl)-2-methoxyiminoacetylamino, 2-(2-amino-4-thiazolyl)-2-ethoxyiminoacetylamino, 2-(2-amino-4-thiazolyl)-2-isopropoxyiminoacetylamino, 2-(2-amino-4-thiazolyl)-2-butoxyiminoacetylamino, 2-(2-amino-4-thiazolyl)-2-cyclopropylmethyloxyiminoacetylamino, 2-(2-amino-4-thiazolyl)-2-benzyloxyiminoacetylamino, 2-(2-amino-4-thiazolyl)-2-allyloxyiminoacetylamino, 2-(2-amino-4-thiazolyl)-2-[(1-methyl-1-carboxyethyl)oxyimino]acetylamino, 2-(2-amino-4-thiazolyl)-2-[(1-methyl-1-methoxycarbonylethyl)oxyimino]acetylamino, 2-(2-amino-4-thiazolyl)-2-carboxymethyloxyiminoacetylamino, 2-(2-amino-4-thiazolyl)-2-carboxyvinyloxyiminoacetylamino, 2-(2-amino-4-thiazolyl)-2-carboxyethyloxyiminoacetylamino, 2-(2-amino-4-thiazolyl)-2-methoxycarbonylethyloxyiminoacetylamino, 2-(2-amino-5-chloro-4-thiazolyl)-2-methoxyiminoacetylamino, 2-(2-amino-5-bromo-4-thiazolyl)-2-methoxyiminoacetylamino, 2-(2-amino-4-thiazolyl)-2-oxyiminoacetylamino, 2-thienyl-2-methoxyiminoacetylamino, 2-furyl-2-methoxyiminoacetylamino, 2-(1,2,4-thiadiazol-3-yl)-2-methoxyiminoacetylamino, 2-(1,2,4-thiadiazol-5-yl)-2-methoxyiminoacetylamino, 2-(1,3,4-thiadiazolyl)-2-methoxyiminoacetylamino, 2-(4-hydroxyphenyl)-2-methoxyiminoacetylamino, 2-phenyl-2-methoxyiminoacetylamino, 2-phenyl-2-oxyiminoacetylamino, 2-[4-(γ-D-glutamyloxy)phenyl]-2-oxyiminoacetylamino, 2-[4-(3-amino-3-carboxypropoxy)phenyl]-22-oxyiminoacetylamino, 2-thienyl-2-oxyiminoacetylamino, 2-(5-amino-1,2,4-thiadiazol-3-yl)-2-methoxyiminoacetylamino, 2-(5-amino-1,2,4-thiadiazol-3-yl)-2-ethoxyiminoacetylamino, 2-(5-amino-1,2,4-thiadiazol-3-yl)-2-carboxymethyloxyiminoacetylamino, 2-(5-amino-1,2,4-thiadiazol-3-yl)-2-[(1-methyl-1-carboxyethyl)oxyimino]acetylamino, 2-(2-amino-4-thiazolyl)-2-(2-amino-2-carboxy)ethyloxyiminoacetylamino, 2-(2-amino-4-thiazolyl)-2-(dimethylamidomthyloxyimino)acetylamino, 2-amino-4-thiazolyl)-2-(3,4-diacetoxybenzoyloxyimino)acetylamino, 2-(2-amino-4-thiazolyl)-2-(1-carboxycyclopropyloxyimino)acetylamino, 2-(2-amino-4-thiazolyl)-2-(1-carboxycyclobutyloxyimino)acetylamino, 2-(2-amino-4-thiazolyl)-2-(2-imidazolylmethyloxyimino)acetylamino, 2-(2-amino-4- thiazolyl)-2-(2-methyl-4-nitro-1-imidazolylethyloxyimino)acetylamino, 2-(2-amino-4-thiazolyl)-2-(3-pyrazolylmethyloxyimino)acetylamino, 2-(2-amino-4-thiazolyl)-2-(1H-tetrazol-5-yl-methyloxyimino)acetylamino, 2-(2-amino-4-thiazolyl)-2-(2-oxo-3-pyrrolidinyloxyimino)acetylamino, 2-[2-(2-amino-2-carboxyethylthio)]-4-thiazolyl-2-methoxyiminoacetylamino and 2-(2-thioxo-4-thiazolidinyl)-2-methoxyiminoacetylamino.

As specific examples of acylamino groups represented by the formula

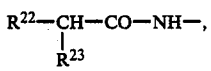

mention may be made of 2-phenyl-2-sulfoacetylamino, 2-hydroxy-2-phenylacetylamino, 2-phenyl-2-sulfamoylacetylamino, 2-carboxy-2-phenylacetylamino, 2-(4-hydroxyphenyl)-2-carboxyacetylamino, 2-phenoxycarbonyl-2-phenylacetylamino, 2-phenyl-2-tolyloxycarbonylacetylamino, 2-(5-indanyloxycarbonyl)-2-phenylacetylamino, 2-formyloxy-2-phenylacetylamino, 2-alanyloxy-2-phenylacetylamino, 2-carboxy-2-thienylacetylamino, 2-(2-methylphenoxycarbonyl)-2-thienylacetylamino, 2-(2-amino-4-thiazolyl)-2-hydroxyacetylamino and 2-[4-(2-amino-2-carboxyethoxycarboxamido)phenyl]-2-hydroxyacetylamino.

As specific examples of acylamino groups represented by the formula $R^{24}-R^{25}-CH_2-CO-NH-$, mention may be made of cyanoacetylamino, phenylacetylamino, phenoxyacetylamino, trifluoromethylthioacetylamino, cyanomethylthioacetylamino, difluoromethylthioacetylamino, 1H-tetrazolyl-1-acetylamino, thienylacetylamino, 2-(2-amino-4-thiazolyl)acetylamino, 4-pyridylthioacetylamino, 2-thienylthioacetylamino, 3,5-dichloro-1,4-dihydro-4-oxopyridine-1-acetylamino, β-carboxyvinylthioacetylamino, 2-(2-aminomethylphenyl)acetylamino, 2-chloroacetylamino, 3-aminopropionylamino, (2-amino-2-carboxy)ethylthioacetylamino, 4-amino-3-hydroxybutyrylamino, 2-carboxyethylthioacetylamino, 2-benzyloxycarbonylaminoacetylamino, β-carbamoyl-β-fluorovinylthioacetylamino, 2-(1-isopropylamino-1-isopropyliminomethylthio)acetylamino, 2-[1-(2-dimethylaminoethyl)-1H-tetrazol-5-yl-thio]acetylamino, 2-(1-methyl-1,3,5-thiazol-2-yl)acetylamino and 2-(4-cyano-3-hydroxy-5-isothiazolylthio)acetylamino.

As specific examples of groups represented by the formula

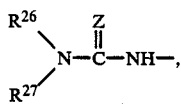

mention may be made of carbamoylamino, methylaminocarbonylamino, ethylaminocarbonylamino, t-butylaminocarbonylamino, isobutylaminocarbonylamino, dimethylaminocarbonylamino, 2-methylphenylaminocarbonylamino, phenylaminocarbonylamino, 3-chlorophenylaminocarbonylamino, 4-nitrophenylaminocarbonylamino, 4-bromophenylaminocarbonylamino, thiocarbamoylamino, methylaminothiocarbonylamino, ethylaminothiocarbonylamino, phenylaminothiocarbonylamino, dimethylaminocarbonylamino and 3-fluorophenylaminocarbonylamino.

As specific examples of groups represented by the formula $R^{28}-NH-$, mention may be made of methylamino, ethylamino, allylamino, cyclohexylamino, cyclohexylmethylamino, benzylamino, 4-chlorobenzylamino, phenylamino, 2-imidazolylamino, 1-methyl-2-imidazolylamino, 2-(2-amino-4-thiazolyl)-2-methoxyimino-thioacetylamino, 1-benzyl-4-pyridiniumamino and 2-acetyl-1-methylvinylamino.

As specific examples of alkylamino groups represented by the formula

mention may be made of dimethylamino, diethylamino, dipropylamino, dibenzylamino, dicyclohexylamino, N-benzyl-N-methylamino, diallylamino, N-phenyl-N-methylamino, pyrrolidinyl, piperidinyl, piperazinyl and morpholinyl.

As specific examples of alkylammonium groups represented by the formula

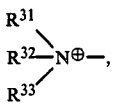

mention may be made of trimethylammonium, triethylammonium, tribenzylammonium, benzyldimethylammonium, methylpyrrolidinium, and methylpiperidinium.

As specific examples of alkenylamino groups represented by the formula

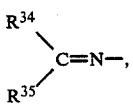

mention may be made of dimethylaminomethylene amino, 1-dimethylaminoethylideneamino, hexahydro-1H-azepin-1-ylmethyleneamino, 1-(N-benzyl-N-methylamino)ethylideneamino, 4-dimethylaminobenzylideneamino, (p-nitro)benzylideneamino and benzylideneamino.

As specific examples of thioamino groups represented by the formula $R^{36}-SO_n-NH-$, mention may be made of benzenesulfonylamino, 4-methylbenzenesulfonylamino, 4-methoxybenzenesulfonylamino, 2,4,6-trimethylbenzenesulfonylamino, benzylsulfonylamino, 4-methylbenzysulfonylamino, trifluoromethylsulfonylamino, phenacylsulfonylamino, methylsulfonylamino, ethylsulfonylamino, 4-fluorobenzenesulfonylamino, benzenesulfinylamino, 2-nitro-benzenesulfinylamino, 2,4-dimethylbenzenesulfinylamino, 4-chlorobenzenesulfinylamino, 4-methoxybenzensulfinylamino, phenylthioamino, 2,4-dinitrophenylthioamino, triphenylmethylthioamino and 2-nitro-4-methoxyphenylthioamino.

As specific examples of silylamino groups represented by the formula

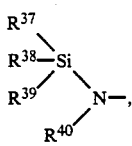

mention may be made of trimethylsilylamino, triethylsilylamino, t-butyldimethylsilylamino, t-butyldiphenylsilylamino, isopropyldimethylsilylamino, triphenylsilylamino, triisopropylsilylamino, tribenzylsilylamino, and (triphenylmethyl)-dimethylsilylamino.

As specific examples of groups represented by the formula

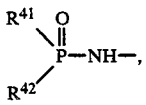

mention may be made of dimethylphosphoamino, diethylphosphoamino, diphenylphosphoamino, dibenzylphosphoamino and di-4-chlorophenylphosphoamino.

As specific examples of groups represented by the formula $R^{43}$—CO—CO—NH, mention may be made of methoxalylamino, ethoxalylamino, phenoxalylamino, benzyloxalylamino, pyruvoylamino, ethyloxalylamino, oxamoylamino, benzylaminooxalylamino, thienyloxalylamino, 2-amino-4-thiazolyl-oxalylamino and ethylaminooxalylamino.

In the above formulae, groups represented by $R^3$, $R^4$ and $R^5$ include organic residues bonded via a carbon atom and organic residues bonded via an oxygen, nitrogen or sulfur atom.

Groups which are preferable for the above-mentioned organic residues bonded via a carbon atom include alkyl*, cycloalkyl, alkenyl*, aryl*, acyl, cyano, carbamoyl, heterocyclic ring* and carboxyl which may be esterified or amidated.

Groups which are preferable for the above-mentioned organic residues bonded via an oxygen atom include groups represented by the formula —O—$R^7$ wherein $R^7$ represents either hydrogen, alkyl, aryl, acyl or carbamoyl, and oxo groups.

Groups which are preferable for the above-mentioned organic residues bonded via a nitrogen atom include, for example, groups represented by the formula

wherein $R^8$ and $R^{8'}$ each represent hydrogen, alkyl, aryl or acyl, whether or not they are the same with each other.

Groups which are preferable for the above-mentioned organic residues bonded via a sulfur atom include groups represented by the formula —S(O)$_n$—$R^9$ wherein $R^9$ represents hydrogen, alkyl*, aryl*, heterocyclic ring* or amino*; n represents 0, 1 or 2.

As examples of groups which alkyl groups represented by the above $R^3$, $R^4$ and $R^5$ may have, mention may be made of hydroxy, acyloxy, carbamoyloxy, amino, dialkylamino, acylamino, alkylthio, heterocyclic ring-thio, carboxy, alkoxycarbonyl, carbamoyl, cyano, azido, aryl and halogen.

Substituents which aryl groups represented by the above $R^3$, $R^4$ and $R^5$ may have e.g. halogen, alkoxy and alkyl.

Substituents which alkenyl groups represented by the above $R^3$, $R^4$ and $R^5$ may have e.g. aryl.

Substituents which heterocyclic rings represented by the above $R^3$, $R^4$ and $R^5$ may have e.g. alkyl.

Substituents which amino groups represented by the above $R^9$ may have e.g. monoalkyl, dialkyl and monoaryl.

As examples of carboxyls which may be esterified for the above $R^3$, $R^4$ and $R^5$, mention may be made of carboxyl and alkyloxycarbonyl.

As examples of carboxyls which may be amidated for the above $R^3$, $R^4$ and $R^5$, mention may be made of groups represented by the formula:

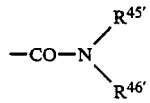

wherein $R^{45'}$ and $R^{46'}$ each represent hydrogen or alkyl, whether identical or not with; $R^{45'}$ and $R^{46'}$ may be combined together with the adjacent nitrogen atom to form a heterocyclic ring.

Alkyls which are preferable for the above alkyls (which include alkyls as a substituent in groups) include those having 1 to 6 carbon atoms.

Cycloalkyls which are preferable for the above cycloalkyls include those having 3 to 6 carbon atoms.

Alkenyls which are preferable for the above alkenyls include those having 1 to 4 carbon atoms.

Acyls which are preferable for the above acyls (which include acyls as a substituent in groups) include those having 1 to 6 carbon atoms and arylcarbonyl.

Alkoxys which are preferable for the above alkoxys (which include alkoxys as a substituent in groups) include those having 1 to 6 carbon atoms.

As specific examples of alkyls having 1 to 6 carbon atoms, cycloalkyls having 3 to 6 carbon atoms, alkenyls having 1 to 4 carbon atoms, acyls having 1 to 6 carbon atoms, alkoxy having 1 to 6 carbon atoms, aryls, heterocyclic rings (which exclude heterocyclic rings formed by the groups together with the adjacent nitrogen atom) and halogens as described above, mention may be made of groups such as those mentioned above for the corresponding groups in the groups represented by $R^1$.

Heterocyclic rings formed by the groups together with the adjacent nitrogen atom as mentioned above are preferably 5- to 6-membered. As specific examples of such heterocyclic rings, mention may be made of pyrrolyl, pyrrolidinyl, piperidinyl and piperazinyl.

Groups which are preferable for the above $R^3$ include methyl, ethyl, isopropyl, vinyl, allyl, cyclopropyl, cyclopentyl, cyclohexyl, phenyl, para-chlorophenyl, para-methoxyphenyl, acetyl, propionyl, benzoyl, methoxycarbonyl, ethoxycarbonyl, carbamoyl, dimethylaminocarbonyl, cyano, carboxyl, hydroxymethyl, acetoxymethyl, carbamoyloxymethyl, chloromethyl, methylthiomethyl, 1-methyl-1H-5-tetrazolylthiomethyl, azidomethyl acetamidomethyl, cyanomethyl, methoxycarbonylmethyl, hydroxyethyl, acetoxyhydroxyethyl, carbamoyloxyethyl chloroethyl, methylthioethyl, 1-methyl-5-tetrazolylthioethyl, cyanoethyl, acetamidoethyl, styryl and phenetyl.

Groups which are preferable for the above $R^4$ and $R^5$ include methyl, ethyl, cyclopropyl, cyclopentyl, cyclohexyl vinyl, allyl, phenyl, para-chlorophenyl, para-methoxyphenyl, acetyl, propionyl, benzoyl, cyano, carbamoyl methoxycarbonyl, ethoxycarbonyl dimethylaminocarbonyl, acetoxymethyl, methylthiomethyl, acetamidomethyl, hydroxy, methoxy, ethoxy, acetoxy, phenyloxy, benzoyloxy, carbamoyloxy, methylamino, dimethylamino, phenylamino, acetylamino, methylthio, ethylthio, 2-acetamidoethylthio, 2N,N-dimethylaminoethylthio 2-aminoethylthio, 2-hydroxyethylthio, carboxymethylthio, methyoxycarbonylmethoxythio, carbamoylmethylthio, phenylthio, 3-pyridazinylthio, 2-pyrimidinylthio, 4-pyridylthio, 1-methyl-1H-5-tetrazolylthio, benzylthio, 4-pyridylmethylthio, sulfamoyl and phenylaminosulfonyl.

As examples of esters of the desired compounds of the present invention, mention may be made of compounds represented by the formula (I) which have at the 2 position and/or the 9 position a group represented by the formula:

—COOR$^{44}$ wherein R$^{44}$ represents either alkyl*, alkenyl* aryl*, cycloalkyl*, heterocyclic ring* or silyl*.

To the description and examples of alkyls*, alkenyls*, aryls*, cycloalkyls*, heterocyclic rings* and silyls* for the above R$^{44}$, are directly applied the description and examples of corresponding groups for R$^1$ mentioned above.

As specific examples of groups represented by the formula —COOR$^{44}$, mention may be made of methyl ester, ethyl ester, n-propyl ester, isopropyl ester, t-butyl ester, t-amyl ester, benzyl ester, 4-bromobenzyl ester, 4-nitrobenzyl ester, 2-nitrobenzyl ester, 3,5-dinitrobenzyl ester, 4-methoxybenzyl ester, benzhydryl ester, phenacyl ester, 4-bromophenacyl ester, phenyl ester, 4-nitrophenyl ester, methoxymethyl ester, methoxyethoxymethyl ester, ethoxymethyl ester, benzyloxymethyl ester, acetoxymethyl ester, pivaloyloxymethyl ester, 2-methylsulfonylethyl ester, 2-trimethylsilylethyl ester, methylthiomethyl ester, trityl ester, 2,2,2-trichloroethyl ester, 2-iodoethyl ester, cyclohexyl ester, cyclopentyl ester, allyl ester, cinnamyl ester, 4-picolinyl ester, 2-tetrahydropyranyl ester, 2-tetrahydrofuranyl ester, trimethylsilyl ester, t-butyldimethylsilyl ester, t-butyldiphenylsilyl ester, acetylmethyl ester, 4-nitrobenzoylmethyl ester, 4-mesylbenzoylmethyl ester, phthalimidomethyl ester, propionyloxymethyl ester, 1,1-dimethylpropyl ester, 3-methyl-3-butenyl ester, succinimidomethyl ester, 3,5-di-t-butyl-4-hydroxybenzyl ester, mesylmethyl ester, benzenesulfonylmethyl ester, phenylthiomethyl ester, iminomethylaminoethyl ester, 1-iminoethylaminoethyl ester, dimethylaminoethyl ester, pyridine-1-oxido-2-methyl ester, methylsulfinylmethyl ester, bis-(4-methoxyphenyl)methyl ester, 2-cyano-1,1-dimethyl ethyl ester, t-butyloxycarbonylmethyl ester, benzoylaminomethyl ester, 1-acetoxyethyl ester, 1-isobutyryloxyethyl ester, 1-ethoxycarbonyloxyethyl ester, phthalide ester, 4-t-butylbenzyl ester, 5-indanyl ester, 5-methyl-2-oxo-1,3-dioxolen-4-yl-methyl ester and 5-t-butyl-2-oxo-1,3-dioxolen-4-yl-methyl ester.

This invention includes not only the esters described above, but also pharmaceutically acceptable esters which are able to be converted into the compound (I) in the organism. As the esters applicable as metabolically unstable, nontoxic esters which can be converted into the compound (I) in the organism, there may be mentioned, for example, the esters mentioned above with reference to —COOR$^{44}$.

The compounds of the present invention may be used in the free form in respect to the carboxyl group at the 2 position, but they may also be used in the form of a pharmacologically acceptable salt prepared via conventional methods. For example, the compounds of the present invention, before use, may be allowed to form salts with non-toxic cations such as sodium and potassium, basic amino acids such as arginine, ornitine, lysine and histidine; and polyhydroxyalkylamines such as N-methylglucamine, diethanolamine, triethanolamine and trishydroxymethylaminomethane. In cases where $R^1$, $R^3$, $R^4$ and/or $R^5$ contains a basic group (e.g. amino group), the compounds of the present invention, before use, may be allowed to form salts with, for example, organic acids such as acetic acid, tartaric acid and methanesulfonic acid; inorganic acids such as hydrochloric acid, hydrobromic acid, sulfuric acid and phosphoric acid; and acidic amino acids such as arginine, aspartic acid and glutamic acid.

The compound of the present invention can cooperate with a base to form a salt. As examples of so formed salts, mention may be made of salts formed with an inorganic base such as sodium, potassium, lithium, calcium, magnesium or ammonium salt; and salts formed with an organic base such as pyridine, collidine, triethylamine or triethanolamine.

Among the compounds (I), particularly preferred types are the compounds represented by the formula:

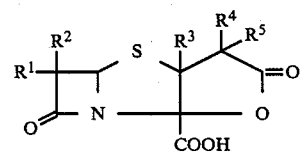

wherein $R^1$ represents hydrogen, an amino group which may be acylated with a carboxylic acid, or an alkyl which may be substituted hydroxy group; $R^2$ represents hydrogen, a methoxy group or a formylamino group and $R^3$, $R^4$ and $R^5$ independently represent hydrogen or an alkyl, their esters or their salts.

The production method for the desired compounds of the present invention is described below.

The desired compounds of the present invention, namely, compounds having a 4,10-dioxo-3-oxa-7-thia-1-azatricyclo[6,2,0,0$^{2,6}$]decane-2-carboxylic acid skeleton, their esters or their salts can be obtained via the cyclization of a compound having a 2-oxo-3-(2-azetidinon-4-yl)thioglutaric acid skeleton, its ester, a compound having a 3-(2-azetidinon-4-yl)thio-5-oxo-tetrahydrofuran-2-carboxylic acid skeleton having at the 2 position a leaving group or its ester.

Specifically, of the desired compounds of the present invention, the compounds represented by the general formula:

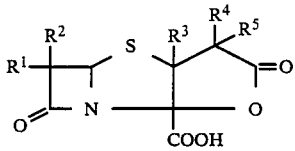 (I)

wherein R[1], R[2], R[3], R[4] and R[5] are of the same meanings as defined above, their esters or their salts can be produced via the cyclization of either the compound represented by the formula:

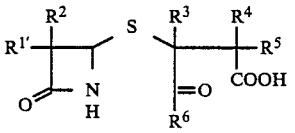 (II)

wherein R[1]' represents hydrogen or an organic residue bonded via nitrogen or carbon; R[6] represents a group derivable from carboxyl group; R[2], R[3], R[4] and R[5] are of the same meanings as defined above or the compound represented by the formula:

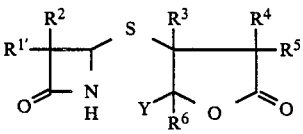 (III)

wherein Y represents a leaving group; R[1]', R[2], R[3], R[4], R[5] and R[6] are of the same meanings as defined above to obtain the compound (I') represented by the general formula:

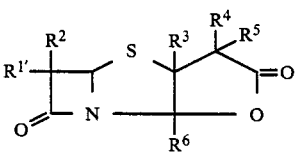 (I')

wherein R[1]', R[2], R[3], R[4], R[5] and R[6] are of the same meanings as defined above, which is further subjected to converting reaction for R[1]' and/or R[6] if desired.

To the description and examples of the above R[1]' are directly applied those of R[1] mentioned previously.

Needless to say, the compounds (I'), which fall within the scope of the compounds (I), consitute the desired compounds of the present invention.

As examples of groups derivable from carboxyl group, represented by R[6] in the above formulae, mention may be made of groups represented by the formula:

—COOR[44']

wherein R[44]' represents alkyl*, alkenyl*, aryl*, cycloalkyl*, heterocyclic ring* or silyl* and groups represented by the formula:

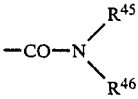

wherein R[45] and R[46] each represent hydrogen, alkyl*, aryl*, cycloalkyl*, alkenyl* or heterocyclic ring*; R[45] and R[46] may be combined together with the adjacent nitrogen atom to form a heterocyclic ring*.

In the above formulae, groups derivable from carboxyl group, represented by R[6] preferably have a molecular weight of, for example, not more than 500.

To the description and specific examples of groups represented by the formula —COOR[44]', specifically those of the —COOR[44] mentioned above are also directly applied here.

As specific examples of groups represented by the formula

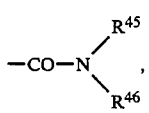

mention may be made of dimethylamide, diethylamide dipropylamide, dibenzylamide, dicyclohexylamide, N-benzyl-N-methylamide, diallylamide, N-phenyl-N-methylamide, pyrrolidinamide, piperidinamide, piperazinamide, morpholinamide, carboxymethylamide and 1-carboxyethylamide.

In the above formulae, to a leaving group represented by Y, there can be applied any group that can couple with the hydrogen of the NH group of the β-lactam ring of the compound (III) and form a C-N bond. As examples of such groups, mention may be made of halogens (e.g. bromine and chlorine), sulfonyloxys having a substituent (e.g. alkyl and aryl; as examples of alkyls and aryls, mention may be made of the same substituents as mentioned for R[1] above) (such sulfonyloxys include p-toluenesulfonyloxy, p-nitrophenylsulfonyloxy and methanesulfonyloxy) and di-substituted phospholyloxys (e.g. diphenylphospholyloxy and diethylphospholyloxy).

The conversion of the compound (II) to the compound (I') may be carried out in the presence of a condensing agent, C-terminal activator, acid or Lewis acid.

The said reaction is preferably carried out in a solvent. A C-terminal activator here means a reagent which makes carboxylic acid convert itself to a reactive derivative in peptide bond formation in the peptide field or β-lactam amino group acylation.

As specific examples of condensing agents which can be used here, mention may be made of N,N'-dicyclohexylcarbodiimide (hereinafter also referred to as DCC); a combination of DCC with N-hydroxysuccinimide or 1-hydroxybenzotriazole; N-ethyl-N'-[3-(dimethylamino)propyl]carbodiimide; carbonyldiimidazole; N-ethyl-5-isoxazolium-3'-sulfonate; 2-ethyl-7-hydroxybenzisoxazoliumtrifluoroborate; 1-ethoxycarbonyl-2-ethoxy-1,2-dihydroquinoline; a combination of 2,2'-dipyridyl disulfide and triphenylphosphine; combination of carbon tetrachloride and triphenylphosphine; 2-halogenopyridinium salts such as 2-chloro-1-methyl-pyridinium iodide and 2-fluoro-1-methyl-pyridinium tosylate; pyrimidinium salts such as 2-chloro-1-methyl-pyrimidinium fluorosulfate; onium salts of azalene such as 2-chloro-3-ethyl-benzoxazolium tetrafluoroborate and 2-fluoro-3-methyl-benzothiazolium fluorosulfate [refer to Angewandte Chemie, International Edition, 18, 707 (1979)].

Said reactive derivatives of carboxylic acid include acid halides such as acid chlorides and acid bromides;

acid azides; monoalkyl carbonate mixed acid anhydrides; mixed acid anhydrides with aliphatic carboxylic acids such as acetic acid, pivalic acid, valeric acid, isovaleric acid and trichloroacetic acid; mixed acid anhydrides with acids such as phosphoric acids (e.g. diphenylphosphoric acid and diethylphosphoric acid) and sulfuric acid; mixed acid anhydrides with, for example, benzoic acid; symmetric-type acid anhydrides; amide compounds having an acyl group bonded to the nitrogen in the ring, such as pyrazole, imidazole, 4-substituted imidazole, dimethylpyrazole, benzotriazole and thiazolidine-2-thione; active esters formed with, for example, 4-nitrophenyl, 2,4-dinitrophenyl, trichlorophenyl, pentachlorophenyl, pentafluorophenyl, cyanomethyl, N-hydroxy-succinimide and N-hydroxyphthalimide; and active thio esters formed with heterocyclic thiol such as 2-pyridylthiol or 2-benzthiazolylthiol.

C-terminal activators which can be used for the conversion of carboxylic acid to these reactive derivatives include the reagents described in "Peptide Synthesis", edited by Nobuo Izumiya, Tetsuo Kato, Motonori Ono and Tohiko Aoyagi, pp. 117–153, published in 1975 (Maruzen). As specific examples of such activators, mention may be made of halogenating agents such as thionyl chloride, thionyl bromide, sulfuryl chloride, phosphorus oxychloride, oxalyl chloride, chlorine, bromine, carbon tetrachloride and triphenylphosphine; sulfonylating agents such as p-toluenesulfonic anhydride, p-nitrobenzenesulfonic anhydride, 2,4,6-triisopropylphenylsulfonic anhydride, methanesulfonic anhydride, p-toluenesulfonyl chloride and p-chlorobenzenesulfonyl chloride; and phosphorylating agents such as diphenyl phosphochloride, dimethyl phosphochloride and diethylphosphochloride.

Acids which can be used for this reaction include hydrochloric acid, sulfuric acid, trifluoroacetic acid, methanesulfonic acid and camphorsulfonic acid.

Lewis acids which can be used for this reaction include boron trifluoride etherate, zinc chloride, tin tetrachloride, aluminum chloride, titanium tetrachloride and boron trichloride.

Any solvent can be used, as long as it does not affect the reaction; solvents which can be used for this reaction include ordinary solvents such as dichloromethane, chloroform, tetrahydrofuran, dioxane, diethyl ether, ethyl acetate, benzene, toluene, n-hexane, acetonitrile and dimethylformamide.

This reaction may be carried out in the presence of a base in some cases (for example, in cases where 2-chloro-1-methylpyridinium iodide, 2,2'-dipyridyl disulfide-triphenylphosphine or carbon tetrachloride-triphenylphosphine is used as a condensing agent). Bases which can be used herein include organic residues such as triethylamine, diisopropylethylamine, N-methylmorpholine and 3,4-dihydro-2H-pyrido[1,2-a]pyrimidine-2-one; and inorganic bases such as sodium bicarbonate. Of these bases, 3,4-dihydro-2H-pyrido[1,2-a]pyrimidine-2-one is preferable.

This reaction may also be carried out in the presence of a substance such as silver chloride, silver tetraborofluorate or silver perchlorate in case where 2,2'-dipyridyl sulfide-triphenylphosphine is used as a condensing agent.

Reaction temperature is not specifically limited, as long as the reaction proceeds, and the reaction is usually conducted at −50° to 150° C., preferably −10° to 100° C. Reaction time is normally 5 minutes to 30 hours, varying depending on the type of starting materials, reagents and solvents, and reaction temperature etc.

In cases where a Lewis acid is used as a catalyst for condensation, a dehydrating agent such as a molecular sieve may be allowed to coexist in the reaction system.

The compound (I) can also be produced by cyclizing compound (III) to obtain the compound (I'), which is further subjected to converting reaction for $R^{1'}$ and/or $R^6$ if desired.

The conversion of the compound (III) to the compound (I') can normally be achieved by treating the compound (III) with a base. The said reaction is preferably carried out in a solvent. Bases which can be used include organic amines such as triethylamine, tripropylamine, tri-n-butylamine, diisopropylethylamine, triethylenediamine, 1,4-diazabicyclo[2,2,2]octane (hereinafter sometimes referred to as DABCO), 1,8-diazabicyclo[5,4,0]-7-undecene (hereinafter sometimes referred to as DBU), N-methylmorpholine, N-methylpiperidine, N-methylpyrrolidine, 3,4-dihydro-2H-pyrido[1,2-a]-pyrimidine-2-one, 4-dimethylaminopyridine, pyridine, lutidine and γ-collidine; alkali metals such as lithium, sodium, potassium and cesium; alkaline earth metals such as magnesium and calcium; and their hydrides, hydroxides, carbonates and alcoholates. Solvents which can be used include ordinary solvents such as dichloromethane, chloroform, tetrahydrofuran, dioxane, benzene, toluene, acetonitrile, dimethylacetamide and dimethylformamide. Of the abovementioned bases, liquid ones may also be used for the dual purposes of base and solvent. In this reaction, the base is usually used in a molar ratio of about 1 to 1 with compound (III), but it may exceed this, as long as it does not interfere with the reaction. Reaction is usually conducted at −20° to 100° C.; reaction time is usually 5 minutes to 30 hours.

Compound (I), its ester or its salt can be produced by further subjecting compound (I') obtained as above to the converting reaction for $R^{1'}$ and $R^6$, if necessary. Converting reactions which can be employed for this purpose include acyl-cleavage reaction by the imino ether method, deprotection reaction, acylation, ureidation (thioureidation), alkylation, alkenylation, thionation, silylation, phosphorylation, esterification and amidation.

In the acyl-cleavage reaction of the compound (I') by the imino ether method, the compound (I'), wherein $R^{1'}$ is a group represented by the formula

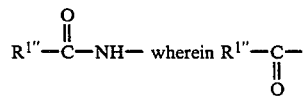

represents the part excluding the nitrogen atom in the organic residue bonded via the nitrogen, is at first reacted with phosphorus pentachloride, phosgene, phosphorus trichloride, phosphorus oxychloride or the like. It is recommended that the abovementioned reagents be used in a molar ratio of about 1 to 5, preferably between 1.5 and 3 to 1 with compound (I'). This reaction is favorably carried out in the presence of a solvent such as methylene chloride, dichloroethane, chloroform, carbon tetrachloride or trichloroethane. It is recommended that for the acceleration of the reaction, for example, pyridine, N,N-dimethylaniline, triethylamine, aniline or toluidine be used in an excess amount, for example, in a molar ratio of about 3 to 20, preferably between 5 and 10 to 1 of compound (I').

It is recommended that the said reaction be carried out at a temperature of $-30°$ to $0°$ C., preferably $-15°$ to $-5°$ C., and reaction time be 15 minutes to 8 hours, preferably 30 minutes to 2 hours. It is advantageous to carry out this reaction while stirring.

Then, an excess amount of methanol is added, and the reaction liquid is stirred at $-30°$ to $0°$ C., preferably $-15°$ to $-5°$ C., for 15 minutes to 2 hours, preferably 30 minutes to 1 hour to convert imino chloride produced as an intermediate to imino ether. The reaction mixture is then further stirred at $10°$ to $40°$ C., preferably $20°$ to $30°$ C. for 30 minutes to 2 hours to complete the reaction. To the reaction mixture dilute hydrochloric acid is added to cleave the C-N bond. Reaction temperature is $10°$ to $40°$ C., preferably $20°$ to $30°$ C.; reaction time is 15 minutes to 2 hours, preferably 30 minutes to 1 hour.

The reaction mixture obtained as above is then neutralized with, for example, sodium bicarbonate, after which it is extracted with a water-immiscible organic solvent such as methylene chloride, diethyl ether or ethyl acetate to obtain the reaction product. These three successive reactions for the acyl-cleavage reaction can be carried out according to the conventional manner.

The deprotection reaction can be also carried out according to the conventional manner, and it can be achieved using a suitable method selected from routine methods such as those using acid, those using a base, those using hydrazine and those by reduction, according to the type of the protective group. In the case of the method using acid, acids which can be used include inorganic acids such as hydrochloric acid, sulfuric acid, and phosphoric acid; and organic acids such as formic acid, acetic acid, trifluoroacetic acid and propionic acid; acidic ion exchange resins can also be used; their selection varies with the type of the protective group. In the case of the methods using a base, bases which can be used include inorganic bases such as hydroxides and carbonates of alkali metals (e.g. sodium and potassium) or alkaline earth metals (e.g. calcium and magnesium) and organic bases such as metal alkoxides, organic amines and quarternary ammonium salts; basic ion exchange resins can also be used; their selection varies with the type of the protective group and other factors. When a solvent is used in the case of the above-mentioned methods using an acid or a base, hydrophilic solvents, water or mixed solvents are frequently employed.

In the case of the methods by reduction, procedures which can be employed include the procedure using either a metal such as tin or zinc or a metal compound such as chromium dichloride or chromium acetate in combination with an organic or inorganic acid such as acetic acid, propionic acid or hydrochloric acid; the procedure of reduction in the presence of a metal-catalyst for catalytic reduction; their selection varies with the type of the protective group catalysts which can be used for the purpose of catalytic reduction include platinum catalysts such as platinum wire, platinum sponge, platinum black, platinum oxide and colloidal platinum; palladium catalysts such as palladium sponge, palladium black, palladium oxide, palladium barium sulfate, palladium barium carbonate, palladium carbon, palladium silica gel and colloidal palladium; and reduced nickel, nickel oxide, Raney nickel, Urushibara nickel etc. In the case of the reduction methods using a metal and an acid in combination, metals which can be used include iron and chromium, and acids which can be used include inorganic acids such as hydrochloric acid and organic acids such as formic acid, acetic acid and propionic acid. The method by reduction is usually carried out in a solvent, for example, when the procedure of catalytic reduction is employed, alcohols such as methanol, ethanol, propyl alcohol and isopropyl alcohols and ethyl acetate etc. are frequently used. In the case of the procedure of reduction using a metal and an acid in combination, water, acetone etc. are frequently used, but when the acid is a liquid, the acid itself can also be used as a solvent.

In the case of the method using acid, the method using base or the method by reduction, the reaction is usually carried out under cooling to warming conditions.

Protective groups in respective groups in the obtained compound can be eliminated in the same manner as described above. In short, the said deprotection reaction can be conducted by a known method.

For example, by subjecting the compound (I') wherein $R^{1'}$ is a protected amino group and $R^6$ is a group of the formula—$COOR^{44'}$ ($R^6$ and $R^{44'}$ are as defined above) to deprotection reaction for the amino protective group in the $R^{1'}$ at the 9 position, the ester compound at the 2-position of the compound (I) wherein $R^1$ is an amino group [which may be hereinafter referred to as compound (I-1)] can be obtained. For example, by subjecting the compound (I') (wherein $R^1$ is an organic residue bonded via nitrogen and $R^6$ is a group of the formula—$COOR^{44'}$) to deprotection reaction for the group $R^{44'}$, compound (I) wherein R' is an organic residue bonded via nitrogen [which may be hereinafter referred to as compound (I-2)] can be obtained. For example, by subjecting compound (I-1) or compound (I-2) to further deprotection for the group represented by $R^{44'}$ or for the amino protective group at the 9-position respectively, compound (I) wherein $R^1$ is an amino group [which may be hereinafter referred to as compound (I-3)] can be obtained. Alternatively, by subjecting the compound (I') (wherein $R^{1'}$ is a protected amino and $R^6$ is a group of the formula —$COOR^{44'}$) to deprotection reaction for both of the amino-protective group at the 9 position and the group represented by $R^{44'}$ compound (I-3) can be obtained at one stroke.

The compound (I-1) can also be converted to the compound (I-2) via a reaction such as acylation, ureidation (thioureidation), alkylation, alkenylation, thionation, silylation or phosphorylation. The said reactions are hereinafter described in detail.

The acylation of the amino group can be achieved by reacting the starting compound with an acylating agent containing an acyl group in the group $R^1$, such as a reactive derivative of carboxylic acid, in a solvent. Reactive derivatives of carboxylic acid which can be used include acid halides, acid anhydrides, active amide compounds, active esters and active thio esters; these reactive derivatives are specifically described in the following:

(1) Acid halides:
Acid halides which can be used herein include acid chlorides and acid bromides.

(2) Acid anhydrides:
Acid anhydrides which can be used herein include monoalkyl carbonic acid mixed acid anhydrides, mixed acid anhydrides composed of aliphatic carboxylic acids (e.g. acetic acid, pivalic acid, valeric acid, isovaleric acid and trichloroacetic acid), mixed acid anhydrides composed of aromatic carboxylic acids (e.g. benzoic acid) and symmetric-type acid anhydrides.

(3) Amide compounds:

Amine compounds which can be used herein include compounds having an acyl group bonded to the nitrogen in the ring, such as pyrazole, imidazole, 4-substituted imidazole, dimethylpyrazole, benzothiazole and benzotriazole.

(4) Active esters:

Active esters which can be used herein include esters such as methyl esters, ethyl esters, methoxymethyl esters, propargyl esters, 4-nitrophenyl esters, 2,4-dinitrophenyl esters, trichlorophenyl esters, pentachlorophenyl esters, mesylphenyl esters and benzotriazolyl esters, as well as esters formed with 1-hydroxy-1H-2-pyridone, N-hydroxysuccinimide, N-hydroxyphthalimide or the like.

(5) Active thio esters:

Active thio esters which can be used herein include thio esters formed with a heterocyclic thiol such as 2-pyridylthiol or 2-benzthiazolylthiol.

Various reactive derivatives as described above can be properly selected according to the type of the carboxylic acid.

This reaction may be carried out in the presence of a base. Bases which can be used for this purpose include tertiary amines such as aliphatic tetiary amines (e.g. trimethylamine, triethylamine, tripropylamine and tri-n-butylamine), N-methylpiperidine, N-methylpyrrolidine, cyclohexyldimethyl amine and N-methylmorpholine; dialkylamines such as di-n-butylamine, diisobutylamine and dicyclohexylamine; aromatic amines such as pyridine, lutidine and γ-collidine; and hydroxides or carbonates of alkali metals such as lithium, sodium and potassium or alkaline earth metals such as calcium and magnesium.

In this method, the reactive derivative of carboxylic acid is usually used in a molar ratio of about 1 to 1 of the compound (I-1), but it may also be used in excess, as long as it does not interfere with the reaction. When a base is used, the base is usually used in an amount of about 1 to 30 equivalents, preferably about 1 to 10 with compound (I-1), varying with the types of the used starting compound (I-1), reactive derivative of carboxylic acid and other reaction conditions. This reaction is usually carried out in a solvent. Solvents which can be used include ordinary organic solvents, for example, ethers such as dioxane, tetrahydrofuran, diethyl ether, diisopropyl ether, propylene oxide and butylene oxide; esters such as ethyl acetate and ethyl formate; hydrocarbon halides such as chloroform, dichloromethane, 1,2-dichloroethane and 1,1,1-trichloroethane; hydrocarbons such as benzene, toluene and n-hexane; amides such as N,N-dimethylformamide and N,N-dimethylacetamide; and nitriles such as acetonitrile. These solvents are used either singly or in combination. Of the above-mentioned bases, liquid ones can also be used for the dual purposes of base and solvent. Reaction temperature is not specifically limited, as long as the reaction proceeds, but the reaction is carried out usually at $-50°$ to $150°$ C., preferably $-30°$ to $80°$ C. The reaction usually completes itself within several ten minutes to several ten hours, though reaction time varies with the types of the used starting compound, base and solvent and reaction temperatures, but it requires several ten days in some cases.

The conversion of the amino group to a ureido or thioureido group can be achieved by reacting the starting compound with a substituted isocyanate or isothiocyanate represented by the formula $R^{26}$—N=C=Z (In this formula, $R^{26}$ and Z are of the same meanings as defined above.) in the presence of a solvent. Such substituted isocyanates which can be used include methyl isocyanate, ethyl isocyanate, phenyl isocyanate and p-bromophenyl isocyanate, and such substituted isothiocyanates which can be used include methyl isothiocyanate and phenyl isothiocyanate. In this reaction, the substituted isocyanate or substituted isothiocyanate is usually used in an equivalent to compound (I-1), but it can exceed this, as long as it does not interfere with the reaction. Solvents which can be used include tetrahydrofuran, diethyl ether, ethyl acetate, chloroform, dichloromethane and toluene. Reaction temperature is about $-20°$ to $50°$ C., and reaction time is usually about 10 minutes to 5 hours.

The reaction by which a compound having an alkyl group bonded to the amino group of the compound (I-1) via carbon is hereinafter described as alkylation.

The alkylation of the compound (I-1) can be conducted by reacting the compound (I-1) with an alkylating agent containing a group corresponding to the group bonded to the nitrogen via carbon in the group $R^1$. Substances which can be used as alkylating agents include alkyl halide compounds such as propyl chloride, butyl chloride, benzyl chloride, butyl bromide, benzyl bromide, allyl bromide, methyl iodide, ethyl iodide and propyl iodide; dialkyl sulfate compounds such as dimethyl sulfate and diethyl sulfate; substituted sulfonate compounds such as methyl mesylate, ethyl mesylate, methyl tosylate and ethyl tosylate; and alkyl dihalide compounds (e.g. 1,5-dichloropentane and 1,4-dichlorobutane). This reaction, is usually carried out in a solvent; solvents which can be used include water, methanol, ethanol, benzyl alcohol, benzene, N,N-dimethylformamide, tetrahydrofuran and acetonitrile. The reaction temperature is about $20°$ to $200°$ C., and the reaction time is about 30 minutes to 50 hours. This reaction by changing reaction conditions such as the molar ratio of the alkylating agent to the compound (I-1), permits the selective production of a secondary amine compound, tertiary amine compound or quarternary ammonium compound. The introduction of a different substituent to the relevant nitrogen is also possible by conducting the reaction stepwise. The reaction of introducing a group bonded via carbon other than alkyl can also be carried out in the same manner as described above.

The said alkylation can also be achieved by reacting the compound (I-1) with a carbonyl compound in the presence of a reducing agent. Reducing agents which can be used for this reaction include lithium alminum hydride, sodium cyanoborohydride, sodium borohydride, sodium, sodium amalgam and combinations of zinc and acid. This reaction can also be achieved by catalytic reduction using, for example, palladium, platinum, rhodium or the like as a catalyst.

The reaction of converting the amino group to a group represented by the formula $R^{28}$—NH— (e.g. an imino-substituted alkylamino group, alkylimino-substituted alkylamino group or substituted guanidino group):

The reaction of converting the amino group to an imino-substituted alkylamino group or alkylimino-substituted alkylamino group can be achieved by reacting the starting compound with, for example, an imide ester in a solvent such as dioxane, tetrahydrofuran, N,N-dimethylformamide, chloroform, acetone, acetonitrile or water. Imide esters which can be favorably used include methyl formimidate, ethyl formimidate, benzyl formimidate, methyl acetoimidate, ethyl acetoimidate, methylphenyl acetoimidate, ethyl N-methylformimidate, methyl N-ethylformimidate and methyl N-isopropylformimidate. Reaction temperature is 0° to 25° C., and reaction time is usually 1 hour to 6 hours. The reaction of converting the amino group to a guanidino group can be achieved by reacting the starting compound with, for example, an O-alkyl or O-aryl pseudourea or an S-alkyl or S-aryl pseudothiourea in a solvent such as water, N,N-dimethylformamide or hexamethylenephosphoramide. Such pseudoureas which can be used include O-methyl pseudourea, S-methyl pseudourea, O-2,4-dichlorophenyl pseudourea and O-N,N-trimethyl pseudourea, and such pseudothioureas which can be used include S-p-nitrophenyl pseudothiourea. Reaction temperature is 0° to near 40° C., and reaction time is usually 1 hour to 24 hours.

The alkenylation(imination) of the compound (I-1) can be achieved by the dehydrating condensation of the compound (I-1) and a carbonyl compound (e.g. propionaldehyde and diethyl ketone). This reaction proceeds even in the absence of solvent, but it can also be carried out in a solvent. An acid or base may be used as a catalyst. The desired compound can also be produced by refluxing the compound (I-1) and a carbonyl compound while heating either in the presence of a dehydrating agent or using a dehydrating apparatus such as Dean-Stark. Solvents which can be used for this reaction include benzene, toluene, dichloromethane and ethanol. Reaction temperature is about 0° to 200° C., and reaction time is about 1 hour to 20 hours. Acids which can be used as catalysts include benzenesulfonic acid, methanesulfonic acid, sulfuric acid, boron trifluoride and zinc chloride; bases which can be used as catalysts include potassium hydroxide and sodium carbonate. Substances which can be used as dehydrating agents for this reaction include molecular sieves, silica gel, anhydrous magnesium sulfate and anhydrous sodium sulfate.

The thionation of the compound (I-1) is normally achieved by reacting compound (I-1) with a thio halide compound represented by the formula $R^{36}$—SOn—X (wherein X represents a halogen such as chlorine or bromine; $R^{36}$ and n have the same meanings as defined above, e.g., sulfonyl halides, sulfinyl halides and sulfenyl halides) in a solvent in the presence of a base. Solvents which can be used for this reaction include water, acetone, dioxane, N,N-dimethylformamide, benzene, tetrahydrofuran, dichloromethane and their mixtures. Bases which can be used include organic bases such as pyridine, picoline, triethylamine, diisopropylethylamine and N-methylmorpholine; and inorganic bases such as sodium hydroxide, potassium hydroxide, sodium carbonate, sodium bicarbonate and potassium carbonate. In this reaction, the thio halide compound is usually used in an amount of about 1 to 10 equivalents with compound (I-1); and the base, in about 1 to 10 equivalents to compound (I-1). Reaction temperature is about −20° to 80° C., and reaction time is 15 minutes to 10 hours.

This reaction can also be conducted using a thio acid anhydride (e.g., toluenesulfonic anhydride and trifluoromethanesulfonic anhydride) in place of such a thio halide compound. This reaction can also be achieved by reacting the starting compound with a thionating reagent such as N-sulfonyl-N-methylpyrrolidinium, N-sulfonylimidazolide and N-sulfonyl-1H-1,2,4-triazolide.

The silylation of compound (I-1) can be normally achieved by reacting compound (I-1) with a silyl halide compound represented by the formula

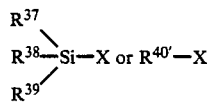

wherein $R^{37-39}$ are the same meanings as defined above; $R^{40'}$ and X respectively represent silyl which may have substituents such as those mentioned above for silyl* concerning $R^1$ and halogen. (e.g. silyl chloride compounds and silyl bromide compounds) in the presence of a base. Bases which can be used for this purpose include organic bases such as pyridine, picoline, triethylamine, diisopropylethylamine and N-methylmorpholine. The reaction is preferably carried out in a solvent; solvents which can be used for this purpose include acetone, dioxane, N,N-dimethylformamide, benzene, tetrahydrofuran and dichloromethane. Reaction temperature is about −20° C. to the boiling point of the solvent used, or about −20° to 80° C., and reaction time is about 15 minutes to 20 hours.

The phosphorylation of compound (I-1) can normally be achieved by reacting compound (I-1) with a phosphoryl halide e.g. a phosphoryl chloride represented by the formula

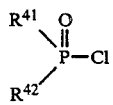

(wherein $R^{41}$ and $R^{42}$ have the same meanings as defined above, e.g., dimethylphosphoryl chloride, diethylphosphoryl chloride, diphenylphosphoryl chloride and dibenzylphosphoryl chloride) in an equivalent to compound (I-1) in a solvent in the presence of a nearly equal or excess amount of a base. Bases which can be used include organic bases such as pyridine, picoline, triethylamine and N-methylmorpholine; and inorganic bases such as sodium hydroxide, potassium hydroxide, sodium bicarbonate and sodium carbonate. Solvents which can be used include water, acetone, acetonitrile, dioxane, N,N-dimethylformamide, tetrahydrofuran, dichloromethane and their mixtures. Reaction temperature is about −20° to 80° C., and reaction time is about 15 minutes to 15 hours.

Compound (I-3) can be converted to compound (I-2) by reactions such as acylation, ureidation (thioureidation), alkylation, alkenylation, thionation, silylation or phosphorylation. These converting reactions can be conducted in the same manner as the aforementioned reactions for converting compound (I-1) to compound (I-2).

In addition, compound (I-2) can be converted to (I') or (I-1) by reactions such as the esterification of carboxyl group at the 2 position of compound (I-2) or the amidation of carboxyl group at the 2 position of compound (I-2). These reactions are described below.

The esterification of carboxyl group can be achieved, for example, by the following procedures:

(1) The starting compound (I-2) is reacted with a diazoalkane such as diazomethane, phenyldiazomethane or diphenyldiazomethane in a solvent such as tetrahydrofuran, dioxane, ethyl acetate or acetonitrile at about 0° C. to its refluxing temperature for about 2 minutes to 2 hours.

(2) An alkali metal salt of the starting compound (I-2) is reacted with an activated alkyl halide such as methyl iodide, benzyl bromide, p-nitro-benzyl bromide, m-phenoxybenzyl bromide, p-t-butylbenzyl bromide and pivaloyloxymethyl chloride. As to suitable reaction conditions, it is recommended that the reaction be carried out at about 0° to 60° C. for about 2 minutes to 4 hours using a solvent such as N,N-dimethylformamide, N,N-dimethylacetamide or hexamethylphosphoramide. The coexistence of triethylamine etc. in this reaction mixture does not interfere with the reaction.

(3) The starting compound is reacted with an alcohol represented by the formula $R^{44}$—OH or $R^{44'}$—OH (In these formulae, $R^{44}$ and $R^{44'}$ have the same meanings as defined above), such as methanol, ethanol or benzyl alcohol. This reaction is carried out in the presence of a carbodiimide condensing agent such as DCC. Reaction temperature is about 0° C. to the refluxing temperature, and reaction time is about 15 minutes to 18 hours. Solvents which can be used include chloroform, dichloromethane and dichloroethane.

(4) An acid anhydride of the starting compound (I-2), obtained by reacting the starting compound with an acid chloride such as ethyl chlorocarbonate or benzyl chlorocarbonate is reacted with an alcohol such as any of the alcohols mentioned in (3) above under the reaction conditions described in (3) above. This anhydride is obtained by reacting the starting compound with an acid chloride in a solvent such as tetrahydrofuran or dichloromethane at 25° C. to the refluxing temperature for about 15 minutes to 10 hours.

(5) The starting compound is reacted with a silylating agent such as trimethylsilyl chloride, t-butyl-dimethylsilyl chloride or triethylamine in a solvent such as dichloromethane, chloroform or tetrahydrofuran at about 0° C. to the refluxing temperature for about 15 minutes to 16 hours.

The amidation of carboxyl group is achieved by reacting an acid anhydride of the starting compound (I-2) synthesized from the starting compound (I-2) using an acid chloride such as ethyl chlorocarbonate, benzyl chlorocarbonate or pivaleic chloride or acid anhydride such as acetic anhydride or trifluoroacetic anhydride with either ammonia or a selected amine such as the above-mentioned alkyl-, dialkyl-, aralkyl- or heterocyclic amine.

The amidation of carboxyl group can also be carried out by reacting the compound (I-2) having the carboxyl group with one of the above-mentioned amine compounds in the presence of a condensing agent such as DCC or N-3-dimethylaminopropyl-N-ethylcarbodiimide.

The above reaction is carried out in a solvent such as dichloromethane, tetrahydrofuran or N,N-dimethylformamide at about 0° C. to the refluxing temperature for about 15 minutes to 16 hours.

The compound (I) wherein $R^2$ is methoxy can also be produced by the methoxylation of the compound (I') wherein $R^2$ is hydrogen.

To said methoxylation, the methoxylation methods with regard to the 6- or 7-position used in the fields of penicillin and cephalosporin are applicable. The methoxylation of penicillin or cephalosporin is described in detail, for example, by E. M. Gordon, R. B. Sykes et al. in the "Chemistry and Biology of β-Lactam Antibiotics", Vol. 1, p. 199 (1982), published by Academic Press, where descriptions are presented of the methods via a (1) diazo intermediate, (2) acylimine intermediate, (3) keteneimine or related imine intermediate, (4) quinoidoimine intermediate, (5) sulfenimine intermediate, (6) enimine intermediate etc. Any of these methods permits the production of the desired compound; the method using an acylimine intermediate is described in detail below as a representative example of methoxylation.

The said reaction of methoxylation is carried out by reacting the starting compound (I') wherein $R^2$ is hydrogen to be methoxylated with both an alkali metal salt of methanol and a halogenating agent in the presence of methanol. Alkali metal salts of methanol which can be used include lithium methoxide, sodium mehtoxide and potassium methoxide. Halogenating agents which can be used include t-butyl hypochloride, N-chlorosuccinimide, N-bromosuccinimide, N-chloroacetamide, N-bromo-acetamide, N-chlorobenzenesulfonamide, chlorine and bromine. This reaction is carried out in a solvent; solvents which can be used include tetrahydrofuran, dioxane, dichloromethane, chloroform, acetonitrile, methanol and N,N-dimethylformamide. In this reaction, the starting compound is either dissolved or suspended in a solvent as mentioned above, and to the resulting solution or suspension an alkali metal salt of methanol, methanol and a halogenating agent are added to allow the reaction to go on. It is preferable that methanol be used in not less than 1 equivalents to the starting compound, an alkali metal salt of methanol be used in about 1 to 3.5 equivalents to the starting compound, and a halogenating agent be used in about 1 to 2 eqivalents to the starting compound. The reaction goes on at about −80° to 30° C., and it is stopped by acidizing the reaction system. Acids which are suitable for stopping the reaction include formic acid, acetic acid and trichloroacetic acid. After the completion of the reaction, the excess halogenating agent is removed by treatment with a reducing agent such as sodium thiosulfate or a trialkyl ester of phosphorous acid.

The compound (I') wherein $R^2$ is formylamino can also be produced by the formylamination of the compound (I') wherein $R^2$ is hydrogen.

The formylamination is carried out by converting the compound (I') wherein $R^2$ is hydrogen to an imine derivative represented by the general formula:

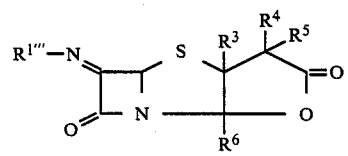

wherein $R^{1''''}$ represents the moiety other than nitrogen of the organic residue bonded via the nitrogen; $R^3$, $R^4$, $R^5$ and $R^6$ are of the same meanings as defined above, and reacting this imine compound with a nucleophilic derivative of formamide represented by the formula:

wherein W and W' each represent hydrogen, silyl* optionally substituted by such substituents as those mentioned above for silyl* in $R^1$, stannyl or phosphoryl, whether identical or not. Of such nucleophilic derivatives of formamide, N,N-bis (trimethylsilyl) formamide is especially suitable. The latter reaction, i.e. the formylamidation reaction with the nucleophilic derivative of formamide is usually carried out in a solvent under an inert atmosphere of nitrogen, argon or the like. Reaction temperature is about $-100°$ to $-20°$ C., preferably about $-80°$ to $-50°$ C.; reaction time is about 10 minutes to 8 hours, preferably about 15 minutes to 2 hours. Any solvent can be used, as long as it is favorably an aprotic solvent; such solvents include tetrahydrofuran, N,N-dimethylformamide, hexamethylphosphoramide and dioxane. When both W and W' are silyl, the desired formamide group can be produced via further hydrolysis with an acid or base following the reaction to remove the remaining silyl*. The starting imine compound can be produced using the same procedure as described in the above-mentioned reference of methoxylation by E. M. Gordon et al.

The desired compound thus obtained can be isolated and purified by a per se known means such as concentration, pH adjustment, phase transfer, solvent extraction, lyophilization, crystallization, fractional distillation and chromatography.

Since having at least 2 asymmetric carbon atoms in its base skeleton, the desired compound (I) of the present invention occurs theoretically in at least 4 different stereoisomers; these isomers and their mixtures are also involved in the present invention. Stereoisomers also occur in cases where the group represented by $R^1$ contains at least 1 asymmetric carbon atom and in cases where the group represented by the formula —COOR$^{44}$ wherein $R^{44}$ is of the same meaning as defined above at the 2 position of the base skeleton contains at least 1 asymmetric carbon atoms; these isomers and their mixtures are also involved in the present invention. In cases where these isomers are produced in mixtures in the above reaction, respective isomers can be isolated via routine methods such as various chromatographies and recrystallization.

When obtained in the free form, the compound of the present invention may be allowed to form a salt using a routine means. In addition, the compound of the present invention, when obtained in the form of a salt, may be converted to the free form using a routine means.

The desired compound in some cases forms an intramolecular salt; such salts are also involved in the present invention.

The stereoisomers of the desired compound, either singly or in mixture, can be used as pharmaceuticals.

The compound (II), which is used as a starting compound in the method of the present invention, can be produced by, for example, the method described below. In the formulae shown below, $R^1$, $R^2$, $R^3$, $R^4$, $R^5$ and $R^6$ are as defined above.

Production method for the compound (II)

This process is a production process for the compound (II), in which the compound (IV) represented by the formula:

wherein $R^{49}$ represents hydrogen or a metal ion of mercury, silver, thallium or the like; $R^{50}$ represents either hydrogen or a group convertible to hydrogen; $R^{1'}$ and $R^2$ are of the same meanings as defined above is reacted with the compound (V) represented by the formula:

wherein $R^{51}$ and $R^{52}$ respectively represent a leaving group and either a carboxyl group or a group derivable therefrom e.g. carboxyl group; $R^3$, $R_4$, $R^5$ and $R^6$ are of the same meanings as defined above, an ester or a salt therreof, to obtain the compound (VI) represented by the formula:

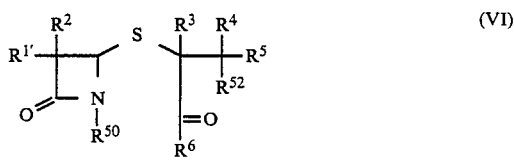

wherein $R^{1'}$, $R^2$, $R_3$, $R_4$, $R^5$, $R^6$, $R^{50}$ and $R^{52}$ are of the same meanings as defined above, an ester or a salt thereof whose $R^{52}$, when it is not a carboxylic group, is then converted to a carboxyl group and whose $R^{50}$, when it is not hydrogen, is then converted to hydrogen or whose $R^{1'}$ and $R^6$, if necessary, are then subjected to the above-mentioned conversion reaction such as deprotection to produce the compound (II). As examples for $R^{49}$ in the above formula (IV), mention may be made of hydrogen and ions of metals such as mercury, silver and thallium. As examples for $R^{50}$ in the above formulae (IV) and (VI), mention may be made of hydrogen and, as a group convertible to hydrogen, silyl groups such as trimethylsilyl, t-butyldimethylsilyl and diphenylmethylsilyl; and isopropylideneacetic acid ester groups represented by the formula

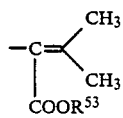

wherein $R^{53}$ represents an organic residue such as those mentioned above for R' bonded via carbon. Leaving groups represented by $R^{51}$ in the above formula (V) include halogens (e.g. bromine and chlorine), sulfonyloxys having a substituent such as alkyl or aryl (as examples of alkyls and aryls, mention may be made of the substituents similar to those for $R^1$ mentioned above) (as specific examples of such sulfonyloxys, mention may be made of p-toluenesulfonyloxy, p-nitrophenylsulfonyloxy and methanesulfonyloxy) and disubstituted phosphoryloxys (e.g. diphenylphosphoryloxy and diethylphosphoryloxy).

Groups which can be represented by $R^{52}$ in the above formulae (V) and (VI) include carboxyl group and caboxylic acid esters such as t-butyloxycarbonyl, benzyloxycarbonyl, 4-nitrobenzyloxycarbonyl, diphenylmethyloxycarbonyl and aryloxycarbonyl.

The process for producing the compound (VI), an ester or a salt, thereof by reaction between the compound (IV) and the compound (V), an ester or a salt, thereof may be carried out in a solvent in the presence of a base such as triethylamine, diisopropylamine, pyridine or 4-dimethylaminopyridine, as long as it does not interfere with the reaction. Solvents which can be used include dichloromethane, chloroform, tetrahydrofuran, dioxane, benzene, toluene, acetonitrile, N,N-dimethylacetamide, N,N-dimethylformamide and hexamethylphosphoramide. Reaction temperature is usually about −20° to 100° C., and reaction time is about 10 minutes to 50 hours.

When the $R^{50}$ of the compound (VI) is a silyl group, the reaction of converting the compound (VI), an ester or a salt thereof, to the compound (II), an ester or a salt thereof, can be conducted by reacting the compound (VI), an ester or a salt thereof, with an acid (e.g. hydrochloric acid, acetic acid, formic acid and trifluoroacetic acid) or fluoride anion (e.g. tetra-n-butylammonium fluoride, potassium fluoride and tritylboron tetrafluoride) in a solvent. When $R^{50}$ is an isopropylidene acetate group, the reaction is carried out by reacting the compound (VI) with an oxidizing agent (e.g. postassium permanganate and ozone). In cases where the $R^{52}$ of the compound (VI) is a group derivable from carboxyl group as mentioned above or where the group represented by $R^{1'}$ in the compound (VI) is protected by a silyl group which may be substituted by a group such as an alkyl group), the compound (VI) an ester or salt thereof can be converted to the compound (II) an ester or salt thereof by subjecting the compound (VI) an ester or salt thereof to such a deprotection reaction as mentioned as a conversion reaction for $R^{1'}$ and $R^6$ described above in relation to the method of producing the compound (I) an ester or salt thereof from the compound (I'). For example, when $R^{52}$ is either t-butyloxycarbonyl or diphenylmethyloxycarbonyl, the reaction is carried out by reacting the compound (VI) an ester or salt thereof with trifluoroacetic acid in the presence of anisole. When $R^{52}$ is either benzyloxycarbonyl or 4-nitrobenzyloxycarbonyl, the reaction is carried out by catalytic reaction. The above reactions for conversion can be carried out according to the conventional manner.

The starting compound (IV) can be produced by various well-known methods or those analogous thereto. For example, various compounds (IV) of the formula are known in the references shown below, and the compound (IV) can be obtained in accordance with the known methods or methods analogous thereto.

(1) Y. Hamashima et al.: Recent Advances in the Chemistry of β-lactam Antibiotics, No. 28, pp. 243–251 (1977).

(2) R. D. G. Cooper and G. A. Koppel: Chemistry and Biology of β-lactam Antibiotics, vol. 1, pp. 1–92 and vol. 2, pp. 315–360 (1982).

(3) K. Hirai et al.: Tetrahedron Letters, vol. 23, p. 4021 (1982).

(4) H. Yanagisawa et al.: Tetrahedron Letters, vol., 24, p. 1037 (1983).

Thus, the compound (IV) (wherein $R^2$ hydrogen and $R^{1'}$ is an organic residue bonded via N) can also be produced in accordance with, e.g. the following reaction formula:

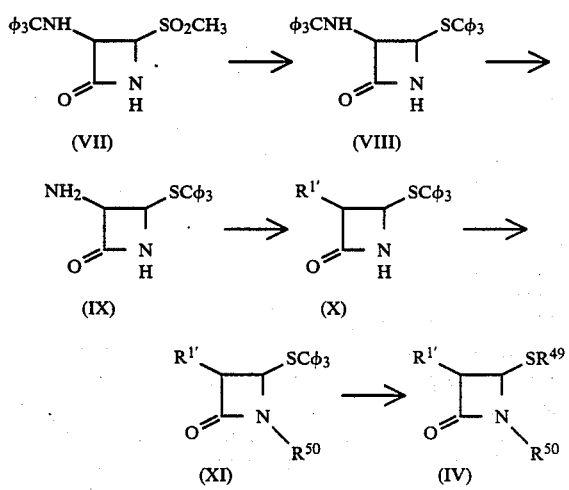

wherein $\phi$ represents a phenyl group; the other symbols are of the same meanings as defined above.

The reaction by which the compound (VIII) is produced from the compound (VII) [E. G. Brain et al.; J. Chem. Soc. Perkin, 447 (1976)]is carried out by reacting the compound (VII) with trityl mercaptan in a solvent in the presence of a base. Bases which can be used include organic amines such as triethylamine and tri-n-butylamine; hydrides, hydroxides and carbonates of alkali metals such as lithium, sodium, potassium and cesium. Any solvent can be used, as long as it does not interfere with the reaction. As specific examples of solvents which can be used, mention may be made of water, tetrahydrofuran, dioxane, acetonitrile, N,N-dimethylformamide, N,N-dimethylacetamide, hexamethylphosphoramide and their mixtures. Reaction time is about 5 minutes to 30 hours, and reaction temperature is usually about −20° to 100° C.

The reaction of converting the compound (VIII) to the compound (IX) is carried out by reacting the compound (VIII) with an acid in a solvent. Acids which can be used include p-toluenesulfonic acid, hydrochloric acid and formic acid. Any solvent can be used, as long as it does not interfere with the reaction. As specific examples of solvents which can be used, mention may be made of water, tetrahydrofuran, dioxane, acetonitrile, acetone, dichloromethane, ethyl acetate and their mixtures.

The reaction of converting the compound (IX) to the compound (X) can be carried out in accordance with the reaction of introducing a protective group to either the amino group at the 6 position of penicillin or the amino group at the 7 position of cephalosporin or the reaction of acylating these amino groups. Specifically, this reaction can be carried out in accordance with such an acylation method as described as a conversion reaction for $R^{1'}$ in relation to the production of the compound (I') to the compound (I).

When $R^{50}$ in the above formulae is a group convertible to hydrogen, the reaction of converting the compound (X) to the compound (XI) is carried out by reacting the compound (X) with a silylating agent such as trimethylsilyl chloride, t-butyldimethylsilyl chloride, t-butyldimethylsilyl trifurate and diphenylmethylsilyl chloride in a solvent in the presence of a base. As such a solvent, any solvent can be used, as long as it does not interfere with the reaction. As specific examples of solvents which can be used, mention may be made of dichloromethane, ethyl acetate, benzene, chloroform, N,N-dimethylformamide and N,N-dimethyl-acetamide. Bases which can be used include organic amines such as triethylamine, tri-n-butylamine, N,N-dimethylaminopyridine, imidazole and methylimidazole. Reaction time is about 5 minutes to 30 hours, and reaction temperature is usually about −20° to 100° C.

The reaction of converting the compound (XI) to the compound (IV) is carried out by adding mercuric chloride, mercuric nitrate, silver nitrate, thallium nitrate or the like to compound (XI) in a solvent in the presence of a metal ion of mercury, silver, thallium or the like. The compound (IV) wherein $R^{49}$ is hydrogen can be obtained by further reacting thus obtained product with hydrogen sulfide. The compound (IV) wherein $R^{50}$ is hydrogen can be obtained by further reacting the product with an inorganic acid such as hydrochloric acid or organic acid such as acetic acid, formic acid or trifluoroacetic acid. As specific examples of solvents for the reaction, mention may be made of methanol, ethanol, tetrahydrofuran, dichloromethane, ethyl acetate, chloroform, N,N-dimethylacetamide and N,N-dimethylformamide. Reaction temperature is usually about −78° to 50° C., but the reaction may be carried out beyond this temperature range.

The starting compound (V) wherein $R^{52}$ is a group derivable from carboxyl group can be produced by, for example, the following process:

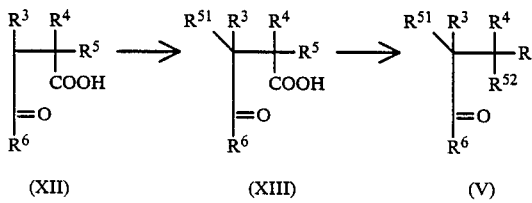

wherein the respective symbols are of the same meanings as defined above. The compound (XII) is converted to the compound (XIII) by allowing a halogenating agent such as bromine or chlorine to act on the compound (XII) in a solvent. The compound (XIII) thus obtained can be converted to the compound (V) in accordance with a method of carboxylic acid esterification well-known in the peptide, penicillin or a phlosporin field, among others, preferably the method of esterification described above in relation to the reaction of converting $R^{1'}$ and/or $R^6$ to obtain the compound (I) from the compound (I'). Solvents which can be used for the reaction of converting the compound (XII) to the compound (XIII) include acetic acid, chloroform, dichloromethane and carbon tetrachloride. The reaction is usually carried out at a reaction temperature of about −20° to 100° C.

The conversion of the compound (XIII) to the compound (V) can be achieved by allowing methanol, ethanol or benzyl alcohol to act on the compound (XIII) in the presence of an acid such as hydrochloric acid or sulfuric acid, allowing diazomethane, diphenyldiazomethane or the like to act on the compound (XIII), by allowing isobutene to act on the compound (XIII) in the presence of, for example, sulfuric acid, or by another method so that the compound (XIII) is esterified to the compound (V).

The compound (XII), which is used as the starting compound is produced by, for example, the method described below. In the formulae shown below, $R^3$, $R^4$, $R^5$ and $R^6$ are as defined above.

Compound (XIV)→Compound (XII):

This process is a process of producing the compound (XII), i.e. a monoester, by selectively esterifying the carboxyl group at the 1st position alone of the 2 carboxyl groups contained in the compound represented by the formula:

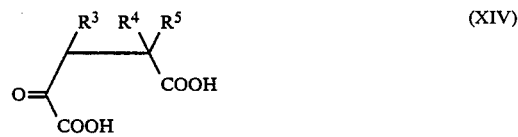

This reaction is carried out by reacting the compound (XIV) with an equivalent or slightly excess amount of an esterifying agent in a solvent in the presence of an equivalent of a base. Esterifying agents which can be used here include halides such as methyl iodide, benzyl bromide, p-nitrobenzyl bromide, m-phenoxybenzyl bromide p-t-butylbenzyl bromide, diphenyl bromide and pivaloyloxymethyl chloride; and dialkyl sulfates such as dimethyl sulfate and diethyl sulfate. Bases which can be used include organic amines such as diisopropylmaine, dicyclohexylamine, cyclohexylisopropylamine, triethylamine, tripropylamine, tri-n-butylamine, diisopropylethylamine, DABCO, DBU, N-methylmorpholine, N-methylpiperidine, N-methylpyrrolidine, 3,4-dihydro-2H-pyrido [1,2-a] pyrimidine-2-one, 4-dimethylaminopyridine, pyridine, lutidine and Y-collidine; and hydrides, hydroxides and carbonates of alkali metals such as lithium, sodium, potassium and cesium.

Solvents which can be used include N,N-dimethylformamide, N,N-dimethylacetamide, hexamethylphosphoramide, dimethyl sulfoxide, dichloromethane, acetonitrile and tetrahydrofuran. Reaction temperature is usually about −20° to 100° C., and reaction time is about 5 minutes to 30 hours.

Compound(XIV)→Compound(XV)→Compound(XVI)→Compound(XII):

This process is a process of producing the compound (XII) by reacting the compound (XIV) with benzyl carbamate to produce the compound (XV) as represented by the formula:

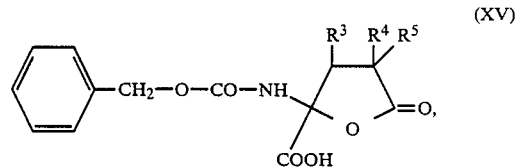

followed by subjecting the compound (XV) thus obtained to an esterification reaction to produce the compound (XVI) as represented by the formula:

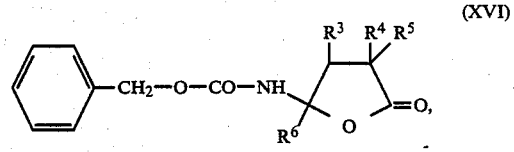

and then treating the thus-obtained compound (XVI) with an acid. This process is carried out by reacting the compound (XIV) with about an equivalent to slightly excess amount of benzyl carbamate via heating under reduced pressure usually in the absence of solvent. The degree of pressure reduction is about 0.1 to 50 mmHg. Reaction temperature is usually about 50° to 120° C., and reaction time is about 30 minutes to 20 hours. The compound (XV) is then converted to the compound (XVI) via an esterification reaction. The said esterification reaction can be carried out using such conditions as those for the esterification of the compound (XIV) to the compound (XII) described above. The esterification may be conducted using a diazoalkane such as diazomethane or for example methanol, ethanol or benzyl alcohol in the presence of a carbodiimide condensing agent such as DCC. A suitable esterification method is selected according to the type of the desired ester. In this case, an ester which is relatively stable to acid is preferably selected because an acid is used in the next reaction. The compound (XVI) is converted to the compound (XII) by bringing the compound (XVI) into contact with an acid. Acids which can be used for this purpose include hydrochloric acid, sulfuric acid, hydrobromic acid, perchloric acid, periodic acid, formic acid, trifluoroacetic acid and p-toluenesulfonic acid; these acids are used in an excess amount either singly or in combination. Of these acids, a combination of hydrobromic acid and acetic acid is suitable. Reaction temperature is about 0° to 50° C., and reaction time is about 15 minutes to 5 hours.

Compound(XIV)→Compound(XVII)→Compound(XII):

This process is a process of producing the compound (XII) by reacting the compound (XIV) with a halogenocarbonate to produce the compound (XVII) represented by the formula:

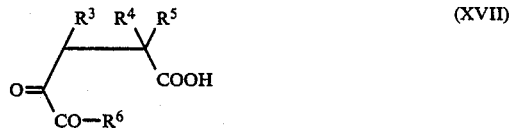

then decarboxylating the compound (XVII) thus obtained. An example of the synthesis of 1-ethyl 2-oxoglutrate by the reaction between 2-oxoglutaric acid [the compound (XIV) wherein $R^3=R^4=R^5=H$] and ethyl chlorocarbonate followed by decarboxylation is already known in literature [J. M. Domagala; Tetrahedron Letters, vol. 21, p. 4997 (1980)]. According to this reaction, the compound (XII) can be produced by reacting the compound (XIV) with a halogenocarbonate in a solvent in the presence of a base, and then decarboxylating the product thus obtained. As specific examples of halogenocarbonates, mention may be made of methyl chlorocarbonate, ethyl chlorocarbonate, benzyl chlorocarbonate and 2,2,2-trichloroethyl chlorocarbonate. Bases which can be used for this reaction include organic amines such as triethylamine, tripropylamine, tri-n-butylamine, diisopropylethylamine, triethylenediamine, DABCO, DBU, N-methylmorpholine, N-methylpiperidine, N-methylpyrrolidine 3,4-dihydro-2H-pyrido [1,2-a] pyrimidine-2-one, 4-dimethylaminopyridine, pyridine, lutidine and γ-collidine; alkali metals such as lithium, sodium, potassium and cesium; alkaline earth metals such as magnesium and calcium; and hydrides, hydroxides, carbonates and alcoholates to these metals. Solvents which can be used include ordinary solvents such as dichloromethane, chloroform, tetrahydrofuran, dioxane, benzene, toluene, acetonitrile, dimethylacetamide and dimethylformamide. In this reaction, a base and a halogenocarbonate may be both used in an amount of 1 equivalent relative to compound (XIV). Reaction temperature is usually about −30° to 60° C., and reaction time is about 1 minute to 2 hours. It is not necessary to specifically isolate the compound (XVII); the decarboxylation reaction goes on under the above-mentioned reaction conditions, and the compound (XII) can be directly obtained.

Compound(XIV)→Compound(XVIII)→Compound(XII):

This process is a process of producing the compound (XII) by allowing a dehydrating agent to act on the compound (XIV) to obtain the acid anhydride compound (XVIII) as represented by the formula:

then reacting the compound (XVIII) thus obtained with an alcohol. Dehydrating agents which can be used for this reaction include halogen compounds such as phosphorus oxychloride, thionyl chloride and chlorosulfonic acid; acid anhydrides of lower fatty acid such as acetic anhydride and trifluoroacetic anhydride; acid halides such as acetyl chloride; imidazole derivatives such as N,N′-carbonylimidazole and N-trifluoroacetylimidazole; and DCC. When an acid halide as mentioned above is used, an organic base such as pyridine or triethylamine may be used in combination. This reaction is carried out using a dehydrating agent in about an equivalent to an excess amount to the compound (XIV) either in a solvent or, when the dehydrating agent is a liquid, using it for the dual purposes of dehydrating agent and solvent. Solvents which can be used include dichloromethane, benzene, toluene and acetonitrile. Reaction temperature is usually about 0° to 100° C., and reaction time is about 15 minutes to 30 hours. The compound (XII) is then obtained by reacting the compound (XVIII) with about an equivalent to an excess amount of an alcohol. For this reaction, an alcohol represented by the formula $R^{44}OH$ or $R^{44'}OH$ wherein $R^{44'}$ are of the same meanings as defined above. As examples of such alcohols, mention may be made of methyl alcohol, ethyl alcohol, benzyl alcohol, p-nitrobenzyl alcohol and t-butyl alcohol. In this reaction, a catalyst such as sulfuric acid, p-toluenesulfonic acid, zinc chloride, sodium acetate, pyridine, 4-dimethylaminopyridine, 4-pyrrolidinopyridine, triethylamine or calcium carbide may be used. Reaction temperature is about 0° to 100° C., and reaction time is about 10 minutes to 4 days.

Compound(XIV)→Compound(XIX)→Compound(XX)→Compound(XXI)→Compound(XII):

This process is a process of producing the compound (XII) by diesterifying the compound (XIV) to obtain the compound (XIX) as represented by the formula:

then selectively hydrolyzing the ester group at the 1 position alone to convert the compound (XIX) to the compound (XX) as represented by the formula:

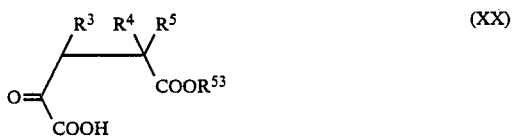

then introducing an ester group different from the ester group at the 5 position to the carboxyl group at the 1 position to obtain the compound (XXI) as represented by the formula:

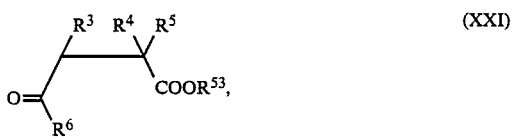

followed by selectively converting the ester group at the 5 position alone to a carboxyl group to produce the compound (XII). As examples of groups for $R^{53}$ in the above formulae (XIX), (XX) and (XXI), mention may be made of alkyl groups such as methyl and ethyl; and aralkyl groups such as benzyl, p-bromobenzyl p-nitrobenzyl.

The reaction of converting the compound (XIV) to the compound (XIX) is carried out by the method described above in relation to the method of producing the compound (XII) from the compound (XIV) using both an esterifying agent in about 2 equivalents to an excess amount relative to compound (XIV) and a base respectively. The hydrolysis of the compound (XIX) to the compound (XX) is usually carried out in a solvent using a base such as a hydroxide, carbonate or alcoholate of an alkaline metal such as llithium, sodium, potassium or cesium. As solvents, use is made of water, methanol, ethanol, tetrahydrofuran, dimethylsulfoxide and the like, which are used either singly or in combination. This hydrolysis reaction is carried out using a base usually in an amount of an equivalent relative to the compound (XIX). Reaction temperature is usually about 0° to 80° C., and reaction time is about 10 minutes to 20 hours. The reaction of esterifying the compound (XX) to the compound (XXI) can be carried out in accordance with the method described above in relation to the method of producing the copound (XII) from the compound (XIV). The compound (XX) may be further reacted with isobutene in the presence of an acid catalyst to produce its t-butyl ester. When the ester group at the 1st position is stable to base while the ester group at the 5th position is not stable to base (e.g. in cases where $R^6$=t-butyl, $R^{53}$=methyl), the reaction of converting the compound (XXI) to the compound (XII) is achieved by applying the above-mentioned method of alkali hydrolysis of the compound (XIX) to the compound (XX). When the ester group at the 1st position is table to the reduction conditions while the ester group at the 5th position is not stable to the reduction conditions (e.g. in case where $R^6$=t-butyl, $R^{53}$=benzyl), a mono-ester [Compound (XII)] can be selectively obtained by a reducing method. Reducing methods which can be employed include methods of catalytic reduction using a metal catalyst such as palladium carbon, palladium black, palladium barium carbonate, platinum oxide, platinum black or Raney nickel; and methods of reduction using an acid such as hydrochloric acid, formic acid or acetic acid together with a metal such as zinc, iron, chromium. The method by reduction is usually carried out in a solvent; solvents which can be used include water, methanol, ethanol, ethyl acetate, acetone and the above-mentioned acids. Reaction temperature is usually about 0° to 60° C., and reaction time is about 10 minutes to 20 hours Compound (XXII)→Compound (XXIV)→Compound (XXV)→Compound (XXI)→Compound (XII):

This process is a process of producing the compound (XII) by esterifying the compound (XXII) as represented by the formula:

to produce the compound (XXIII) are represented by the formula:

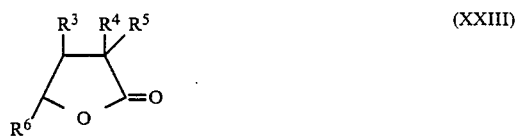

then hydrolyzing the compound (XXIII) thus obtained to yield the compound (XXIV) as represented by the formula:

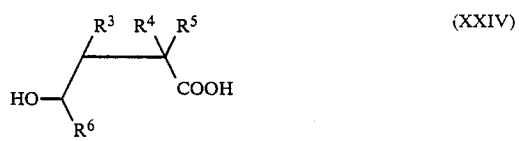

further esterifying the compound (XXIV) thus obtained to convert to the compound (XXV) as represented by the formula:

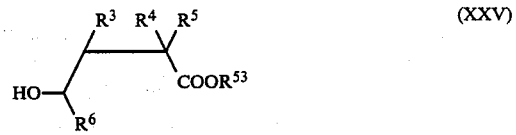

then oxidizing the hydroxyl group of the compound (XXV) thus obtained to produce the compound (XXI) (which is mentioned above), and subjecting the compound (XXI) thus obtained to the above-mentioned reaction of converting the compound (XXI) to the compound (XII).

The starting compound (XXII) wherein $R^3=R^4=R^5=H$ is already known in literature, and it can be easily synthesized from glutamic acid [refer to M. Taniguchi et al.; Tetrahedron, 30, 3547 (1974)]. Compounds represented by the formula (XXII) wherein $R^3$ to $R^5$ are each a substituent defined above can be synthesized in accordance with this method. The esterification of the compound (XXII) to the compound (XXIII) to be achieved in the same manner as described above in relation to the method of producing the compound (XII) to the compound (XIV). The compound (XXII) may be allowed to form an adduct of alkene such as isobutene in the presence of a catalyst (substances which can be used as catalysts include acids such as sulfuric acid and hydrochloric acid and boron trifluoride) to produce a t-alkyl ester; this reaction is usually carried out in a solvent. Solvents which can be used include dichloromethane, chloroform, dioxane, diethyl ether, tetrahydrofuran and benzene. This alkene addition is achieved, for example, by reacting the compound (XXII) with an excess amount of isobutene in a tight container at about 0° to 50° C. for about 5 hours to several days. To the alkali hydrolysis of the compound (XXIII) to the compound (XXIV) is applicable the method described above in relation to the method of producing the compound (XX) from the compound (XIX). In this reaction, it is necessary to select a type of the compound (XXIII) whose ester group is relatively stable to alkali (e.g. $R^6$=t-butyloxycarbonyl). The esterification of the compound (XXIV) to the compound (XXV) can be carried out in the same manner as the abovementioned method of converting the compound (XV) to the compound (XVI). The reaction of oxidizing the compound (XXV) to the compound (XXI) is carried out by reacting the compound (XXV) with an oxidizing agent in a solvent. Oxidizing agents which can be used include potassium permanganate, manganese dioxide, dimethylsulfoxide (DMSO)-DCC, DMSO-acetic anhydride, DMSO-oxalyl chloride and DMSO-phosphorus pentaoxide. Solvents which can be used include dichloromethane, chloroform, acetonitrile, ethyl acetate, benzene, toluene, DMSO, N,N-dimethylformamide, acetone and ether. In this reaction, an oxidizing agent is usually used in a nearly equivalent to an excess amount relative to the compound (XXV). Reaction temperature is about −80° to 60° C., and reaction time is about 10 minutes to 30 hours.

The compound (XII) wherein $R^6$ is an amidated carboxyl group can be produced by applying the above-mentioned method of amidating carboxylic acid to the treatment of the above compound (XX) to produce the compound (XXI), followed by conducting the method in accordance with the method described above in relation to the method of producing the compound (XII) from the compound (XXI).

The compound (XIV), used as a starting compound for the present invention, can be produced by various methods already reported. For example, the compound (XIV) is per se known in the references shown below, and the compound (XIV) can be produced in accordance with the methods described therein or the methods analogous thereto.

(1) Organic Synthesis, Collective vol. 3, 510 (1955)
(2) M. E. E. Blaise et al.: Bulletin de la Society Chimique de France, 9, 458 (1911)
(3) W. H. Perkin et al.: Journal of the Chemical Society, 79, 729 (1901)
(4) J. C. Bardham: Journal of the Chemical Society, 2591 (1928)
(5) W. N. Haworth et al.: Journal of the Chemical Society, 105, 1342 (1914)
(6) F. C. Hartman: Biochemistry, 20, 894 (1981)
(7) G. Hesse et al.: Annalen der Chemie, 697, 62(1966)

The compound (XIV) can be produced in accordance with, for example, the following reaction formula:

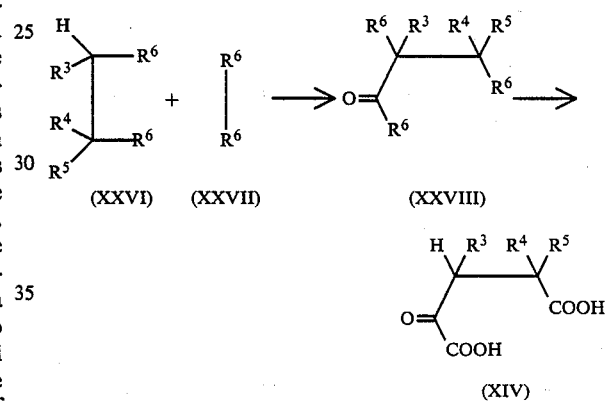

In the above formula, $R^3$, $R^4$, $R^5$ and $R^6$ are of the same meanings as defined above.

The conversion of the compoud (XXVI) to the compound (XXVIII) is a reaction which is well known as what is called Claisen condensation, where the compound (XXVI) and the compound (XXVII) are condensed in a solvent in the presence of a base. Bases which can be used for this reaction include alkali metals such as lithium, sodium and potassium; alkaline earth metals such as magnesium and calcium; hydrides, alcoholates, amide and alkyl salts of these metals; and quaternary ammonium. Solvents which can be used include alcohols such as methanol and ethanol (in cases where an alcoholate is used, the alcohol for the alcoholate is the same with the alcohol for the alkoxy group of the ester), either, tetrahydrofuran, dioxane, N,N-dimethylformamide, 1,2-dimethoxyethane, dichloromethane, benzene and toluene.

Reaction temperature is usually about 0° to 80° C., and reaction is about 10 minutes to 10 hours.

The conversion of the compound (XXVIII) to the compound (XIV) is a process of producing the compound (XIV) by treating the compound (XXVIII) with an acid, alkali or reducing agent. This reaction can be carried out in accordance with, for example, the abovementioned method of producing the compound (XX) from the compound (XIX) or of producing the compound (XII) from the compound (XXI).

Production method for the compound (III)

This process is a process of producing the compound (III) by reacting the compound (VI) to obtain the compound as represented by the formula:

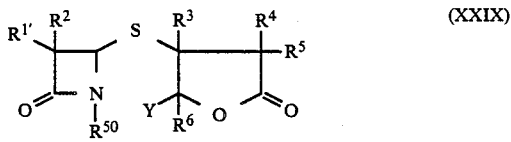

wherein $R^{1'}$, $R^2$, $R^3$, $R^4$, $R^5$, $R^6$, $R^{50}$ and Y are of the same meanings as defined above, and when the $R^{50}$ of the compound thus obtained is a group convertible to hydrogen, by converting the group represented by $R^{50}$ to hydrogen.

This reaction is usually carried out by reacting the compound (VI) with an activating agent in the presence or absence of solvent. Activating agents which can be used for this reaction include the carboxyl group activating agents described and exemplified above in relation to the reaction of converting the compound (II) to the compound (I'); this reaction is carried out by treating the compound (VI) with an activating agent as mentioned above in a nearly equivalent to an excess amount relative to the said compound (VI) either in a solvent or in the absence of solvent. This reaction may be carried out in the presence of a base such as triethylamine, diisopropylethylamine, pyridine or 4-dimethylaminopyridine, as long as it does not interfere with the reaction. Solvents which can be used include dichloromethane, chloroform, carbon tetrachloride, 1,2-dichloroethane, N,N-dimethylformamide, N,N-dimethylacetamide, acetonitrile, tetrahydrofuran, benzene and toluene. Reaction temperature is usually about −20° to 100° C., and reaction time is about 30 minutes to 50 hours. When the $R^{50}$ of the compound (XXIX) is a group convertible to hydrogen among the definition for $R^{50}$, the relevant compound (XXIX) is converted to the compound (III) in accordance with the method of producing the compound (II) from the compound (VI). The respective intermediate compounds thus obtained can be isolated by per se known means such as concentration, liquid property conversion, re-dissolution solvent extraction, lyophilization, crystallization, recrystallization, fractional distillation and chromatography.

The compounds (II) and (III) thus obtained are novel substances, and they are useful as starting compounds for the production of, for example, the compound (I').

As the esters and salts of intermediate compounds (II), (III) (V) and (VI), there are mentioned, for example, the esters mentioned above with regard to the group -COOR$^{44}$ and the salts of the compound (I) respectively.

The compounds (I) obtained as above, their esters or their salts are useful as pharmaceuticals, possessing antibacterial activity on, for example, some species of gram-positive and gram-negative bacteria. The antibacterial spectra of typical compounds among the compounds (I) against various microorganisms are as shown in Table 1 below.

TABLE 1

| Micro-organism | Minimum growth inhibitory concentration (Note 1)(μg/ml) | (Note 2) Compound (I-2) | Compound (I-4) | Compound (I-7) | Penicillin -G |
|---|---|---|---|---|---|
| Staphylococcus aureus | FDA 209P | <0.05 | 0.1 | 1.56 | 0.0125 |
| Micrococcus luteus | IFO 12708 | <0.05 | 0.05 | 0.1 | <0.00625 |
| Bacillus subtilis | NIHJ PCI 219 | <0.05 | 0.025 | 0.2 | <0.00625 |
| Bacillus cereus | FDA 5 | 6.25 | 12.5 | 3.13 | 12.5 |
| Escherichia coli | NIHJ JC 2 | 0.78 | 6.25 | 12.5 | 50 |
| Salmonella typhimurium | IFO 12529 | 0.1 | 3.13 | 6.25 | 12.5 |
| Citrobacter freundii | IFO 12681 | 50 | >100 | 50 | >100 |
| Klebsiella pneumoniae | IFO 3317 | 0.1 | 0.78 | 0.1 | 3.13 |
| Serratia marcescens | IFO 12648 | >100 | >100 | 12.5 | >100 |
| Proteus mirabilis | ATCC 21100 | 0.39 | 1.56 | 0.025 | 0.1 |
| Proteus vulgaris | IFO 3988 | 0.39 | 1.56 | 0.025 | 3.13 |
| Proteus morganii | IFO 3168 | 0.2 | 1.56 | 0.2 | >100 |
| Pseudomonas aeruginosa | IFO 3080 | >100 | >100 | >100 | 50 |
| Alcaligenes faecalis | IFO 13111 | 0.78 | 6.25 | 6.25 | 3.13 |
| Acinetobacter calcoaceticus | IFO 13006 | >100 | >100 | >100 | 50 |

(Note 1) Medium composition: 17.5 g Bacto Antibiotic Medium 3 (Difco Laboratories, USA), 50 g Bacto Yeast Extract (Difco Laboratories, USA), 20 g Bacto Agar (Difco Laboratories, USA), 1000 ml distilled water (pH not adjusted). Inoculum concentration: about 10$^6$ CFU/ml (Note 2) The compounds (I-2), (I-4) and (I-7) are the compounds produced in Examples 2, 4 and 7, respectively.

The compounds of the present invention are low in toxicity.

As described above, the compounds of the present invention exhibit antibacterial action on species of gram-positive and gram-negative bacteria, thus can be used as therapeutic drugs or antibacterial drugs for bacterial infections (e.g. respiratory infections, urinary tract infections, suppurativediseases, bile duct infections, intraintestinal infections, gynecological infections and surgical infections) in mammals (e.g. mice, rats, dogs, pigs, bovines and humans) suffering from a bacterial infection.

The compounds of the present invention can be orally administered in combination with a suitable pharmacologically allowable carrier, excipient and diluent in the dose form of, for example, tablet, granule, capsule and drop. They can also be parenterally administered in formulation in the dose form of, for example, an injection prepared via a routine method therefrom with the use of a sterile carrier prepared via a routine method.

The daily dosage of the compounds of the present invention, when they are administered in the form of, for example, injection, is about 2 to 100 mg/Kg, preferably about 5 to 40 mg/Kg, calculated on the basis of the compound (I).

On account of their antibacterial properties, the compounds of this invention may be used as an antiinfective agent or a disinfectant for removing bacteria including the afore-mentioned bacteria from surgical instruments or hospital rooms.

For example, surgical instruments are put for 2 days in an aqueous solution containing 1000 μg/ml of any compound of this invention for the above purpose. However, in the case where esters of this invention are employed for this purpose, the corresponding deesterified are put into use.

In producing the above-mentioned oral pharmaceutical preparations such as tablets, binders (e.g. hydroxypropylcellulose, hydroxypropylmethylcellulose, and macrogol), disintegrating agents (e.g. starch and carboxymethylcellose calcium), excipients) (e.g. lactose and starch), lubricants (e.g. magnesium stearate and talc) and the like may be properly added.

In producing the above-mentioned parenteral pharmaceutical preparations such as injections, isotonicizing agents (e.g. glucose, D-sorbitol, D-mannitol and sodium chloride), preservatives (e.g. benzyl alcohol, chlorobutanol, methyl para-oxybenzoate and propyl para-oxybenzoate), buffering agents (e.g. phosphate buffer solutions and sodium acetate buffer solutions) and the like may be properly added.

The present invention is hereinafter described in more detail with the following examples and reference examples, but these examples are not to be construed as limitations of the present invention, and may be varied as long as they do not deviate from the scope of the present invention.

Unless otherwise stated, elution in column chromatography in Examples and Reference Examples was carried out while observing via TLC (thin layer chromatography). In TLC observation, Merck 60F$_{254}$ was used as the TLC plate; the solvent used as the elution solvent for column chromatography was used as the developing solvent; the UV detector was used for the detection of the desired products. The detection method based on the phenomenon that after a series of treatments of 48% HBr spraying, hydrolysis while heating, ninhydrin reagent spraying and re-heating, thecolor of TLC plate spots corresponding to eluted fractions containing the desired products changes to red to red-purple, was used in combination with the UV detection method to identify the eluted fractions containing the desired products, which were then collected As to developing solvents, figures in parentheses represent mixing ratios of respective mixed solvents by volume. In cases where 2 developing solvents were used, by-products were first eluted and the solvent whose mixing ratio by volume is represented by the figures preceding the arrow in the parenthesis, then the desired product was eluted with the solvent whose mixing ratio by volume is represented by the figures following the arrow in the figure, unless otherwise stated. In purification via column chromatography using Amberlite XAD-2, water and then an aqueous solution of ethanol was used as developing solvents while increasing concentration gradually, unless otherwise mentioned in Examples or Reference Examples.

The Amberlite used was manufactured by Rohm & Haas Co., USA. Unless otherwise stated, Wako-gel C-300 (200 to 300 mesh), manufactured by Wako Pure Chemical Co., Ltd., was used as column packing silica gel, and it was subjected to flash chromatography in accordance with the method described in W. C. Still et al., Journal of Organic Chemistry, 43, 2923 (1978). NMR spectrometry was carried out using tetramethylsilane as internal or external standard and the spectrometers VARIAN EM390 model (90 MHz), VARIAN T60 model (60 MHz), JEOL JNM-GX270 model (270 MHz) or JEOL JNM-GX400 model (400 MHz); every δ value is shown in ppm. Field desorption mass spectrometry (FDMS) and secondary ion mass spectrometery (SIMS) using the Hitachi M-80A model spectrometer were also carried out in some cases. It should be noted that "room temperature" means 0° C. to 40° C. Unless other specified, % figures represent percentages of weight. Figures in parentheses in cases where a mixed solvent was used represent mixing ratios by volume of respective solvents. The symbols used in Examples and Reference Examples have the meanings shown below.

S: singlet
d: doublet
t: triplet
q: quartet
ABq: AB-type quartet
dd: double doublet
m: multiplet
sh: shoulder
br: broad
J; coupling constant
mg: milligram
g: gram
ml: milliliter
μl: microliter
l: liter
ppm: part per million
Hz: Herz
DMSO: dimethyl sulfoxide
D$_2$O: heavy water Reference Example 1

Production of
1-(4-nitrobenzyl)2-oxoglutarate[Compound (1)]

(a) To a solution of 2.93 g 2-oxoglutaric acid in 20 ml dimethylformamide 3.63 g dicyclohexylamine was added, and the mixture was heated to 50° C. 4.75 g 4-nitrobenzyl bromide was then added, and the resulting mixture was stirred at b 70° C. for 15 minutes. After cooling the mixture, 100 ml ethyl acetate was added to precipitate a crystal, which was then filtered and washed with ethyl acetate. The resulting filtrate and the washings were combined together and washed with water and brine, after which the mixture was dried (MgSO$_4$). The solvent was concentrated under reduced pressure, and the resulting residue was eluted with hexane-ethyl acetate-acetic acid (50:50:1) via column chromatography using silica gel. The eluted fraction containing the desired product was collected and concentrated under reduced pressure to yield 5.2 g of the subject compound (1) in the form of a crystal. Melting point: 100° to 102° C.

IRν$_{max}^{KBr}$ cm$^{-1}$: 1735, 1707, 1530, 1345, 1275, 1085
NMR (90 MHz, CDCl$_3$-d$_6$-DMSO)δ: 2.5–2.8 (2H, m), 2.9–3.3 (2H, m), 5.40(2H, s), 7.62 (2H, d, J=9 Hz), 8.28 (2H, d, J=9 Hz)
Elemental analysis (as C$_{12}$H$_{11}$NO$_7$):
Calculated: C, 51.25; H, 3.94; N, 4.98
Found: C, 51.17; H, 3.92; N, 4.96

(b) To a solution of 2.93 g 2-oxoglutaric acid in 20 ml dimethylformamide 2.79 ml triethylamine and then 4.53 g 4-nitrobenzyl bromide were added, and the mixture was stirred at room temperature for 5 hours. The reaction mixture was poured into ice water and extracted (2 times) with ethyl acetate, after which it was treated in the same manner as in Reference Example 1 (a) to yield 3.6 g of the subject compound (1) in the form of a crystal.

(c) To a suspension of 3.36 g monosodium 2-oxoglutarate in 30 ml dimethylformamide 4.53 g 4-nitrobenzyl bromide was added, and the mixture was stirred at 50° to 60° C. for 2 hours. The reaction mixture was poured into ice water and extracted (2 times) with ethyl acetate, after which it was treated in the same manner as in Reference Example 1 (a) to yield 3.92 g of the subject compound (1) in the form of a crystal.

Reference Example 2

Production of 1-methyl-2-oxoglutarate[Compound (2)]:

4.0 g sodium hydride (60% dispersion in mineral oil) was added to a solution of 27.93 g of 2-benzyloxycarbonylamino-5-oxo-2-tetrahydrofurancarboxylic acid obtained via the method described in the Journal of Organic Chemistry, 6, 878 (1941) in 100 ml dimethylformamide while stirring and ice-cooling the solution. 28.4 g methyl iodide was then added, and the reaction mixture was stirred at room temperature for 4 hours. 14.2 g methyl iodide was further added, and the mixture was stirred for 3 more hours. The mixture was poured into water and extracted with ethyl acetate. The organic layer was successively washed with aqueous sodium bicarbonate and brine, and thereafter it was dried (over $MgSO_4$). The solvent was distilled off, and the precipitating crystal was collected by filtration and washed with ether to yield 27.25 g methyl 2-benzyloxycarbonylamino-5-oxo-2-tetrahydrofurancarboxylate in the form of a colorless crystal.

Melting point: 134° to 134.5° C.

$IRv_{max}^{KBr}$ cm$^{-1}$: 3295, 1780, 1758, 1700, 1540, 1308, 1196, 1049

To 10.0 g of this product 20 ml of a 30% solution of hydrogen bromide in acetic acid was added, and the mixture was stirred for 30 minutes. While cooling with ice, the reaction mixture was twice washed with 500 ml hexane-ether (9:1) (decantation), and the resulting residue, after adding water, was extracted with ethyl acetate (4 times). The organic layer was washed with brine and dried (over $MgSO_4$), and the solvent was distilled off. The resulting residue was eluted with hexane-ethyl acetate (1:1) via column chromatography using silica gel. The eluted fraction containing the desired product was collected and concentrated under reduced pressure to yield 2.95 g of the subject compound (2) in the form of a colorless crystal.

Melting point: 54.5° to 55.0° C.

$IRv_{max}^{KBr}$ cm$^{-1}$: 3430, 1750, 1735, 1710, 1275, 1255, 1225, 1080

NMR (90 MHz, CDCl$_3$)δ: 2.60–3.27(4H, m), 3.88(3H, s), 8.20(1H, br, s)

Elemental analysis (as $C_6H_8O_5$):
Calculated: C, 45.01; H, 5.04
Found: C, 44.92; H, 4.92

Reference Example 3

Production of 1-(4-nitrobenzyl)2-oxoglutarate[Compound (1)]

To a solution of 838 mg 2-benzyloxycarbonylamino-5-oxo-2tetrahydrofurancarboxylic acid in 5 ml of dimethylformamide 120 mg sodium hydride (60% dispersion in mineral oil) was added, while stirring and ice-cooling the solution. 648 mg 4-nitrobenzyl bromide was then added, and the mixture was stirred at room temperature for 2.5 hours. To the reaction mixture a saturated aqueous solution of sodium bicarbonate was added, then the resulting mixture was extracted with ethyl acetate. The organic layer, after washing with brine, was dried ($MgSO_4$), and the solvent was distilled off. The resulting residue was eluted with hexane-ethyl acetate (1:1) via column chromatography using silica gel. The eluted fraction containing the desired product was collected and concentrated under reduced pressure to yield 687 mg 4-nitrobenzyl 2-benzoyloxycarbonylamino-5-oxo-2-tetrahydrofurancarboxylate in the form of a colorless crystal.

Melting point: 127° to 127.5° C.

$IRv_{max}^{KBr}$ cm$^{-1}$: 3310, 1780, 1759, 1728, 1520, 1345, 1185, 1042

2.07 g of this product was treated in the same manner as in Reference Example 2 to yield 1.14 g of the subject compound (1), which was completely identified with the compound (1) obtained in Reference Example 1 in melting point, IR spectrum and NMR spectrum.

Reference Example 4

Production of 1-benzyl2-oxoglutarate[Compound (4)

2.92 g 2-oxoglutaric acid was dissolved in 20 ml anhydrous dimethylformamide. To the resulting solution 3.63 g dichlorohexylamine and 2.61 ml benzyl bromide were added, and the mixture was stirred at room temperature for 2 hours. To the reaction mixture ethyl acetate was added, and the precipitating crystal was filtered. After washing with water, the filtrate was dried ($Na_2SO_4$), and the solvent was distilled off. The resulting residue was eluted with hexane-ethyl acetate-acetic acid (50:50:1) via column chromatography using silica gel. The eluted fraction containing the desired product was then collected and concentrated under reduced pressure to yield 3.20 g of the subject compound (4) in the form of a colorless crystal, which was then recrystallized from ether-hexane to yield a colorless prismatic crystal.

Melting point: 51° to 52° C.

$IRv_{max}^{Nujol}$ cm$^{-1}$: 1740, 1705, 1270, 1090, 1040

NMR(90 MHz, CDCl$_3$)δ: 2.67(2H, t, J=6 Hz), 2.97(2H, m), 5.26(2H, s), 7.35(5H, s), 8.9(1H, b)

Elemental analysis (as $C_{12}H_{12}O_5$):
Calculated: C, 61.01; H, 5.12
Found: C, 61.02; H, 5.12

Reference Example 5

Production of 1-(4-nitrobenzyl)4-methyl-2-oxoglutarate [Compound (5)]:

0.74 g 4-methyl-2-oxoglutaric acid was dissolved in 6 ml anhydrous dimethylformamide. To the resulting solution 0.93 ml dicyclohexylamine and 1.0 g 4-nitrobenzyl bromide was added, and the mixture was stirred at room temperature for 14 hours. To the reaction mixture ethyl acetate was added, and the precipitating crystal was filtered. After washing with water, the filtrate was dried (over $Na_2SO_4$), and the solvent was distilled off. The resulting residue was eluted with hexane-ethyl acetate (1:1→1:3) via column chromatography using silica gel. The eluted fraction containing the desired compound was collected and concentrated under reduced pressure to yield 0.66 g of the subject compound (5) in the form of a light yellow oily substance.

$IRv_{max}^{Neat}$ cm$^{-1}$: 1780–1700, 1520, 1345, 1220, 1170

NMR(90 MHz, CDCl$_3$)δ: 1.32(3H, d, J=6 Hz), 2.2-3.3(3H, m), 5.38(2H, s), 6.0(1H, b), 7.55(2H, d, J=9 Hz), 8.22(2H, d, J=9 Hz)

Reference Example 6

Production of 1-(4-nitrobenzyl)2-oxo-3-phenylthioglutarate

[Compound(6)]

To a suspension of 2.25 g 3-bromo-2-oxoglutaric acid in 40 ml dichloromethane 1.0 ml thiophenol and then 4.15 ml triethylamine were added, while ice-cooling and stirring the suspension. The reaction mixture was stirred at room temperature for 45 minutes, then the solvent was evaporated. The resulting residue was partitioned to ethyl acetate and 1N-hydrochloric acid. The ethyl acetate layer was separated, washed with water and dried (over Na$_2$SO$_4$), then the solvent was evaporated to yield 2.28 g 2-oxo-3-phenylthioglutaric acid in the form of a light yellow oily substance.

IRv$_{max}^{Neat}$ cm$^{-1}$: 3000(b),1720, 1470, 1440, 1400, 1280, 1200

NMR(90MHz, CDCl$_3$)δ: 2.87(2H, d, J=8 Hz), 4.73(1H, t, J=8 Hz), 7.40(5H, s), 9.4(2H, b)

To a solution of 2.28 g of this product in 18 ml dimethylformamide 1.43 ml dicyclohexylamine and 1.56 ml 4-nitrobenzyl bromide were added, while ice-cooling and stirring the solution. The reaction mixture was stirred at room temperature for 15 hours, and thereafter it was diluted with ethyl acetate. The precipitating crystal was filtered. The resulting filtrate was washed with water and dried (over Na$_2$SO$_4$), then the solvent was distilled off. The resulting residue was eluted with hexane-ethyl acetate (1:2→1:3) via column chromatography using silica gel. The eluted fraction containing the desired compound was collected and concentrated under reduced pressure to yield 2.25 g of the subject compound (6) in the form of a colorless crystal, which was then recrystallized from ether-hexane to yield a colorless prismatic crystal.

Melting point: 119° to 120° C.

IRv$_{max}^{Nujol}$ cm$^{-1}$: 1745, 1730, 1700, 1520, 1440, 1350, 1280

NMR (90 MHz, CDCl$_3$)δ: 2.85(2H, d, J=8 Hz), 4.7(1H, m), 5.43(2H, s), 6.7(1H, b), 7.35(5H, s), 7.60(2H, d, J=9 Hz)

Elemental analysis (as C$_{18}$H$_{15}$NO$_7$S):
Calculated: C, 55.52; H, 3.88; N, 3.60
Found: C, 55.49; H, 3.90; N, 3.50

Reference Example 7

Production of 1-(4-nitrobenzyl)3-ethylthio-2-oxoglutarate

[Compound (7)]

To a suspension of 1.00 g 3-bromo-2-oxoglutaric acid in 20 ml dichloromethane 0.33 ml ethanethiol and then 1.83 ml triethylamine were added, while ice-cooling and stirring the suspension. The reaction mixture was stirred at room temperature for 3 hours, then the solvent was distilled off. The resulting residue was partitioned to ethyl acetate and 1N-hydrochloric acid. The ethyl acetate layer was separated, washed with water and dried (over Na$_2$SO$_4$), then the solvent was distilled off to yield 0.82 g 3-ethylthio-2-oxoglutaric acid in the form of a pale yellow oily substance.

IRv$_{max}^{Neat}$ cm$^{-1}$: 3000(b), 1720, 1400, 1250

NMR (90 MHz, CDCl$_3$)δ: 1.23(3H, t, J=8 Hz), 2.55(2H, q, J=8 Hz), 3.0(2H, b), 4.4(1H, b), 8.9(2H, b)

To a solution of 0.82 g of this product in 8 ml dimethylformamide 0.65 ml dicyclohexylamine and 0.70 g 4-nitrobenzyl bromide were added, while ice-cooling and stirring the solution. The reaction mixture was stirred at room temperature for 3 hours, and then it was diluted with ethyl acetate. The precipitating crystal was filtered. The resulting filtrate was washed with water and dried (over Na$_2$SO$_4$), then the solvent was distilled off. The resulting residue was eluted with hexane-ethyl acetate (3:2) via column chromatography using silica gel. The eluted fraction containing the desired compound was collected and concentrated under reduced pressure to yield 0.61 g of the subject compound (7) in the form of a colorless crystal, which was then re-crystallized from isopropyl ether to yield a colorless prismatic crystal.

Melting point: 100° to 101° C.

IRv$_{max}^{Nujol}$ cm$^{-1}$: 1745, 1720, 1700, 1530,, 1350, 1255

NMR(90 MHz, CDCl$_3$)δ: 1.18(3H, t, J=8 Hz), 2.48(2H, q, J=8 Hz), 2.95(2H, m), 4.3(1H, b), 5.41(2H, s), 7.0(1H, b), 7.57(2H, d, J=9 Hz), 8.25(2H, d, J=9 Hz)

Elemental analysis (as C$_{14}$H$_{15}$NO$_7$S):
Calculated: C, 49.26; H, 4.43; N, 4.10
Found: C, 49.32; H, 4.33; N, 3.99

Reference Example 8

Production of 1-t-butyl 2-oxoglutarate [Compound (8)]

To a solution of 5.0 g 5-oxo-2-tetrahydrofurancarboxylic acid in 100 ml dichloromethane 0.3 ml concentrated sulfuric acid and then an excess amount of isobutene (about 50 ml) were added, while maintaining the solution at −60° C. The reaction mixture was kept standing in a tightly seald flask at room temperature overnight, and thereafter it was poured into a cooled saturated aqueous solution of sodium bicarbonate, and the dichloromethane layer was separated. After washing with water and drying (over Na$_2$SO$_4$), the dichloromethane layer was concentrated to yield t-butyl 5-oxo-2- tetrahydrofurancarboxylate in the form of a colorless oily substance.

IRv$_{max}^{Neat}$ cm$^{-1}$: 1760

NMR(60 MHz, CDCl$_3$)δ: 1.50(9H, s), 2.4(4H, m), 4.8(1H, m)

This product was disslved in 50 ml absolute methanol, and 100 mg sodium methylate was added while ice-cooling and stirring the solution. While cooling with ice, the reaction mixture was stirred for 3 hours, and then it was concentrated and poured into a mixture of ethyl acetate and an aqueous ammonium chloride solution. The ethyl acetate layer was separated and dried (over Na$_2$SO$_4$), then the solvent was distilled off to yield 8.2 g 1-t-butyl-5-methyl 2-hydroxyglutarate in the form of a colorless crystal, which was then re-crystallized from hexane to yield a colorless prismatic crystal.

Melting point: 36° to 37° C.

IRv$_{max}^{Nujol}$ cm$^{-1}$: 3450, 1735, 1260, 1230, 1160, 1110

NMR(90 MHz, CDCl$_3$)δ: 1.47(9H, s), 1.7-2.6(4H, m), 2.87(1H, d, J=5 Hz), 3.63(3H, s), 4.1(1H, m)

Elemental analysis (as C$_{10}$H$_{18}$O$_5$):
Calculated: C, 55.03; H, 8.31
Found: C, 54.60; H, 8.35

To a solution of 0.39 ml oxalyl chloride in 12 ml dichloromethane a solution of 0.60 ml dimethyl sulfoxide in 4 ml dichloromethane was added at −70° C. under nitrogen gas atmosphere. To the mixture a solution of 0.95 g 1-t-butyl 5-methyl 2-hydroxyglutarate as obtained above in 3.5 ml dichloromethane was added, and the resulting mixture was stirred at −70° C. for 15 minutes, then 3.0 ml triethylamine was added. The reaction mixture, after raising temperature to −40° C., was poured into ice water and extracted with dichloromethane. The resulting extract was successively washed with water, dilute acetic acid and water, and thereafter it was dried (Na$_2$SO$_4$), and the solvent was evaporated. The resulting residue was eluted with hexane-ethyl acetate (5:1) via column chromatography using silica gel. The eluted fraction containing the desired product was collected and concentrated under reduced pressure to yield 0.60 g 1-t-butyl 5-methyl 2-oxoglutarate in the form of a pale yellow oily substance.

IR$v_{max}^{Neat}$ cm$^{-1}$: 1730, 1370, 1295, 1260, 1200, 1160, 1080

NMR(90 MHz, CDCl$_3$)δ: 1.57(9H,s), 2.63(2H,t,J=6 Hz), 3.10(2H,s,J=6 Hz), 3.69(3H,s)

108 mg of this product was dissolved in a mixture of 1 ml tetrahydrofuran and 1 ml water, then 0.4 ml 1N-sodium hydrooxide was added while ice-cooling the stirring the solution. The reaction mixture, after being stirred for 45 minutes with ice-cooling, was poured into a mixture of water and ethyl acetate. The water layer was separated and adjusted to pH 4 with 1N-hydrochloric acid, and thereafter it was extracted with ethyl acetate. The resulting extract was washed with brine and dried (Na$_2$SO$_4$), then the solvent was evaporated. The resulting residue was eluted with hexane-ethyl acetate (3:2→1:2) via column chromatography using silica gel. The eluted fraction containing the desired product was collected and concentrated under reduced pressure to yield 26 mg of the subject compound (8) in the form of a colorless oily substance.

IR$v_{max}^{Neat}$ cm$^{-1}$: 1740, 1370, 1300, 1255, 1160, 1080
NMR(90 MHz, CDCl$_3$)δ: 1.53(9H, M), 2.75(4H, b)

Reference Example 9

Production of 1-diphenylmethyl 2-oxoglutarate
[Compound (9)]

2.93 g 2-oxoglutaric acid, 4.75 g diphenylmethyl bromide and 3.63 g dicyclohexylmaine were treated in the same manner as in Reference Example 1 (a) to yield 3.2 g of the subject compound (9) in the form of a crystal.
Melting point: 107° to 109° C.
IR$v_{max}^{KBr}$ cm$^{-1}$: 1730, 1710
NMR(60 MHz, CDCl$_3$)δ: 2.58-3.17(4H, m), 6.99(1H, s), 7.31-7.54(10H, m)
Elemental analysis (as C$_{18}$H$_{16}$O$_5$):
Calculated: C, 69.22; H, 5.16
Found: C, 69.30; H, 5.18

Reference Example 10

Production of 1-diphenylmethyl 2-oxo-3-phenylthioglutarate
[Compound (10)]

To a solution of 6.7 g of 2-oxo-3-phenylthioglutaric acid which was obtained via the method of Reference Example 6 in 30 ml dimethylformamide 4.0 ml dicyclohexylamine and 5.0 g diphenylmethyl bromide were added, while stirring the solution at room temperature. The reaction mixture, after having been stirred for 15 hours at room temperature, was diluted with ethyl acetate. The precitipating crystal was filtered, and the filtrate was washed with water and dried (over Na$_2$SO$_4$), then the solvent was distilled off. The resulting residue was eluted with hexane-ethyl acetate (3:1→1:1) via column chromatography using silica gel. The eluted fraction containing the desired product was collected and concentrated under reduced pressure to yield 3.2 g of the subject compound (10) in the form of a light yellow crystal, which was then re-crystallized from hexane-ethyl acetate to yield a colorless needle crystal.
Melting point: 98° to 100° C.
IR$v_{max}^{Nujol}$ cm$^{-1}$: 1740, 1205, 1180
NMR(60 MHz, CDCl$_3$)δ: 2.85(2H, d, J=8 Hz), 4.70(1H, t, J=8 Hz), 7.05(1H, s), 7.3(15H, m)

Reference Example 11

Production of 1-pivaloyloxymethyl 2-oxoglutarate
[Compound (11)]

To a solution of 2.93 g of 2-oxoglutaric acid and 3.48 ml N,N-diisopropylethylamine in 20 ml dimethylformamide 3.13 g sodium iodide and 3.02 ml chloromethyl pivalate were added, and the resulting mixture was stirred at room temperature for 2 hours, and thereafter it was diluted with ethyl acetate. The precipitating crystal was filtered, and the filtrate was concentrated to dryness under reduced pressure. The resulting residue, after adding ethyl acetate, was washed with water and dried (over MgSO$_4$). The solvent was then distilled off, and the resulting residue was eluted with dichloromethane-ethyl acetate (1:1) via column chromatography using silica gel, then the eluted fraction containing the desired product was collected and concentrated under reduced pressure to yield 1.52 g of the subject compound (11) in the form of a colorless oily substance.
IR$v_{max}^{Neat}$ cm$^{-1}$: 2970, 1750, 1710
NMR(90 MHz, CDCl$_3$)δ: 1.24(9H, s), 2.67-3.19(4H, m), 5.89(2H, s)

Reference Example 12

Production of 1-(4-nitrobenzyl) 4-phenyl-2-oxoglutarate
[Compound (12)]

To a solution of 4.26 g 4-phenyl-2-oxoglutaric acid in 30 ml dimenthylformamide 2.67 ml dicyclohexylamine and 2.9 g 4-nitrobenzyl bromide were added, and the resulting mixture was stirred at room temperature for 20 hours. The reaction mixture was diluted with ethyl acetate, and the precipitating crystal was filtered. The resulting filtrate was washed with water and dried (over MgSO$_4$), then the solvent was distilled off. The resulting residue was subjected to column chromatography using silica gel and eluted with hexane-ethyl acetate (2:1→1:1), then the eluted fraction containing the desired product was collected and concentrated under reduced pressure to yield 2.89 g of the subject compound (12) in the form of a pale yellow crystal, which was then recrystallized from ethyl acetate-hexane to yield a pale yellow prismatic crystal.
Melting point: 149° to 150° C.
IR$v_{max}^{KBr}$ cm$^{-1}$: 1760, 1740, 1710, 1600
NMR(90 MHz, CDCl$_3$)δ: 2.5-4.5(3H, m), 5.40(2H, s), 7.30(5H, s), 7.68(2H, d, J=9 Hz), 8.24(2H, d, J=9 Hz)

Reference Example 13

Production of 1-(4-nitrobenzyl) 4-benzyl-2-oxoglutarate
[Compound (13)]

To a solution of 0.98 ml diisopropylamine in 13 ml anhydrous tetrahydrofuran 4.29 ml 1.5M n-butyllithium (in hexane solution) was added under nitrogen gas atmosphere, while stirring the solution at −78° C. After the mixture was stirred for 15 minutes, a solution of 1.18 g dimethyl 2-oxoglutarate dimethyl ketal in 7 ml anhydrous tetrahydrofuran was added over a period of 15 minutes, then the resulting mixture was stirred for 15 minutes. A solution of 0.76 ml benzyl bromide and 0.28 ml hexamethylphosphoramide in 7 ml anhydrous tetrahydrofuran was added over a period of 5 minutes, and the resulting mixture was stirred at −78° C. for 30 minutes. The reaction mixture, after raising temperature to −20° C. over a period of 2 hours with stirring, was diluted with a saturated aqueous solution of ammonium chloride and extracted with ethyl acetate. The resulting extract was washed with water and dried (MgSO$_4$), then the solvent was evaporated. The resulting residue was eluted with hexane-ethyl acetate (5:1→2:1) via column chromatography using silica gel to yield 1.64 g dimethyl 4-benzyl-2-oxoglutarate dimethyl ketal in the form of a light yellow oily substance.

IR$\nu_{max}^{Neat}$ cm$^{-1}$: 1740, 1600

NMR(90 MHz, CDCl$_3$)δ: 2.2–3.0(5H, m), 3.07(3H, s), 3.17(3H, s), 3.57(3H, s), 3.68(3H, s), 7.0–7.4(5H, m)

This product was dissolved in 10 ml methanol, and 15 ml of a 3.5M aqueous solution of potassium hydroxide was added. The mixture was stirred at room temperature for 3.5 hours, then methanol was evaporated. The reaction mixture, after adjustment to pH 1 with 6N hydrochloric acid, was saturated with sodium chloride and extracted with ethyl acetate. The resulting extract was washed with brine and dried (over Na$_2$SO$_4$), then the solvent was distilled off to yield 1.43 g 4-benzyl-2-oxoglutaric acid dimethyl ketal in the form of a yellow oily substance.

This oily substance was dissolved in 40 ml tetrahydrofuran, and 40 ml 1N hydrochloric acid was added. The mixture was then stirred at room temperature for 30 minutes. After evaporation of the tetrahydrofuran, the water layer was saturated with sodium chloride and extracted with ethyl acetate. The resulting extract was washed with brine and dried (over Na$_2$SO$_4$), then the solvent was evaporated to yield 1.40 g 4-benzyl-2-oxoglutaric acid in the form of a yellow oily substance.

This oily substance was dissolved in 10 ml dimethylformamide, and 0.83 ml dicyclohexylamine and 0.90 g 4-nitrobenzyl bromide were added. The mixture was then stirred at room temperature for 15 minutes. To the reaction mixture ethyl acetate was added, and the precipitating crystal was filtered. The resulting filtrate was washed with water and dried (over MgSO$_4$), then the solvent was distilled off. The resulting residue was eluted with hexaneethyl acetate(2:1) via column chromatography using silica gel, then the eluted fraction containing the desired product was concentrated under reduced pressure to yield 1.35 g of the subject compound (13) in the form of a colorless oily substance.

IR$\nu_{max}^{Neat}$ cm$^{-1}$: 3700–3200, 3150–3000, 1760(b), 1600

NMR(90 MHz, CDCl$_3$)δ: 2.5–3.4(5H, m), 5.30(2H, s), 7.0–7.4(5H, m), 7.45(H, d, J=9 Hz), 8,18(2H, d, J=9 Hz)

Mass spectrum m/z: 371(M+)

Reference Example 14

Production of 1-(4-nitrobenzyl) 4-methoxymethyl-2-oxoglutarate

[Compound (14)]

To a solution of 2.85 ml diisopropylamine in 30 ml anhydrous tetrahydrofuran 12.5 ml 1.5M n-butyllithium (in hexane solution) was added at −78° C. under a nitrogen gas atmosphere, and the mixture was stirred for 15 minutes. To this mixed solution a solution of 3.45 g dimethyl 2-oxoglutarate dimethyl ketal in 15 ml anhydrous tetrahydrofuran was added over a period of 10 minutes, and the resulting mixture was stirred for 15 minutes. A solution of 1.32 ml chloromethyl methyl ether and 1.36 ml hexamethylphosphoramide in anhydrous tetrahydrofuran was added over a period of 10 minutes. The resulting mixture, after raising temperature to −20° C. over a period of 30 minutes, was stirred at the same temperature for 3 hours. To the reaction mixture a saturated aqueous solution of ammonium chloride was added, and the resulting mixture was extracted with ethyl acetate. The resulting extract was washed with water and dried (MgSO$_4$), then the solvent was evaporated. The resulting residue was eluted with hexane-ethyl acetate (2:1) via column chromatography using silica gel to yield 2.28 g dimethyl 4-methoxymethyl-2-oxoglutarate dimethyl ketal in the form of a light yellow oily substance.

IR$\nu_{max}^{Neat}$ cm$^{-1}$: 1750

NMR(90 MHz, CDCl$_3$)δ: 2.02(1H, dd, J=5, 15 Hz), 2.35(1H, dd, J=9, 15 Hz), 2.75(1H, m), 3.23(6H, s), 3.28(3H, s), 3.44(1H, d, J=5 Hz), 3.46(1H, d, J=6 Hz), 3.67(3H, s), 3.77(3H, s)

To a solution of 560 mg of this product in 4 ml methanol 6 ml of a 1.8M aqueous solution of potassium hydroxide was added, and the mixture was stirred at room temperature for 3 hours. After evaporation of the methanol, the water layer was washed with ether and adjusted to pH 1 with 6N hydrochloric acid, after which it was saturated with sodium chloride and extracted with ethyl acetate. The resulting extract was washed with brine and dried (MgSO$_4$), then the solvent was evaporated to yield 471 mg 4-methoxymethyl-2-oxoglutaric acid dimethyl ketal in the form of a yellow oily substance, which was then dissolved in 10 ml tetrahydrofuran. To the resulting solution 10 ml 1N hydrochloric acid was added, and the mixture was stirred at room temperature for 4 days. After evaporating tetrahydrofuran, the water layer was saturated with sodium chloride and extracted with ethyl acetate. The resulting extract was washed with brine and dried (MgSO$_4$), then the solvent was evaporated to yield 397 mg 4-methoxymethyl-2-oxoglutaric acid in the form of a colorless oily sybstance.

355 mg of this oily substance was dissolved in 3 ml dimethylformamide, and the resulting solution, after adding 0.30 ml dicyclohexylamine and 323 mg 4-nitrobenzyl bromide, was stirred at room temperature for 15 hours. To the reaction mixture ethyl acetate was added, and the precipitating crystal was filtered. The resulting filtrate was washed with water and dried (MgSO$_4$), then the solvent was evaporated. The resulting residue was eluted with hexane-ethyl acetate (2:1) via column chromatography using silica gel, then the eluted fraction containing the desired product was concentrated under reduced pressure to yield 293 mg of the subject compound (14) in the form of a yellow oily substance.

IRv$_{max}^{Neat}$ cm$^{-1}$: 1750(b), 1600
NMR(90 MHz, CDCl$_3$)δ: 3.05(3H, m), 3.48(3H, s), 3.6–3.9(2H, m), 5.37(2H, s), 7.52(2H, d, J=9 Hz), 8.21(2H, d, J=9 Hz)

Reference Example 15

Production of 2-oxoglutaric acid 1-anilide [Compound (15)]

To a solution of 1.46 g 2-oxoglutaric acid in acetonitrile (20 ml) 2.06 g DCC was added, and the mixture was stirred at room temperature for 10 minutes. 930 mg aniline was then added, and the solution was stirred at room temperature for 5 hours. The separating white precipitate was filtered, and the resulting filtrate, after adding ethyl acetate (40 ml), was extracted with an aqueous solution of sodium bicarbonate (30 ml). The resulting extract, after adjustment to pH 3.0 with 2N hydrochloric acid, was extracted with ethyl acetate. The organic layer was washed with water and dried (MgSO$_4$), then the solvent was evaporated. The resulting residue was eluted with hexane-ethyl acetate (1:2) via silica gel column chromatography, then the eluted fraction containing the desired product was concentrated under reduced pressure to yield 390 mg of the subject compound (15) in the form of a colorless crystal.
Melting point: 192° to 193° C.
IRv$_{max}^{KBr}$ cm$^{-1}$: 3340, 1700, 1690, 1600, 1540, 1450, 1320
NMR(90 MHz, CDCl$_3$-d$_6$-DMSO)δ: 2.42–2.70(2H, m), 2.90–3.32(2H, m), 7.01–7.90(5H, m)

Reference Example 16

Production of 2-oxoglutaric acid 1-pyrrolidinamide [Compound (16)]

584 mg 2-oxoglutaric acid and 284 mg pyrrolidine were treated in the same manner as in Reference Example 15 to yield 412 mg of the subject compound (16) in the form of a colorless crystal.
Melting point: 101° to 102° C.
IRv$_{max}^{KBr}$ cm$^{-1}$: 2970, 1730, 1710, 1600, 1390, 1330, 1210, 1170
NMR(90 MHz, CDCl$_3$)δ: 1.81–2.06(4H, m), 2.65–2.84(2H, m), 3.08–3.27(2H, m), 3.43–3.80(4H, m), 8.60–9.01(1H, m)

Reference Example 17

Production of 2-oxoglutaric acid 1-n-propylamide [Compound (17)]

1.46 g 2-oxoglutaric acid and 0.828 ml n-propylamine were treated in the same manner as in Reference Example 15 to yield 496 mg of the subject compound (17) in the form of a light yellow crystal.
Melting point: 79° to 81° C.
IRv$_{max}^{KBr}$ cm$^{-1}$: 3250, 2960, 1730, 1690, 1660, 1530, 1440, 1400
NMR(90 MHz, CDCl$_3$)δ: 0.81–1.19(3H, t, J=6 Hz), 1.36–1.75(2H, m), 2.58–2.72(2H, m), 3.12–3.34(4H, m), 6.79–7.03(1H, m), 7.91–8.37(1H, m)

Reference Example 18

Production of 1-(4-nitrobenzyl) 3-bromo-2-oxoglutarate [Compound (18)]

1.5 g 1-(4-nitrobenzyl) 2-oxoglutarate was dissolved in 15 ml anhydrous chloroform. To this solution a solution of 0.3 ml bromine in 5 ml anhydrous chloroform was gradually added dropwise over a period of 4 hours at 50° C. with stirring. After cooling the reaction mixture, a brine was added, and the resulting mixture was extracted with dichloromethane. The organic layer was washed with water and dried (MgSO$_4$), then the solvent was evaporated to yield 1.89 g of the subject compound (18) in the form of a light yellow oily substance.
IRv$_{max}^{neat}$ cm$^{-1}$: 3300, 1800, 1735, 1605, 1520, 1350
NMR(90 MHz, CDCl$_3$)δ: 2.67–3.55(2H, m), 5.30–5.38(1H, m), 5.46(2H, s), 7.58 and 8.22(4H, 2d, J=9 Hz), 8.80–9.50(1H, br)

Reference Example 19

Production of di-1-(4-nitrobenzyl)-5-t-butyl 3-bromo-2-oxoglutarate

[Compound (19)]

1.89 g 1-(4-nitrobenzyl) 3-bromo-2-oxoglutarate (18) was dissolved in 10 ml dichloromethane, and 0.1 ml concentrated sulfuric acid was added while ice-cooling and stirring the solution. While cooling the solution with ice, 10 ml liquefied isobutene was added. The reaction mixture in the tightly sealed flask was gradually warmed to room temperature and kept standing overnight. The reaction mixture was then neutralized with an aqueous solution of sodium bicarbonate, then excess isobutene was evaporated under nitrogen gas atmosphere. The resulting residue, after dilution with water, was extracted with dichloromethane. The organic layer was washed with water and dried (MgSO$_4$), then the solvent was evaporated under reduced pressure. The resulting residue was passed through a silica gel column and eluted with dichloromethane, then the eluted fraction containing the desired product was collected and concentrated under reduced pressure to yield 1.448 g of the subject compound (19) in the form of a light yellow oily substance.
IRv$_{max}^{neat}$ cm$^{-1}$: 2980, 1735, 1605, 1525, 1370, 1350
NMR(90 MHz, CDCl$_3$)δ: 1.42(9H, s), 2.82–3.41(2H, m), 5.26–5.36(1H, m), 5.46(2H, s), 7.62 and 8.21(4H, 2d, J=9 Hz)

Reference Example 20

Production of di-1-(4-nitrobenzyl)-5-ethyl 3-bromo-2-oxoglutarate

[Compound (20)]

1.0 g 1-(4-nitrobenzyl) 2-oxoglutarate [Compound (1)] was brominated using primary chloroform as the solvent in accordance with the method of Reference Example 18 to yield both 772 mg of the subject compound (20) in the form of a light yellow oily substance and 368.5 mg of the compound (18) as a by-product.
NMR(90 MHz, CDCl$_3$)δ: 1.23(3H, t, J=6 Hz), 2.89–3.48(2H, m), 4.14(2H, q, J=6 Hz), 5.26–5.42(1H, m), 5.46(2H, s), 7.63 and 8.23(4H, 2d, J=9 Hz)

Reference Example 21

Production of di-1-(4-nitrobenzyl)-5-t-butyl-2-oxo-3-[(3R,4R)-3-phenylacetamido-2-azetidinone-4-yl]thioglutarate[Compound (21)]

109 mg (3R,4R)-4-mercapto-3-phenylacetamido-2-azetidinone and 690 mg of the compound (19) obtained in Reference Example 19 were suspended in 3 ml acetone. The resulting suspension was stirred at room temperature for 15 minutes, then 3 ml hexamethylphosphoramide was added, and the resulting mixed suspension was astirred at room temperature for 3 hours. The reaction mixture, after adding 10 ml water, was extracted with 15 ml ethyl acetate. The organic layer was washed with water and dried (MgSO$_4$), then the solvent was evaporated under reduced pressure. The resulting residue was passed through a silica gel column and eluted with ethyl acetate-n-hexane (1:1), then the eluted fraction containing the desired product was collected and concentrated under reduced pressure to yield 209 mg of the subject compound (21), as a mixture of diastereomers, in the form of a white powder.

IR$v_{max}^{KBr}$ cm$^{-1}$: 3300, 2970, 1780, 1720, 1650, 1520, 1340, 1260, 1140

NMR(90 MHz, CDCl$_3$)δ: 1.42(9H, s), 2.58–2.94(2H, m), 3.57(2H, 2s), 4.40–4.63(1H, m), 4.72(1H, br), 4.96–5.16(1H, m), 5.31–5.58(3H, m), 6.48 and 6.72(1H, 2d, J=9 Hz), 7.27(5H, s), 7.49–7.57 and 8.12–8.25(4H, m)

Reference Example 22

Production of di-1-(4-nitrobenzyl)-5-ethyl 2-oxo-3-[(3R,4R)-3-phenylacetamido-2-azetidinone-4-yl]thioglutarate[Compound (22)]

158 mg (3R,4R)-4-mercapto-3phenylacetamido-2-azetidinone and 670 mg of the compound (20) obtained in Reference Example 20 were suspended in 3 ml acetone. The resulting suspension was stirred at room temperature for 15 minutes, then 3 ml hexamethylphosphoramide was added; the resulting mixed suspension was stirred at room temperature for 4 hours. The reaction mixture, after adding 50 ml water, was extracted with ethyl acetate. The organic layer was washed with water and dried (MgSO$_4$), then the solvent was evaporated under reduced pressure. The resulting residue was passed through a silica gel column and eluted with ethyl acetate-n-hexane (55:45), then the eluted fraction containing the desired product was collected and concentrated under reduced pressure to yield 300 mg of the subject compound (22) in the form of a white powder.

IR$v_{max}^{KBr}$ cm$^{-1}$: 3320, 1780, 1730, 1660, 1600, 1520, 1350, 1270, 1010, 850, 730

NMR(90 MHz, CDCl$_3$)δ: 1.20(3H, t, J=6 Hz), 2.43–3.16(2H, m), 3.56(2H, s), 4.09(2H, q, J=6 Hz), 4.35–4.75(1H, m), 4.96–5.15(1H, m), 5.34(2H, s), 5.42–5.56(1H, m), 6.63–7.00(1H, br), 7.26(5H, s), 7.52(2H, d, J=9 Hz), 8.10–8.22(2H, m)

Reference Example 23

Production of 1-(4-nitrobenzyl) 2-oxo-3-[(3R,4R)-3-phenylacetamido-2-azetidinone-4-yl]thioglutarate[Compound (23)]

623.5 mg (3R,4R)-4-mercapto-3-phenylacetamido-2-azetidinone and 2.121 g of the compound (18) obtained in Reference Example 18 were suspended in 14 ml acetone; the resulting suspension was stirred at room temperature for 15 minutes. After adding 14 ml hexamethylphosphoramide, the suspension was further stirred at room temperature for 4 hours. The reaction mixture, after adding water, was extracted with ethyl acetate. The organic layer was washed with brine and dried (MgSO$_4$), then the solvent was evaporated under reduced pressure to yield 3.063 g of a crude product of the subject compound (23) in the form of a light yellow oily substance.

Reference Example 24

Production of 1-(4-nitrobenzyl) 2-oxo-3-[(3R,4R)-3-phenoxyacetamido-2-azetidinone-4-yl]thioglutarate[Compound (24)]

2.523 g (3R,4R)-4-mercapto-3-phenoxyacetamido-2-azetidinone and 5.004 g of the compound (18) obtained in Reference Example 18 were suspended in 60 ml acetone; the resulting suspension was stirred at room temperature for 15 minutes. After adding 60 ml hexamethylphosphoramide, the suspension was further stirred at room temperature for 4 hours. The reaction mixture, after adding 400 ml water, was extracted with ethyl acetate. The organic layer was washed with brine and dried (MgSO$_4$), then the solvent was evaporated under reduced pressure to yield 9.80 g of a crude product of the subject compound (24) in the form of a yellow oil.

Reference Example 25

Production of (3R,4R)-3-tritylamino-4-tritylthio-2-azetidinone [Compound (25)]

1.0 g (3R,4R)-3-tritylamino-4-methanesulfonyl-2-azetidinone was dissolved in 20 ml tetrahydrofuran. To this solution 25 ml of a solution of 816 mg tritylmercaptane in tetrahydrofuran and 2.83 ml a 1N aqueous solution of sodium hydroxide were added while cooling the solution with ice. The resulting mixed solution was stirred at room temperature for 25 minutes. The reaction mixture was concentrated under reduced pressure, and the resulting concentrate, after adding 30 ml water, was extracted with 40 ml ethyl acetate. The organic layer was concentrated under reduced pressure; the precipitating crystal was filtered. The resulting filtrate was dried (MgSO$_4$), then the solvent was evaporated under reduced pressure. The resulting residue was passed through a silica gel column and eluted with ethyl acetate-n-hexane (1:5), then the eluted fraction containing the desired product was collected and concentrated under reduced pressure to yield 486.5 mg of the subject compound (25) in the form of a white crystal.

IR$v_{max}^{KBr}$ cm$^{-1}$: 3400, 3060, 1760, 1490, 1445, 1180, 745, 700,

NMR(90 MHz, CDCl$_3$)δ: 2.89(1H, d, J=8 Hz), 3.93(1H, s), 4.39(1H, d, J=5 Hz), 4.56(1H, dd, J=5 Hz, 8 Hz), 7.14–7.59(30H, m)

Reference Example 26

Production of (3R,4R)-3-phenylacetamido-4-tritylthio-2-azetidinone [Compound (26)]

302 mg of the compound (25) obtained in Reference Example 25 was dissolved in 10 ml acetone. To this solution 114 mg p-toluenesulfonic acid monohydrate was added while cooling the solution with ice, then the solution was stirred at room temperature for 1 hour. The reaction mixture was concentrated under reduced pressure, after which it was crystallized by ether addition. The precipitating crystal was collected via filtration and washed with 10 ml ether. This white crystal was then dissolved in 10 ml dichloromethane. To this solution 0.21 ml tirethylamine and 0.09 ml phenylacetyl chloride were added while cooling the solution with ice, then the solution was stirred for 1 hour. The reaction mixture was concentrated under reduced pressure; the resulting residue was passed through a silica gel column and eluted with ethyl acetate-n-hexane (1:1), then the eluted fraction containing the desired product was collected and concentrated under reduced pressure to yield 204 mg of the subject compound (26) in the form of a white powder.

IR$\nu_{max}^{KBr}$ cm$^{-1}$: 3270, 3050, 1765, 1665, 1495, 1440, 740, 700

NMR(90 MHz, CDCl$_3$)δ: 3.62(2H, s), 4.63(1H, d, J=5 Hz), 4.76(1H, br, s), 5.43(1H, dd, J=5 Hz, 9 Hz), 6.47(1H, d, J=9 Hz), 7.27(20H, s)

Reference Example 27

Production of (3R,4R)-3-(4-nitro)benzyloxycarboxylamino-4-tritylthio-2-azetidinone[Compound (27)]

3.9125 g of the compound (25) obtained in Reference Example 25 was dissolved in 130 ml acetone. To this solution 1.482 g p-toluenesulfonic acid monohydrate was added while cooling the solution with ice, then the solution was stirred at room temperature for 1 hour. The reaction mixture was concentrated under reduced pressure; the resulting residue was crystallized by adding 150 ml ether. The precipitating crystal was collected via filtration and washed with 50 ml ether to obtain 3.211 g (3R,4R)-3-amino-4-tritylthio-2-azetidinone p-toluenesulfonate in the form of a white crystal.

IR$\nu_{max}^{KBr}$ cm$^{-1}$: 3050, 1760, 1495, 1445, 1185, 1120, 1030, 1010, 740, 700, 680

NMR(90 MHz, d$_6$-DMSO)δ: 2.27(3H, s), 4.43(1H, d, J=5 Hz), 4.53–4.61(1H, m), 7.07(2H, d, J=8 Hz), 7.19–7.37(15H, m), 7.48(2H, d, J=8 Hz), 8.81(3H, br, s), 8.99(1H, s)

799 mg of the above p-toluenesulfonate was suspended in 10 ml tetrahydrofuran. To this suspension 10 ml water and 277 mg sodium bicarbonate were added while cooling the suspension with ice. To the resulting solution 3 ml of a solution of 388 mg 4-nitrobenzyloxycarbonyl chloride in tetrahydrofuran was added dropwise while cooling with ice, then the resulting mixed solution was stirred for 40 minutes. The reaction mixture was concentrated under reduced pressure and extracted with 20 ml ethyl acetate. The organic layer was washed with water and dried (MgSO$_4$), then the solvent was evaporated under reduced pressure. The resulting residue was passed through a silica gel column and eluted with ethyl acetate-n-hexane (1:1), then the eluted fraction containing the desired product was collected and concentrated under reduced pressure to yield 760 mg of the subject compound (27) in the form of a white powder.

Reference Example 28

Production of (3R,4R)-1-(t-butyldimethyl)silyl-3-phenylacetamido-4-tritylthio-2-azetidinone[Compound (28)]

456 mg of the compound (26) obtained in Reference Example 26 and 187 mg t-bytyldimethylchlorosilane were dissolved in 5 ml N,N-dimethylformamide. To this solution 153 μl triethylamine was added dropwise while ice-cooling and stirring the solution, which was then stirred at room temperature for 14.5 hours. 86 mg t-butyldimethylchlorosilane and 66 μl triethylamine were further added, and the resulting mixed solution was stirred at room temperature for 2.5 hours. The reaction mixture, after adding 50 ml water, was extracted with 50 ml ethyl acetate. The organic layer was washed with water and dried (MgSO$_4$), then the solvent was evaporated under reduced pressure. The resulting residue was passed through a silica gel column and eluted with n-hexane-ethyl acetate (1:1), then the eluted fraction containing the desired product was collected and concentrated under reduced pressure to yield 451.5 mg of the subject compound (28) in the form of a white powder.

IR$\nu_{max}^{KBr}$ cm$^{-1}$: 3300, 2930, 2855, 1760, 1685, 1495, 1250, 840, 820, 740, 700

NMR(90 MHz, CDCl$_3$)δ: 0.19(6H, s), 0.86(9H, s), 3.12(1H, d, J=15 Hz), 3.39(1H, d, J=15 Hz), 4.76(1H, d, J=5 Hz), 5.41(1H, dd, J=5 Hz, 9 Hz), 5.95(1H, d, J=9 Hz), 7.10–7.38(20H, m)

Reference Example 29

Production of (3R,4R)-1-(t-butyldimethyl)silyl-3-phenylacetamido-4-mercapto-2-azetidinone[Compound (29)]

100 mg of the compound (28) obtained in Reference Example 28 was dissolved in 3 ml methanol. To this solution a solution of 70 mg mercuric acetate in 2 ml methanol was added dropwise while cooling to −53+ to −47° C. with ice. The reaction mixture was stirred at −53° to −47° C. for 70 minutes, then hydrogen sulfide gas was passed through the mixture at lower than −70° C. for 5 minutes. Nitrogen gas was then passed through the liquid for 30 minutes to eliminate hydrogen sulfide gas. The reaction mixture was then concentrated under reduced pressure; the resulting residue, after dissolving in dichloromethane, was filtered to remove insoluble substances. The resulting filtrate was concentrated under reduced pressure. The resulting residue was passed through a silica gel column and eluted with n-hexane-ethyl acetate (7:3), then the eluted fraction containing the desired product was collected and concentrated under reduced pressure to yield 48 mg of the subject compound (29) in the form of an oil.

IR$\nu_{max}^{neat}$ cm$^{-1}$: 3300, 2960, 2940, 2860, 2550, 1765, 1740, 1660, 1540, 1255, 1020, 840, 820

NMR(90 MHz, CDCl$_3$)δ: 0.26(6H, s), 0.94(9H, s), 1.81(1H, d, J=8 Hz), 3.61(2H, s), 4.96(1H, dd, J=5 Hz, 8 Hz), 5.45(1H, dd, J=5 Hz, 9 Hz), 6.85(1H, d, J=9 Hz), 7.28(5H, s)

Reference Example 30

Production of (3R,4R)-3-phenylacetamido-4-mercapto-2-azetidinone [Compound (30)]

27 mg of the compound (29) obtained in Reference Example 29 was dissolved in 1.2 ml acetone. This solution, after adding 0.5 ml 1N hydrochloric acid, was stirred at room temperature for 1 hour. To the reaction mixture 20 ml water was added while cooling the liquid with ice, then the mixture was extracted with 30 m dichloromethane. The organic layer was evaporated under reduced pressure to yield 16.5 mg of the subject compound (30) in the form of a white crystal.

IR$\nu_{max}^{KBr}$ cm$^{-1}$: 3270, 2540, 1780, 1760, 1725, 1660, 1550, 1250, 980, 700

NMR(90 MHz, d$_6$-DMSO)δ: 2.89(1H, d, J=9 Hz), 3.52(2H, s), 4.98(1H, dd, J=5 Hz, 9 Hz), 5.25(1H, dd, J=5 Hz, 9 Hz), 7.31(5H, s), 8.73(1H, br.s), 8.85(1H, d)

Reference Example 31

Production of
(3R,4R)-1-(t-butyldimethyl)silyl-3-(4-nitro)benzyloxycarbonylamino-4-tritylthio-2-azetidinone

[Compound (31)]

367 mg of the compound (27) obtained in Reference Example 27 and 133 mg t-butyldimethylchlorosilane were dissolved in 4 ml N,N-dimethylformamide. To this solution 109 μl triethylamine was added dropwise while ice-cooling and stirring the solution. The solution was then stirred at room temperature for 14 hours. 62 mg t-butyldimethylchlorosilane and 47 μl triethylamine were further added, and the solution was stirred at room temperature for 3 hours. The reaction mixture, after adding 40 ml water, was extracted with 40 ml ethyl acetate. The organic layer was washed with water and dried (MgSO$_4$), then the solvent was evaporated under reduced pressure. The resulting residue was passed through a silica gel column and eluted with n-hexane-ethyl acetate (4:1), then the eluted fraction containing the desired product was collected and concentrated under reduced pressure to yield 286 mg of the subject compound (31) in the form of a white powder.

IR$v_{max}^{KBr}$ cm$^{-1}$: 2960, 2930, 2860, 1765, 1730, 1530, 1345, 1250, 740, 700

NMR(90 MHz, CDCl$_3$)δ: 0.30(6H, s), 0.96(9H, s), 4.70–5.31(5H, m), 7.18–7.49(17H, m), 8.15(2H, d, J=9 Hz)

Reference Example 32

Production of
(3R,4R)-[(2R)-2-(4-ethyl-2,3-dioxo-1-piperazinecarboxamido)phenylacetamido]-4-tritylthio-2-azetidinone

[Compound (32)]

383 mg (2R)-2-(4-ethyl-2,3-dioxo-1-piperazinecarboxamido)phenylacetic acid was suspended in 10 ml dichloromethane. To this suspension 165 μl trimethylchlorosilane and 181 μl triethylamine were added dropwise, while cooling the suspension with ice. The suspension was then stirred at room temperature for 30 minutes. The reaction mixture, after adding 101 μl N,N-dimethylformamide and 78 μl trichloromethyl chloroformate while cooling the mixture to −25° to −20° C., was stirred at −25° to −20° C. for 2 hours. The reaction mixture was then cooled down to −70° C.; 186 μl pyridine, 533 mg (3R,4R)-3-amino-4-tritylthio-2-azetidinone p-toluenesulfonate and 1 ml propylene oxide were added to the reaction mixture. The cooling bath (dry ice-acetone bath) was then removed, and the reaction mixture was warmed up to room temperature over a period of 1 hour. The reaction mixture was then concentrated under reduced pressure; the resulting residue was passed through a silica gel column and eluted with ethyl acetate. The eluted fraction containing the desired product was collected and concentrated under reduced pressure to yield 496 mg of the subject compound (32) in the form of a white powder.

IR$v_{max}^{KBr}$ cm$^{-1}$: 3300, 1780, 1770, 1720, 1690, 1510, 1360, 1180, 740, 700

NMR(90 MHz, CDCl$_3$)δ: 1.18(3H, t, J=7 Hz), 3.22–3.93(6H, m), 4.54(1H, d, J=5 Hz), 5.21(1H, br, s), 5.47–5.62(2H, m), 7.17–7.57(20H, m), 8.03(1H, d, J=9 Hz), 10.06(1H, d, J=6 Hz)

Reference Example 33

Production of
(3R,4R)-1-(t-butyldimethyl)silyl-3-[(2R)-2-(4-ethyl-2,3-dioxo-1-piperazinecarboxamido)phenylacetamido]-4-tritylthio-2-azetidinone[Compound (33)]

200 mg of the compound (32) obtained in Reference Example 32 was dissolved in 3 ml dichloromethane. To this solution 47 μl triethylamine was added while cooling the solution with ice. 70 μl t-butyldimethylsilyl trifluoromethanesulfonate was added dropwise in nitrogen gas flow, while ice-cooling and stirring the solution, which was then stirred at the same temperature for 1 hour. The reaction mixture was poured into 20 ml water and extracted with dichloromethane. The organic layer was washed with a saturated aqueous solution of sodium bicarbonate and dried (MgSO$_4$), then the solvent was evaporated under reduced pressure. The resulting residue was passed through a silica gel column and eluted with ethyl acetate, then the eluted fraction containing the desired product was collected and concentrated under reduced pressure to yield 183.5 mg of the subject compound (33) in the form of a white powder.

IR$v_{max}^{KBr}$ cm$^{-1}$: 3300, 2930, 1765, 1730, 1695, 1500, 1360, 1250, 1180, 700

NMR(90 MHz, CDCl$_3$)δ: 0.12(6H, s), 0.91(9H, s), 1.24(3H, t, J=8 Hz), 3.26–4.40(7H, m), 4.73(1H, d, J=5 Hz), 5.48–5.63(2H, m), 7.02–7.40(20H, m), 10.00(1H, d, J=7 Hz)

Reference Example 34

Production of 1-(4-nitro)benzyl 2-oxo-3-{(3R,4R)-3-[(2R)-2-(4-ethyl-2,3-dioxo-1-piperazinecarboxamido)phenylacetamido]-2-azetidinon-4-yl}-thioglutarate[Compound (34)]

1.0 g of the compound (33) obtained in Reference Example 33 was dissolved in 35 ml methanol; this solution was cooled to −55° to −50° C. To this solution a solution of 534 mg mercuric acetate in 14 ml methanol was added dropwise over a period of 15 minutes, then the resulting mixed solution was stirred. Respectively after 43 and 82 minutes of agitation, a solution of 267 mg mercuric acetate in 7 ml methanol and a solution of 134 mg mercuric acetate in 4 ml methanol were successively added. The resulting mixed solution was stirred for 2 hours and 10 minutes in total, while maintaining at −55° to −50° C. Hydrogen sulfide gas was passed through the reaction mixture at lower than −50° C. for 2 minutes, and nitrogen gas was further passed through the reaction mixture for 20 minutes, then the solvent for the reaction mixture was evaporated under reduced pressure. The resulting residue was dissolved in dichloromethane and filtered to remove insoluble substances. The resulting filtrate was evaporated to yield 1.037 g (3R,4R)-1-(t-butyldimethyl)silyl-3-[(2R)-2-(4-ethyl-2,3-dioxo-1-piperazinecarboxamido)phenylacetamido]-4-mercapto-2-azetidinone in the form of a light yellow powder. The entire amount of this product and 467.5 mg of the compound (18) obtained in Reference Example 18 were dissolved in a mixed solvent of 10 ml acetone and 10 ml hexamethylphosphoramide; the resulting solution was stirred at room temperature for 2 hours. To this solution 10 ml 1N hydrochloric acid was added, then the solution was stirred at room temperature for 1 hour and 40 minutes. The reaction mixture, after adding water, was extracted with 15 ml ethyl acetate. The organic layer was washed with water and dried (MgSO$_4$), then the solvent was evaporated under reduced pressure to yield 1.4415 g of the subject compound (35) in the form of a light yellow oily crude substance.

Reference Example 35

Production of mercury salt of 1-(t-butyldimethylsilyl)-2-azetidinone-4-thiol[Compound (35)]

0.1 g 1-(t-butyldimethylsilyl)-4-tritylthio-2-azetidinone was dissolved in 1 ml dichloromethane; the resulting solution was cooled to −78° C. and stirred. To this solution of 0.083 g mercuric acetate in 5 ml methanol was added, and the solution was stirred for 20 minutes. To the reaction mixture 0.057 g triethylamine, 15 ml ethyl acetate, 5 ml of brine and 5 ml water were successively added, then the organic layer was separated. The organic layer was then dried (MgSO$_4$), and the solvent was evaporated. The resulting residue was passed through a silica gel column and eluted with hexane-ethyl acetate (2:1), then the eluted fraction containing the desired product was collected and concentrated under reduced pressure to yield 0.038 g of the subject compound (35) in the form of a powder.

IR$\nu_{max}^{neat}$ cm$^{-1}$: 1755, 1712

NMR(90 MHz, CDCl$_3$)δ: 0.31(3H, s), 0.33(3H, s), 1.00(9H, s), 2.93(1H, dd, J=2 Hz, 16 Hz), 3.77(1H, dd, J=5 Hz, 16 Hz), 5.35(1H, dd, J=2 Hz, 5Hz)

Reference Example 36

Production of 1-(t-butyldimethylsilyl)-2-azetidinone-4-thiol

[Compound (36)]

0.3 g 1-(t-butyldimethylsilyl)-4-tritylthio-2-azetidinone was dissolved in 2 ml dichloromethane; the resulting solution was cooled to −78° C. and stirred. To this solution 10 ml of a solution of 0.25 g mercuric acetate in methanol was added, then the solution was stirred for 20 minutes. Hydrogen sulfide gas was passed through the reaction mixture at −78° C. for 15 minutes, then the reaction mixture was warmed to 0° C. while passing nitrogen gas. The solvent was then evaporated under reduced pressure, and the resulting residue, after adding 10 ml dichloromethane, was filtered to remove insoluble substances. The resulting filtrate was concentrated under reduced pressure, and the resulting residue was passed through a silica gel column and eluted with ethyl acetate-hexane (1:4). The eluted fraction containing the desired product was then collected and concentrated under reduced pressure to yield 0.093 g of the subject compound (36) in the form of an oily substance.

IR$\nu_{max}^{neat}$ cm$^{-1}$: 2545, 1742, 1467, 1294, 1250, 1173

NMR(90 MHz, CDCl$_3$)δ: 0.30(6H, s), 0.99(9H, s), 2.18(1H, d, J=8 Hz), 2.95(1H, dd, J=3 Hz, 16 Hz), 3.63(1H, dd, J=6 Hz, 16 Hz), 4.78(1H, m)

Reference Example 37

Production of di-5-(t-butyl)-1-(4-nitrobenzyl)3-[1-(t-butyldimethylsilyl)-2-azetidinone-4-yl]thio-2-oxoglutarate

[Compound (37)

0.07 g of the compound (36) obtained in Reference Example 36 was dissolved in 1 ml dichloromethane in nitrogen gas flow. While cooling this solution, a solution of 1 ml N,N-dimethylacetamide and 0.116 g of the compound (19) obtained in Reference Example 19 in 1 ml dichloromethane and 0.0306 g pyridine were added, then the resulting mixed solution was stirred for 20 minutes while cooling with ice. The reaction mixture, after adding 10 ml ethyl acetate, was washed with water and dried (MgSO$_4$), then the solvent was evaporated under reduced pressure. The resulting residue was passed through a silica gel column and eluted with dichloromethane and then with ethyl acetate-hexane (1:3); then the eluted fraction containing the desired product was collected and concentrated under reduced pressure to yield 0.099 g of the subject compound (37) in the form of an oily substance.

IR$\nu_{max}^{neat}$ cm$^{-1}$: 1750, 1726, 1526, 1347, 1250, 1160

Reference Example 38

Production of (4-nitro)benzyl 2-hydroxy-3-(t-butyloxycarbonylmethyl)-7-oxo-4-thia-1-azabicyclo[3,2,0]heptane-2-carboxylate

[Compound (38)]

0.099 g of the compound (37) obtained in Reference Example 37 was dissolved in 1 ml N,N-dimethylacetamide. To this solution 0.1 ml water and 4 drops of 2N hydrochloric acid were added, then the solution was stirred at room temperature for 1 hour. The reaction mixture was extracted with 5 ml ethyl acetate. The organic layer was washed with water and dried (MgSO$_4$), then the solvent was evaporated under reduced pressure. The resulting residue was passed through a silica gel column and eluted with acetic acid-hexane (2:3); the eluted fraction containing the desired product was collected and concentrated under reduced pressure to yield 0.066 g of the subject compound (38) in the form of oily substance.

IR$\nu_{max}^{neat}$ cm$^{-1}$: 3350, 1775, 1745, 1725, 1514, 1345

Reference Example 39

Production of 1-(4-nitrobenzyl) 3-(2-azetidinon-4-yl)thio-2-oxoglutarate

[Compound (39)]

0.107 g of the compound (36) obtained in Reference Example 36 was dissolved in a mixture of 2 ml acetone and 1 ml hexamethylphosphoramide in nitrogen gas flow. To this solution 0.177 g of the compound (18) obtained in Reference Example 18 was added, then the solution was stirred at room temperature for 2 hours. The reaction mixture, after adding 3 ml 1N hydrochloric acid, was stirred for 45 minutes, after which it was extracted with 10 ml ethyl acetate. The organic layer was washed with water and dried (MgSO$_4$), then the solvent was evaporated to yield the subject compound (39) in the form of a crude oily substance, which was used as a starting material for Example 8 without purification.

Reference Example 40

Production of (3S,4R)-3-[(1R)-1-(t-butyldimethylsilyloxy)ethyl]-4-tritylthio-2-azetidinone[Compound (40)]

1.02 g (3S,4R)-3-[(1R)-1-(t-butyldimethylsilyloxy)ethyl]-4-phenylsulfonyl-2-azetidinone was dissolved in 17 ml methanol. While cooling this solution with ice, a solution of 0.915 g tritylmercaptane in a mixture of 25 ml methanol and 8 ml tetrahydrofuran was added. The resulting mixed solution was stirred at room temperature for 35 minutes, then the solvent was evaporated under reduced pressure. The resulting residue, after dissolving in ethyl acetate, was washed with water and dried (MgSO$_4$), then the solvent was evaporated under reduced pressure. The resulting residue was passed through a silica gel column and eluted with ethyl acetate-hexane (1:6), then the eluted fraction containing the desired product was collected and concentrated under reduced pressure to yield 1.27 g of the subject compound (40) in the form of a powder.

IR$\nu_{max}^{KBr}$ cm$^{-1}$: 3400, 1765

NMR(90 MHz, CDCl$_3$)δ: 0.07(6H, s), 0.82(9H, s), 1.33(3H, d, J=6.3 Hz), 3.19(1H, t, J=2.7 Hz), 4.31(1H, dq, J=2.7 Hz, 6.3 Hz), 4.51(1H, br, s), 4.63(1H, d, J=3 Hz), 6.9–8.0(15 H, m)

Reference Example 41

Production of (3S,4R)-1-(t-butyldimethylsilyl)-3-[(1R)-1-(t-butyldimethylsilyloxy)ethyl]-4-tritylthio-2-azetidinone

[Compound (41)]

4.55 g of the compound (40) obtained in Reference Example 40 was dissolved in 20 ml dichloromethane. To this solution 1.47 ml triethylamine and then 2.22 ml t-butyldimethylsilyl tryphlate were added in nitrogen gas flow, while cooling the solution with ice. The resulting mixed solution was stirred for 20 minutes while cooling with ice. The reaction mixture was poured into 100 ml ice water and extracted with 120 ml dichloromethane. The organic layer was successively washed with a saturated aqueous solution of sodium bicarbonate and water and dried (MgSO$_4$), then the solvent was evaporated under reduced pressure. The resulting residue was passed through a silica gel column and eluted with ethyl acetate-hexane (1:10), then the eluted fraction containing the desired product was collected and concentrated under reduced pressure to yield 5.11 g of the subject compound in the form of an oily substance.

IR$\nu_{max}^{neat}$ cm$^{-1}$: 1755, 1465, 1290, 1250,

Reference Example 42

Production of (3S,4R)-1-(t-butyldimethylsilyl)-3-[(1R)-1-(t-butyldimethylsilyloxy)ethyl]-4-mercapto-2-azetidinone

[Compound (42)]

4.55 g of the compound (41) obtained in Reference Example 41 was dissolved in 130 ml methanol; the resulting solution was cooled to −60° C. and stirred. To this solution a solution of 3.05 g mercuric acetate in 85 ml methanol was added dropwise. 40 minutes later, a solution of 469 mg mercuric acetate in 5 ml methanol was further added, and the resulting mixed solution was stirred for 30 minutes. The reaction mixture was cooled to −78° C., through which hydrogen sulfide gas was passed for 5 minutes. Nitrogen gas was then passed through the reaction mixture at room temperature for 45 minutes, then the solvent was evaporated under reduced pressure. The resulting residue, after adding dichloromethane, was filtered to remove insoluble substances; the resulting filtrate was concentrated under reduced pressure. The resulting residue was passed through a silica gel column and eluted with ethyl acetate-hexane (1:20), then the eluted fraction containing the desired product was collected and concentrated under reduced pressure to yield 2.04 g of the subject compound (42) in the form of a powder.

IR$\nu_{max}^{KBr}$ cm$^{-1}$: 2500, 1730, 1470, 1250

NMR (90 MHz, CDCl$_3$)δ: 0.0~0.1(3H×3,3 s), 0.89(9H, s), 1.00(9H, s), 1.22(3H, d, J=6.3 Hz), 2.11(1H, d, J=8.7 Hz), 3.07(1H, dd, J=3 Hz, 3 Hz), 4.2(1H, m), 4.83(1H, dd, J=8.7 Hz, 3.0 Hz)

Reference Example 43

Production of 1-(4-nitrobenzyl) 3-{(3S,4R)-3-[(1R)-1-hydroxylethyl-2-azetidinon-4-yl}thio-2-oxoglutarate [Compound (43)]

1.78 g of the compound (42) obtained in Reference Example 42 was dissolved in 25 ml acetone. To this solution 1.80 g pyridine, 50 ml hexamethylphosphoramide and then a solution of 2.39 g of the compound (18) obtained in Reference Example 18 in 25 ml aetone were added; the resulting mixed solution was stirred at room temperature for 4 hours. The reaction mixture, after adding 50 ml 2N hydrochloric acid while cooling the liquid with ice, was stirred. After 1 hour of agitation, 40 ml 2N hydrochloric acid was further added, then the solution was stirring for 3 hours. The reaction mixture was poured into water and extracted with ethyl acetate; the organic layer was washed with water and dried (MgSO$_4$), then the solvent was evaporated under reduced pressure to yield 5.04 g of a crude product of the subject compound (43) in the form of a powder.

Reference Example 44

Production of 1-(4-bromobenzyl)3-bromo-2-oxoglutarate [Compound (44)]

3.0 g of 1-(4-bromobenzyl) 2-oxoglutarate synthesized in accordance with the production procedure of Reference Example 3 was dissolved in 25 ml dry chloroform. While heating to 50° to 60° C. and stirring this solution, 10 ml of a solution of 0.54 ml bromine in dry chloroform was gradually added dropwise over a period of 6 hours. The reaction mixture was cooled to room temperature. After adding 100 ml dichloromethane, the mixture was washed with brine and dried (MgSO$_4$), then the solvent was evaporated under reduced pressure to yield 3.6615 g of the subject compound (44) in the form of a light yellow oily substance.

IR$\nu_{max}^{neat}$ cm$^{-1}$: 3360, 3000, 1800, 1740, 1595, 1490, 1405, 1280, 1210, 1070, 1010

NMR (90 MHz, CDCl$_3$)δ: 2.88–3.50(2H, m), 5.19–5.41(3H, m), 7.26 and 7.51(4H, 2 d, J=9 Hz), 9.43(1H, br)

Reference Example 45

Production of 1-(4-bromobenzyl)2-oxo-3-[(3R,4R)-3-phenoxyacetamido-2-azetidinon-4-yl]thioglutarate [Compound (45)]

252 mg (3R,4R)-4-mercapto-3-phenoxyacetamido-2-azetidinone and 430 mg of the compound (44) obtained in Reference Example 44 were suspended in 5 ml acetone. After 10 minutes of stirring at room temperature, this suspension was diluted with 5 ml hexamethylphosphoramide and stirred for 1 hour and 10 minutes. The reaction mixture, after adding 10 ml water, was extracted with ethyl acetate. The organic layer was washed with water and dried (MgSO$_4$), then the solvent was evaporated under reduced pressure to yield 764 mg of a crude product of the subject compound (45) in the form of a powder.

Reference Example 46

Production of 1-(4-bromo)benzyl 2-oxo-3-[(3R,4R)-3-phenylacetamido-2-azetidinon-4-yl]thioglutarate [Compound (46)]

709 mg (3R,4R)-4-mercapto-3-phenylacetamido-2-azetidinone and 1.247 g of the compound (44) as obtained in Reference Example 44 were suspended in 7 ml acetone. After stirring the resulting suspension at room temperature for 10 minutes, 7 ml hexamethylphosphoramide was added, and the suspension was stirred for 1.5 hours. The reation mixture, after adding water, was extracted with ethyl acetate. The organic layer was washed with water and dried (MgSO$_4$), then the solvent was distilled off under reduced pressure to yield 1.571 g of a crude product of the subject compound (46) in the form of a light yellow powder.

Reference Example 47

Production of 1-diphenylmethyl 3-bromo-2-oxoglutarate

[Compound (47)]

5.082 g of a crude product of 3-bromo-2-oxoglutaric acid obtained via the method described in Biochemistry, 20, 894 (1981) was dissolved in 50 ml dichloromethane. While cooling with ice and stirring the resulting solution, 25 ml of a solution of 3.989 g diphenyldiazomethane in dichloromethane was gradually added dropwise over a period of 45 minutes. After 15 minutes of stirring at the same temperature, the reaction mixture was concentrated under reduced pressure. The resulting residue was passed through a silica gel column and eluted with ethyl acetate-hexane-acetic acid (30:70:1), then the fraction containing the desired product was collected and concentrated under reduced pressure. The obtained light yellow oily substance was dissolved in 200 ml dichloromethane, washed with a brine and dried (MgSO$_4$), then the solvent was distilled off under reduced pressure to yield 4.863 g of the subject compound (47) in the form of a light yellow oily substance.

IRv$_{max}^{neat}$ cm$^{-1}$: 3025, 1800, 1730, 1495, 1450, 1405, 1270, 1095, 1025, 940, 760, 745, 695, NMR (90 MHz, CDCl$_3$)δ: 2.91–3.45(2H, m), 4.90–5.40(1H, br), 5.90–6.50(1H, br), 6.97(1H, S), 7.33(10H, S)

Reference Example 48

Production of 1-diphenylmethyl 2-oxo-3-[(3R,4R)-3-phenylacetamido-2-acetidinon-4-yl]thioglutarate [Compound (48)]

1.182 g (3R,4R)-4-mercapto-3-phenylacetamido-2-azetidinone and 2.159 g of the compound (47) as obtained in Reference Example 47 were suspended in 20 ml acetone. After stirring the resulting suspension at room temperature for 10 minutes, 20 ml hexamethylphosphoramide was added, and the suspension was stirred for 1 hour and 25 minutes. The reaction mixture, after adding water, was extracted with ethyl acetate. The organic layer was washed with water and dried (MgSO$_4$), then the solvent was evaporated under reduced pressure to yield 2.8385 g of a crude product of the subject compound (48) in the form of a light yellow powder.

Reference Example 49

Production of 1-diphenylmethyl 2-oxo-3-[(3R,4R)-3-phenoxyacetamido-2-azetidinon-4-yl]thioglutarate [Compound (49)]

1.262 g (3R,4R)-4-mercapto-3-phenoxyacetamido-2-azetidinone and 2.135 g of the compound (47) as obtained in Reference Example 47 were suspended in 20 ml acetone. After stirring the resulting suspension at room temperature for 10 minutes, 20 ml hexamethylphosphoramide was added, and the suspension was stirred for 1.5 hours. The reaction mixture, after adding water, was extracted with ethyl acetate. The organic layer was washed with water and dried (MgSO$_4$), then the solvent was evaporated under reduced pressure to yield 2.883 g of a crude product of the subject compound (49) in the form of a light yellow powder.

EXAMPLE 1

Production of 4-nitrobenzyl(2S,6R,8R,9R)-4,10-dioxo-9-phenylacetamido-3-oxa-7-thia-1-azatricyclo[6,2,0,0$^{2,6}$]-decane-2-carboxylate 3.603 g of the crude compound (23) obtained in Reference Example 23 was dissolved in 40 ml dichloromethane. To this solution 1.760 g dicyclohexylcarbodiimide was added in nitrogen gas flow, then the solution was stirred at room temperature for 3 hours. To the reaction mixture 50 ml ethyl acetate was added, and the separating dicyclohexylurea was removed via filtration. The resulting filtrate was concentrated under reduced pressure. The resulting residue was passed through a silica gel column and eluted with n-hexane-ethyl acetate (1:1), then the eluted fraction containing the desired product was collected and concentrated under reduced pressure to yield 308 mg of the subject compound in the form of a light brown powder.

[α]$_D^{22}$+157.6° (c=0.425, CHCl$_3$)

FDMS m/z: 497(M$^+$)

IRv$_{max}^{KBr}$ cm$^{-1}$: 3350, 3025, 1790, 1755, 1675, 1515, 1350

NMR (400 MHz, CDCl$_3$)δ: 2.93(1H, dd, J=2.69 Hz, 18.8 Hz), 3.18(1H, dd, J=8.54 Hz, 18.8 Hz), 3.64(2H, ABq, =Δδ0.045 ppm, J=16.1 HZ), 4.94(1H, dd, J=2.69 Hz, 8.54 Hz), 5.39(2H, ABq, J=12.9 Hz), 5.53(1H, d, J=4.39 Hz), 5.65(1H, dd, J=4.39 Hz, 8.79 Hz), 6.09(1H, d, J=8.79 Hz), 7.22–7.29 and 7.30–7.41(5H, m), 7.56 and 8.24(4H, 2 d, J=8.79 Hz)

EXAMPLE 2

Production of sodium (2S,6R,8R,9R)-4,10-dioxo-9-phenylacetamido-3-oxa-7-thia-1-azatricyclo[6,2,0,0$^{2,6}$]decane-2-carboxylate:

187 mg of the compound obtained in Example 1 was dissolved in a mixed solvent of 6.5 ml ethyl acetate and 8 ml of a 0.1M phosphate buffer solution (pH 7.0). To this solution 149 mg of 10% (W/W) palladium carbon was added, while cooling the solution with ice, then hydrogen gas was passed through the solution while stirring the solution. 45 minutes, 90 minutes and 135 minutes after the initiation of reaction, 74 mg of 10% (W/W) palladium carbon was added, and hydrogen gas was passed through the solution for 3 hours in total, while ice-cooling and stirring the solution. The reaction mixture was filtered; the resulting filtrate was extracted with 10 ml ethyl acetate. The water layer was separated, from which ethyl acetate was evaporated undr reduced pressure. The resulting residue was passed through a column packed with Amberlite XAD-2. The fraction eluted with water-ethanol (95:5) was collected, and ethanol was evaporated under reduced pressure. The fraction was then lyophilized to yield 88 mg of the subject compound in the form of a pale yellow powder. Melting point: 150° to 154° C. (decomposed)

SIMS m/z: 385(MH+)

IRv$_{max}^{KBr}$ cm$^{-1}$: 3400, 1780, 1655, 1540, 1390, 1200

NMR(270 MHz, D$_2$O)δ: 3.03(1H, dd, J=4.8 Hz, 19.5 Hz), 3.34(1H, dd, J=9.3 Hz, 19.5 Hz), 3.70(2H, s), 4.92(1H, dd, J=4.8 Hz, 9.3 Hz), 5.48(1H, d, J=4.2 Hz), 5.67(1H, d, J=4.2 Hz), 7.34-7.45(5H, m)

EXAMPLE 3

Production of (4-nitro)benzyl (2S,6R,8R,9R)-4,10-dioxo-9-phenoxyacetamido-3-oxa-7-thia-1-azatricyclo[6,2,0,0$^{2,6}$]decane-2-carboxylate:

(a) 9.80 g of the crude compound (24) obtained in Reference Example 24 was dissolved in 150 ml dichloromethane. To this solution 4.932 g dicyclohexylcarbodiimide was added in nitrogen gas flow, then the solution was stirred at room temperature for 3 hours. To the reaction mixture 100 ml ethyl acetate was added; separating dicyclohexylurea was removed via filtration. The resulting filtrate was concentrated under reduced pressure. The resulting residue was passed through a silica gel column and eluted with n-hexane-ethyl acetate (1:1), then the eluted fraction containing the desired product was collected and concentrated under reduced pressure to yield 519.5 mg of the subject compound in the form of a white powder. Melting point: 174° to 177° C. (decomposed)

[α]$_D^{21}$ +120.8° (c=0.255, THF)

FDMS m/z: 513(M+)

IRv$_{max}^{KBr}$ cm$^{-1}$: 3440, 2960, 2930, 1805, 1785, 1765, 1690, 1520 1500, 1350, 1305, 1225

NMR (270 MHz, d$_6$-DMSO)δ: 2.96(1H, dd, J=5.0 Hz, 18.5 Hz), 3.30(1H, dd, J=8.9 Hz, 18.5 Hz), 4.63(2H, s) 5.07(1H, dd, J=5.0 Hz, 8.9 Hz), 5.41(2H, ABq, J=13.9 Hz), 5.58(1H, dd, J=4.3 Hz, 7.6 Hz), 5.76(1H, d, J=4.3 Hz), 6.88-6.98 and 7.26-7.31(5H, m), 7.73 and 8.26(4H,2 d, J=8.9 Hz), 8.89(1H, d, J=7.6 Hz)

(b) 490 mg of the crude compound (24) obtained in Reference Example 24 and 131 mg triphenylphosphine were dissolved in 5 ml dichloromethane. To this solution 1 ml of a solution of 110 mg 2,2'-dipyridylsufide in dichloromethane was added; the resulting mixed solution was stirred at room temperature for 1 hour. The reaction mixture was concentrated under reduced pressure; the resulting residue was passed through a silica gel column and eluted with ethyl acetate-hexane(9:11).- The eluted fraction containing the desired product was collected and concentrated under reduced pressure to yield 18.5 mg of the subject compound, whose NMR spectrum was identified with that of the compound obtained in (a) above.

(c) 490 mg of the crude compound (24) obtained in Reference Example 24 was dissolved in 4 ml dichloromethane. To this solution 40 μl thionyl chloride was added, while cooling the solution with ice, then the solution was stirred at the same temperature for 10 minutes. The reaction mixture was passed through a silica gel column and eluted with ethyl acetate-hexane (1:1). The eluted fraction containing the desired product was collected and concentrated under reduced pressure to yield 5.5 mg of the subject compound, whose NMR spectrum was identified as that of the compound obtained in (a) above.

EXAMPLE 4

Production of sodium (2S,6R,8R,9R)-4,10-dioxo-9-phenoxyacetamido-3-oxa-7-thia-1-azatricyclo[6,2,0,0$^{2,6}$]decane-2-carboxylate:

217 mg of the compound obtained in Example 3 was suspended in a mixed solvent of 20 ml ethyl acetate and 20 ml of a 0.1M phosphate buffer solution (pH 7.0). To this suspension 167 mg of 10% palladium carbon was added, while cooling the suspension with ice, then hydrogen gas was passed through the suspension. 45 minutes, 135 minutes and 220 minutes after the initiation of reaction, 84 mg of 10% palladium carbon was added. The reaction mixture was filtered; the water layer of the resulting filtrate was concentrated under reduced pressure to remove ethyl acetate. The resulting aqueous solution was passed through a column packed with Amberlite XAD-2 and eluted with water-ethanol (95:5). The eluted fraction containg the desired product was collected and evaporated under reduced pressure to remove ethanol, after which it was lyophilized to yield 71 mg of the subject compound in the form of a white powder. Melting point: 149° to 152° C. (decomposed)

SIMS m/z: 401(MH+)

IRv$_{max}^{KBr}$ cm$^{-1}$: 3400, 1780, 1660, 1600, 1525, 1495, 1380, 1295, 1220

NMR (400 MHz, D$_2$O)δ: 3.02(1H, dd, J=4.5 Hz, 19.5 Hz), 3.33(1H, dd, J=9.5 Hz, 19.5 Hz), 4.74(2H, s), 4.91(1H, dd, J=4.5 Hz, 9.5 Hz), 5.59(1H, d, J=4.2 Hz), 5.70(1H, d, J=4.2 Hz), 7.00-7.12 and 7.36-7.42(5H, m)

EXAMPLE 5

Production of methyl (2S,6R,8R,9R)-4,10-dioxo-9-phenoxyacetamido-3-oxa-7-thia-1-azatricyclo[6,2,0,0$^{2,6}$]decane-2-carboxylate:

30 mg of the compound obtained in Example 4 was dissolved in 3 ml water. To this solution 3 ml ethyl acetate and 5 ml of diazomethane in ether were added, while cooling the solution with ice. After adding 83 μl of 1N hydrochloric acid, the resulting mixed solutio was stirred for 30 minutes, while cooling with ice. After 30 minutes of stirring, 8 ml of a solution of diazomethane in ether was added; the resulting mixed solution was stirred for 20 minutes, while cooling with ice. The reaction mixture, after dilution with water, was extracted with ethyl acetate. The organic layer was dried (MgSO$_4$), then the solvent was evaporated under reduced pressure. The resulting residue was passed through a silica gel column and eluted with n-hexane-ethyl acetate (2:1), then the eluted fraction containing the desired product was collected and concentrated under reduced pressure to yield 13.5 mg of the subject compound in the form of a white crystal. Melting point: 182° to 184° C.

FDMS m/z: 392(M+)

IRv$_{max}^{KBr}$ cm$^{-1}$: 3410, 1815, 1795, 1755, 1700, 1520, 1500

NMR (270 MHz, d$_6$-DMSO)δ: 2.99(1H, dd, J=5.3 Hz, 18.5 Hz), 3.26(1H, dd, J=9.2 Hz, 18.5 Hz), 3.80(3H, s), 4.63(2H, s), 5.01(1H, dd, J=5.3 Hz, 9.2 Hz), 5.57(1H, dd, J=4.3 Hz, 7.9 Hz), 5.73(1H, d, J=4.3 Hz), 6.89-6.99 and 7.26-7.32(5H, m), 8.99(1H, d, J=7.9 Hz)

EXAMPLE 6

Production of (4-nitro)benzyl (2S,6R,8R,9R)-4,10-dioxo-9-[(2R)-2-(4-ethyl-2,3-dioxo-1-piperazinecarboxamido)phenylacetamido]-3-oxa-7-thia-1-azatricyclo[6,2,0,0$^{2,6}$]decane-2-carboxylate:

1.4415 g of the crude compound (34) obtained in Reference Example 34 was dissolved in 30 ml dichloromethane. To this solution 295 mg dicyclohexylcarbodiimide was added, then the solution was stirred at room temperature in nitrogen gas flow. To the reaction mixture 10 ml ethyl acetate was added; the precipitating dicyclohexylurea was removed via filtration. The resulting filtrate was concentrated under reduced pressure. The resulting residue was passed through a silica gel column and eluted with ethyl acetate-n-hexane (8:2), then the eluted fraction containing the desired product was collected and concentrated under reduced pressure to yield 53 mg of the subject compound in the form of a white powder.

FDMS m/z: 681(M+)

IR$\nu_{max}^{KBr}$ cm$^{-1}$: 3290, 2970, 1790, 1755, 1710, 1680, 1605 1520, 1350, 1180

NMR (270 MHz, CDCl$_3$)δ: 1.22(3H, t, J=7.3 Hz), 2.89(1H, dd, J=3.0 Hz, 18.8 Hz), 3.16(1H, dd, J=8.3 Hz, 18.8 Hz), 3.52-3.60(4H, m), 4.02-4.09(2H, m), 4.91(1H, dd, J=3.0 Hz, 8.3 Hz), 5.39(2H, ABq, J=12.9 Hz), 5.43(1H, d, J=6.3 Hz), 5.50(1H, d, J=4.3 Hz), 5.67(1H, dd, J=4.3 Hz, 8.9 Hz), 6.54(1H, d, J=8.9 Hz), 7.39(5H, s). 7.57 and 8.24(4H, 2d, J=8.6 Hz), 9.91(1H, d, J=6.3 Hz)

EXAMPLE 7

Production of sodium (2S,6R,8R,9R)-4,10-dioxo-9-[(2R)-2-(4-ethyl-2,3-dioxo-1-piperazinecarboxamido)phenylacetamido]-3-oxa-7-thia-1-azatricyclo[6,2,0,0$^{2,6}$]decane-2-carboxylate:

214.5 mg of the compound obtained in Example 6 was dissolved in a mixed solvent of 8 ml ethyl acetate and 10 ml of a 0.1M phosphate buffer solution (pH 7.0). The resulting solution, after adding 125 mg 10% palladium carbon while cooling the solution with ice, was stirred, while passing hydrogen gas through the solution. 45 minutes, 90 minutes and 135 minutes after the initiation of reaction, 63 mg 10% palladium carbon was added. The solution was stirred for 300 minutes in total, while passing hydrogen gas through the solution. The reaction mixture was filtered, and the resulting filtrate was extracted with ethyl acetate. The water layer was concentrated under reduced pressure to remove the coexisting ethyl acetate. The resulting aqueous solution was passed through a column packed with Amberlite XAD-2 and eluted with water-ethanol (95:5), then the eluted fraction containing the desired product was collected and concentrated under reduced pressure, after which it was lyophilized to yield 101.5 mg of the subject compound in the form of a white powder.

Melting point: 188° to 191° C. (decomposed)

SIMS m/z: 568(MH+)

IR$\nu_{max}^{KBr}$ cm$^{-1}$: 3400, 1780, 1715, 1675, 1510, 1365, 1190

NMR (270 MHz, D$_2$O)δ: 1.20(3H, t, J=7.3 Hz), 2.95(1H, dd, J=4.6 Hz, 19.5 Hz), 3.30(1H, dd, J=9.6 Hz, 19.5 Hz), 3.52(2H, q, J=7.3 Hz), 3.68-3.74 and 4.01-4.08(4H, m), 4.82(1H, dd, J=4.6 Hz, 9.6 Hz), 5.51(1H, s), 5.53(1H d, J=4 Hz), 5.61(1H, d, J=4.0 Hz), 7.51(5H, s)

EXAMPLE 8

Production of (4-nitro)benzyl 4,10-dioxo-3-oxa-7-thia-1-azatricyclo[6,2,0,0$^{2,6}$]decane-2-carboxylate:

The crude compound (39) obtained in Reference Example 39 was dissolved in 5 ml dichloromethane. To this solution 0.191 g dicyclohexylcarbodiimide was added in nitrogen gas flow, then the solution was stirred at room temperature for 1.5 hours. The solvent of the reaction mixture was evaporated under reduced pressure; to the resulting residue 10 ml ethyl acetate was added. Insoluble substances were removed via filtration; the resulting filtrate was concentrated under reduced pressure. The rsulting concentrate residue was passed through a silica gel column and eluted with ethyl acetate-hexane (1:1), then the eluted fraction containing the desired product was collected and concentrated under reduced pressure to yield 0.035 g of the subject compound in the form of a powder.

IR$\nu_{max}^{KBr}$ cm$^{-1}$: 1788, 1760, 1520, 1346, 1196, 1171, 1035

FDMS m/z: 364(M+)

NMR (90 MHz, CDCl$_3$)δ: 2.87(1H, dd, J=4 Hz, 18 Hz), 3.13(1H, dd, J=2 Hz, 16 Hz), 3.20(1H, dd, J=8 Hz, 18 Hz), 3.60(1H, dd, J=4 Hz, 16 Hz), 5.08(1H, dd, J=4 Hz, 8 Hz), 5.37(1H. dd, J=2 Hz, 4 Hz), 5.41(2H, ABq, J=13 Hz, 17 Hz), 7.58(2H, d, J=9 Hz), 8.24(2H, d, J=9 Hz)

EXAMPLE 9

Production of sodium 4,10-dioxo-3-oxa-7-thia-1-azatricyclo[6,2,0,0$^{2,6}$]decane-2-carboxylate:

0.15 g of the compound obtained in Example 8 was suspended in a mixture of 5 ml ethyl acetate and 4 ml of a (0.1M) phosphate buffer solution (pH 7.0). To this suspension 0.15 g of 10% palladium carbon was added, while cooling the suspension with ice, then the suspension was stirred in hydrogen gas flow for 1.5 hours. To the reaction mixture 0.15 g of 10% palladium carbon was added, then the mixture was stirred in hydrogen gas flow for 2 hours, after which it was filtered to remove insoluble substances. The water layer of the resulting filtrate was passed through a column packed with Amberlite XAD-2 and eluted with water, then the eluted fraction containing the desired product was collected and lyophilized to yield 0.069 g of the subject compound in the form of a powder.

IR$\nu_{max}^{KBr}$ cm$^{-1}$: 3450, 1806, 1795, 1783, 1770, 1625

NMR (90 MHz, D$_2$O)δ: 3.08(1H, dd, J=6 Hz, 19 Hz), 3.26(1H, dd, J=2 Hz, 17 Hz), 3.42(1H, dd, J=9 Hz, 19 Hz), 3.63(1H, dd, J=4 Hz, 17 Hz), 5.05(1H, dd, J=6 Hz, 9 Hz), 5.54(1H. dd, J=2 Hz, 4 Hz)

EXAMPLE 10

Production of (4-nitro)benzyl (8R,9S)-4,10-dioxo-9-[(1R)-1-hydroxy]ethyl-3-oxa-7-thia-1-azatricyclo[6,2,0,0$^{2,6}$]decane-2-carboxylate:

5.04 g of the compound (43) obtained in Reference Example 43 was dissolved in 150 ml dichloromethane. To this solution 1.53 g 1-(3-dimethylaminopropyl)-3-ethylcarbodiimide hydrochloride was added at 0° C. in nitrogen gas flow, then the solution was stirred at room temperature for 1 hour. The solvent was evaporated under reduced pressure. The resulting residue, after adding 20 ml ethyl acetate, was washed with water and dried (MgSO$_4$), then the solvent was evaporated. The resulting residue was passed through a silica gel column and eluted with ethyl acetate-hexane (2:3), then the eluted fraction containing the desired product was collected and concentrated under reduced pressure to yield 272 mg of the subject compoundin the form of a crystal.

Melting point: 170.5° to 172.0° C. (decomposed)
Elemental analysis (as $C_{17}H_{16}N_2O_8S$):
Calculated: C, 50.00; H, 3.95; N, 6.86
Found: C, 50.12; H, 4.03; N, 6.76
IR$\nu_{max}^{KBr}$ cm$^{-1}$: 3480, 1805, 1770, 1520, 1345, 1050
NMR(400 MHz, d$_6$-DMSO)$\delta$: 1.126(3H, d, J=6.35 Hz), 3.335(1H, dd, J=7.33 Hz, 18.56 Hz),
3.216(1H, dd, J=10.01 Hz, 18.55 Hz),
3.421(1H, dd, J=1.71 Hz, 5.49 Hz), 3.998(1H, m),
5.140(1H, dd, J=7.33 Hz, 10.01 Hz), 5.227(1H, d, J=4.89 Hz),
5.376(2H, dd, J=13.67 Hz, 57.37 Hz), 5.554(1H, d, J=1.71 Hz), 7.989(4H, ABq, J=8.79 Hz)

EXAMPLE 11

Production of sodium (8R,9S)-4,10-dioxo-9-[(1R)-1-hydroxy]ethyl-3-oxa-7-thia-1-azatricyclo[6,2,0,0$^{2,6}$]decane-2-carboxylate 192.7 mg of the compound obtained in Example 10 was dissolved in a mixture of 7 ml ethyl acetate and 8 ml of a 0.1M phosphate buffer solution (pH 7.0). In the presence of 187 mg of 10% palladium carbon, hydrogen gas was passed through this solution, which was then stirred. 55 minutes and 105 minutes after the initiation of reaction, 94 mg of 10% palladium carbon was added. After in total 2.5 hours of reaction, the reaction mixture was filtered to remove insoluble substances. The water layer of the resulting filtrate was passed through a column packed with Amberlite XAD-2 and eluted with water, then the eluted fraction containing the desired product was collected and lyophilized to yield 73 mg of the subject compound in the form of a powder.

Elemental analysis (as $C_{10}H_{10}NO_6SNa$):
Calculated: C, 50.00; H, 3.95; N, 6.86
Found: C, 50.12; H, 4.13; N, 6.76
IR$\nu_{max}^{KBr}$ cm$^{-1}$: 3400, 1770, 1650
NMR(90 MHz, D$_2$O)$\delta$: 1.4(3H, d, J=6.3 Hz), 3.10(1H, dd, J=6.0 Hz, 19.5 Hz), 3.47(1H, dd, J=9 Hz, 19.5 Hz), 3.66(1H, dd, J=1.8 Hz, 5.7 Hz), 4.36(1H, m), 5.07(1H, dd, J=6.0 Hz, 9.0 Hz), 5.53(1H, d, J=1.8 Hz),

EXAMPLE 12

Production of (4-bromo)benzyl (2S,6R,8R9R)-4,10-dioxo-9-phenoxyacetamido-3-oxa-7-thia-1-azatricyclo[6,2,0,0$^{2,6}$]decane-2-carboxylate (isomer A) and (4-bromo)benzyl (2R,6S,8R,9R)-4,10-dioxo-9-phenoxyacetamido-3-oxa-7-thia-1-azatricyclo[6,2,0,0$^{2,6}$]-decane-2-carboxylate (isomer B)

(a) 764 mg of a crude product of the compound (45) obtained in Reference Example 45 was dissolved in 10 ml dichloromethane. To this solution 230 mg N-ethyl-N'-[3-(dimethylamino)propyl]-carbodiimide hydrochloride was added in nitrogen gas flow, then the solution was stirred at room temperature for 2.5 hours. The reaction mixture, after adding 50 ml dichloromethane, was washed with water, and the organic layer was dried (over MgSO$_4$), then the solvent was evaporated under reduced pressure. The resulting residue was passed through a silica gel column and eluted with ethyl acetate-hexane (9:11), then the eluted fraction containing the desired product was collected and concentrated under reduced pressure to yield isomers-A (as white crystals, 72.5 mg) and -B (as an oily substance, 50.5 mg) of the subject compound.

Isomer-A
Melting point: 175° to 178° C. (decomposed)
IR$\nu_{max}^{KBr}$ cm$^{-1}$: 3430, 1810, 1790, 1760, 1690, 1595, 1520, 1495, 1435, 1300, 1230, 1050
NMR(270 MHz, d$_6$-DMSO)$\delta$: 3.00(1H, dd, J=4.6 Hz, 18.5 Hz), 3.26(1H, dd, J=8.9 Hz, 18.5 Hz), 4.63(2H, s), 5.03(1H, dd, J=4.6 Hz, 8.9 Hz), 5.24(2H, ABq, J=12.5 Hz), 5.58(1H, dd, J=4.3 Hz), 5.74(1H, d, J=4.3 Hz), 6.89-6.99 and 7.26-7.32(5H, m), 7.41 and 7.60(4H, 2d, J=8.3 Hz), 8.88(1H, d, J=7.9 Hz)

Isomer-B
IR$\nu_{max}^{CHCl_3}$ cm$^{-1}$: 3430, 1820, 1770, 1700, 1600, 1515, 1495, 1275, 1075
NMR(270 MHz, d$_6$-DMSO)$\delta$: 3.04(1H, dd, J=4.3 Hz, 19.1 Hz), 3.26(1H, dd, J=8.6 Hz, 19.1 Hz), 4.61(2H, s) 4.91(1H, dd, J=4.3 Hz, 8.6 Hz), 5.26(2H, s), 5.38(1H, d, J=4.0 Hz), 5.53(1H, dd, J=4.0 Hz, 7.9 Hz), 6.91-6.98 and 7.26-7.32(5H, m), 7.39-7.61(4H, 2d, J=8.6 Hz), 9.20(1H, d, J=7.9 Hz)

(b) 382 mg of a crude product of the compound (45) obtained in Reference Example 45 and 131 mg triphenylphosphine were dissolved in 5 ml dichloromethane. To this solution 1 ml of a solution of 131 mg 2,2'-dipyridyl sulfide in dichloromethane was added, then the resulting mixed solution was stirred at room temperature for 2 hours. The reaction mixture was concentrated under reduced pressure; the resulting residue was passed through a silica gel column and eluted with ethyl acetate-hexane (2:3). The eluted fraction containing the desired product was collected and concentrated under reduced pressure to yield isomers-A (20 mg) and -B (7 mg) of the subject compound, which were respectively identified as the isomer-A and isomer-B obtained in (a) by comparing NMR spectrum.

(c) 382 mg of a crude product of the compound (45) obtained in Reference Example 45 was dissolved in 4 ml dichloromethane. To this solution 40 $\mu$l thionyl chloride was added, while cooling the solution with ice, then the solution was stirred at the same temperature for 20 minutes. The reaction mixture was directly passed through a silica gel column and eluted with ethyl acetate-hexane (2:3), then the eluted fraction containing the desired product was collected and concentrated under reduced pressure to yield 13 mg of the isomer-A of the subject compound, which was identified as the isomer-A obtained in (a) above by comparing NMR spectrum.

EXAMPLE 13

Production of (4-bromo)benzyl (2S,6R,8R,9R)-4,10-dioxo-9-phenylacetamido-3-oxa-7-thia-1-azatricyclo[6,2,0,0$^{2,6}$]decane-2-carboxylate (Isomer-A) and (4-bromo)benzyl (2R,6S,8R,9R)-4,10-dioxo-9-phenylacetamido-3-oxa-7-thia-1-azatricyclo[6,2,0,0$^{2,6}$]-decane-2-carboxylate
(Isomer-B)

1.571 g of a crude product of the compound (46) as obtained in Reference Example 46 was dissolved in 20 ml dichloromethane. To this solution 730 mg 1-ethyl-3-[3-(dimethylamino)propyl]carbodiimide hydrochloride (hereinafter abbreviated as WSC) was added in a nitrogen gas flow, and the solution was stirred at room temperature for 2 hours. The reaction mixture, after adding 150 ml dichloromethane, was washed with a brine.

After drying (MgSO$_4$) the organic layer, the solvent was evaporated under reduced pressure. The resulting residue was passed through a silica gel column and eluted with ethyl acetate-hexane (1:1), then the fraction containing the desired product was collected and concentrated under reduced pressure to yield the isomer-A (white powder, 250 mg) and isomer-B (white powder, 215 mg) of the subject compound and a mixture of A and B (oily substance, 73 mg).

Isomer-A

FDMS m/z: 530 (M$^{30}$, $^{79}$Br), 532 (M$^{30}$, $^{81}$Br)

IR$\nu_{max}^{KBr}$ cm$^{-1}$: 3300, 3030, 1790, 1755, 1675, 1510, 1495, 1275, 1215, 1185, 1160, 1050

NMR (400 MHz, CDCl$_3$)$\delta$: 2.90(1H, dd, J=2.69 Hz, 18.8 Hz), 3.16(1H, dd, J=8.30 Hz, 18.8 Hz), 3.63(2H, ABq, J=16.1 Hz), 4.90(1H, dd, J=2.69 Hz, 8.3 Hz), 5.24(2H, ABq, J=12.0 Hz), 5.51(1H, d, J=4.40 Hz), 5.65(1H, dd, J=4.40 Hz, 9.04 Hz) 6.09(1H, d, J=9.04 Hz), 7.21–7.29 and 7.30–7.40(5H, m) 7.26 and 7.50 (4H, 2d, J=8.54 Hz)

Isomer-B

FDMS m/z: 530 (M$^+$, $^{79}$Br), 532 (M$^+$, $^{81}$Br)

IR$\nu_{max}^{KBr}$ cm$^{-1}$: 3300, 3025, 1810, 1750, 1670, 1530, 1490, 1270, 1210, 1180, 1115, 1070, 1010

NMR (400 MHz, CDCl$_3$)$\delta$: 2.58(1H, dd, J=2.93 Hz, 18.6 Hz), 3.05(1H, dd, J=8.30 Hz, 18.6 Hz), 3.62(2H, ABq, J=15.9 Hz), 4.52(1H, dd, J=2.93 Hz, 8.30 Hz), 5.21(2H, S), 5.34(1H, d, J=4.15 Hz), 5.55(1H, dd, J=4.15 Hz, 8.30 Hz), 6.21(1H, d, J=8.30 Hz), 7.18–7.27 and 7.29–7.39(5H, m), 7.22 and 7.52(4H, 2d, J=8.55 Hz)

EXAMPLE 14

Production of a mixture of diphenylmethyl (2S,6R,8R,9R)-4,10-dioxo-9-phenylacetamido-3-oxa-7-thia-1-azatricyclo[6,2,0,0$^{2,6}$]decane-2-carboxylate and diphenylmethyl (2R,6S,8R,9R)-4,10-dioxo-9-phenylacetamido-3-oxa-7-thia-1-azatricyclo[6,2,0,0$^{2,6}$]-decane-2-carboxylate 2.835 g of a crude product of the compound (48) as obtained in Reference Example 48 was dissolved in 40 ml dry dichloromethane. To this solution 1.150 g WSC was added in a nitrogen gas flow, and the solution was stirred at room temperature for 2.5 hours. The reaction mixture, after adding 200 ml dichloromethane, was washed with a brine. After drying (MgSO$_4$) the organic layer, the solvent was evaporated under reduced pressure. The resulting residue was passed through a silica gel column and eluted with ethyl acetate-hexane (9:11), then the fraction containing the desired product was collected and concentrated under reduced pressure to yield 740.5 mg of the subject compound in the form of a light yellow powder.

FDMS m/z: 528 (M$^+$)

IR$\nu_{max}^{KBr}$ cm$^{-1}$: 3300, 3025, 1790, 1750, 1670, 1495, 1270, 1210, 1180, 1045, 695

NMR (90 MHz, CDCl$_3$)$\delta$: 2.40–3.20(2H, m), 3.55(2H, S), 4.43 and 4.82(1H, 2dd, J=3 Hz, 8 Hz), 5.31–5.66(2H, m), 6.28 and 6.68(1H, 2d, J=9 Hz), 6.92(1H, S), 7.29–7.34(15H, m)

EXAMPLE 15

Production of a mixture of sodium (2S,6R,8R,9R)-4,10-dioxo-9-phenylacetamido-3-oxa-7-thia-1-azatricyclo[6,2,0,0$^{2,6}$]decane-2-carboxylate (Isomer-A) and sodium (2R,6S,8R,9R)-4,10-dioxo-9-phenylacetamido-3-oxa-7-thia-1-azatricyclo[6,2,0,0$^{2,6}$]decane-2-carboxylate (Isomer B)

214 mg of a mixture of 2 isomers as obtained in Example 14 was dissolved in a mixed solvent of 2 ml dry dichloromethane and 2 ml anisole. The resulting solution was cooled to $-50°$ C., then 81 mg anhydrous aluminum chloride was added in a nitrogen gas flow, and the solution was stirred for 45 minutes. The reaction mixture, after adding 10 ml of a 0.1M phosphate buffer solution of pH 7.0 containing 68 mg sodium bicarbonate, was filtered, and the resulting filtrate was washed with ethyl acetate. The water layer was taken, and the ethyl acetate was evaporated under reduced pressure, then the water layer was passed through an Amberlite XAD-2 column. The fraction eluted with water-ethanol (95:5) was collected and evaporated under reduced pressure to remove ethanol, after which it was lyophilized to yield 46 mg of the subject compound in the form of a white powder. This product was found to be a mixture of the isomer-A (substance identical with the compound obtained in Example 2) and the isomer-B in a 4:9 ratio. For the NMR data, only the signals assignable to the isomer-B are shown below.

SIMS m/z: 385 (MH$^+$)

IR$\nu_{max}^{KBr}$ cm$^{-1}$: 3420, 1790, 1780, 1650, 1530, 1385, 1290, 1195, 1040, 775

NMR (400 MHz, D$_2$O)$\delta$: 2.82(1H, dd, J=2.4 Hz, 19.1 Hz), 3.26(1H, dd, J=8.3 Hz, 19.1 Hz), 3.68(2H, ABq, J=14.9 Hz), 4.74(1H, dd, J=2.4 Hz, 8.3 Hz), 5.40(1H, d, J=3.9 Hz), 5.47(1H, d, J=3.9 Hz), 7.32–7.44(5H, m)

EXAMPLE 16

Production of a mixture of diphenylmethyl (2S,6R,8R,9R)-4,10-dioxo-9-phenoxyacetamido-3-oxa-7-thia-1-azatricyclo[6,2,0,0$^{2,6}$]decane-2-carboxylate and diphenylmethyl (2R,6S,8R,9R)-4,10-dioxo-9-phenoxyacetamido-3-oxa-7-thia-1-azatricyclo[6,2,0,0$^{2,6}$]decane-2-carboxylate 2.883 g of a crude product of the compound (49) as obtained in Reference Example 49 was dissolved in 40 ml dry dichloromethane. To the resulting solution 1.054 g WSC was added in a nitrogen gas flow, and the solution was stirred at room temperature for 2.5 hours. The reaction mixture, after adding 200 ml dichloromethane, was washed with a brine. After drying (MgSO$_4$) the organic layer, the solvent was evaporated under reduced pressure. The resulting residue was passed through a silica gel column and eluted with ethyl acetate-hexane (2:3), then the fraction containing the desired product was collected and concentrated under reduced pressure to yield 671 mg of the subject compound in the form of a light yellow powder and 297.5 mg of either isomer in the form of a white crystal.

Mixture of both isomers

IR$\nu_{max}^{KBr}$ cm$^{-1}$: 3425, 1825, 1815, 1790, 1765, 1690, 1520, 1500, 1440, 1240, 1205, 1125, 1060, 755

NMR (90 MHz, CDCl$_3$)$\delta$: 2.47–3.14(2H, m), 4.51(2H, S), 4.40–4.56 and 4.87–4.99(1H, m), 5.40(1H, d, J=4.0 Hz), 5.52–5.77(1H, m), 6.86–7.08 and 7.21–7.50(17H, m)

Single isomer (crystal)

Melting point: 181° to 184° C. (decomposed)

FDMS m/z: 544 (M$^+$)

IR$\nu_{max}^{KBr}$ cm$^{-1}$: 3420, 1810, 1795, 1750, 1705, 1520, 1500, 1295, 1265, 1225, 1180, 1050, 755

NMR (90 MHz, CDCl$_3$)$\delta$: 2.81(1H, dd, J=4 Hz, 18 Hz), 3.11(1H, dd, J=7.5 Hz, 18 Hz), 4.52(2H, S), 4.93(1H, dd, J=4 Hz, 7.5 Hz), 5.56(1H, d, J=4.5 Hz), 5,71(1H, dd, J=4.5 Hz, 9 Hz), 6.86–7.10 and 7.25–7.37(17H, m)

EXAMPLE 17

Production of a mixture of sodium (2S,6R,8R,9R)-4,10-dioxo-9-phenoxyacetamido-3-oxa-7-thia-1-azatricyclo[6,2,0,0$^{2,6}$]decane-2-carboxylate (Isomer-A) and sodium (2R,6S,8R,9R)-4,10-dioxo-9-phenoxyacetamido-3-oxa-7-thia-1-azatricyclo[6,2,0,0$^{2,6}$]decane-2-carboxylate (Isomer-B)

102 mg of a mixture of 2 isomers as obtained in Example 16 was dissolved in a mixed solvent of 1 ml dry dichloromethane and 1 ml anisole. The resulting solution was cooled to −50° C., 38 mg anhydrous aluminum chloride was added in a nitrogen gas flow, then the solution was stirred for 45 minutes. The reaction mixture, after adding 5 ml of a 0.1M phosphate buffer solution of pH 7.0 containing 31.5 mg sodium bicarbonate, was filtered; the resulting filtrate was washed with ethyl acetate. The water layer was taken and evaporated under reduced pressure to remove the ethyl acetate, after which it was passed through an Amberlite XAD-2 column. The fraction eluted with water-ethanol (95:5) was collected and evaporated to remove ethanol, after which it was lyophilized to yield 20 mg of the subject compound in the form of a white powder. This product was found to be a mixture of the isomer-A (substance identical with the compound obtained in Example 4) and the isomer-B in a 1:5 ratio. For the NMR data, only the signals assignable to the isomer-B were shown below.

SIMS m/z: 401 (MH+)

IR$\nu_{max}^{KBr}$ cm$^{-1}$: 3400, 1780, 1650, 1595, 1525, 1495, 1385, 1290, 1220, 755

NMR (270 MHz, d$_6$-DMSO)δ: 2.72(1H, dd, J=3.6 Hz, 18.5 Hz), 3.06(1H, dd, J=8.3 Hz, 18.5 Hz), 4.47(1H, dd, J=3.6 Hz, 8.3 Hz), 4.61(2H, ABq, J=15.0 Hz), 5.25(1H, d, J=4.0 Hz), 5.35(1H, dd, J=4.0 Hz, 7.9 Hz), 6.90-7.01 and 7.25-7.35(5H, m), 9.00(1H, d, J=7.9 Hz)

EXAMPLE 18

Production of (4-nitro) benzyl (2S,6R,8R,9R)-4,10-dioxo-9-phenylacetamido-3-oxa-7-thia-1-azatricyclo[6,2,0,0$^{2,6}$]decane-2-carboxylate (Isomer-A) and (4-nitro) benzyl (2R,6S,8R,9R)-4,10-dioxo-9-phenylacetamido-3-oxa-7-thia-1-azatricyclo[6,2,0,0$^{2,6}$]decane-2-carboxylate (Isomer-B)

6.552 g of a crude product of the compound (23) as obtained in Reference Example 23 was dissolved in 100 ml dry dichloromethane. To this solution 2.726 g WSC was added in a nitrogen gas flow, and the solution was stirred at room temperature for 1 hour and 50 minutes. The reaction mixture, after adding 600 ml dichloromethane, was washed with a brine. After drying (MgSO$_4$) the organic layer, the solvent was evaporated under reduced pressure. The resulting residue was passed through a silica gel column and eluted with ethyl acetate-hexane (1:1), then the fraction containing the desired product was collected and concentrated under reduced pressure to yield the isomer-A (substance identical with the compound obtained in Example 1, light yellow powder, 1.273 g) and isomer-B (pale yellow crystal, 887.5 mg) of the subject compound.

Isomer-A

[α]$_D^{22}$+157.6°(C=0.425, CHCl$_3$)

FDMS m/z: 497 (M+)

IR$\nu_{max}^{KBr}$ cm$^{-1}$: 3380, 3025, 1790, 1755, 1675, 1515, 1530, 1275, 1210, 1185, 1050

NMR (400 MHz, CDCl$_3$)δ: 2.93(1H, dd, J=2.69 Hz, 18.8 Hz), 3.18(1H, dd, J=8.54 Hz, 18.8 Hz), 3.64(2H, ABq, J=16.1 Hz), 4.94(1H, dd, J=2.69 Hz, 8,54 Hz), 5.39(2H, ABq, J=12.9 Hz), 5.53(1H, d, J=4.39 Hz), 5.66(1H, dd, J=4.39 Hz, 8.79 Hz), 6.09(1H, d, J=8.79 Hz), 7.22-7.29 and 7.30-7.41 (5H, m), 7.56 and 8.24(4H, 2d, J=8.79 Hz)

Isomer-B

Melting point: 160° to 163° C. (decomposed)

[α]$_D^{22}$+176.9°(C=0.45, CHCl$_3$)

FDMS m/z: 497 (M+)

IR$\nu_{max}^{KBr}$: 3380, 3025, 1810, 1765, 1675, 1525, 1350, 1275, 1215, 1115

NMR (400 MHz, CDCl$_3$)δ: 2.62(1H, dd, J=2.93 Hz, 18.6 Hz), 3.09(1H, dd, J=8.30 Hz, 18.6 Hz), 3.63(2H, ABq, J=15.9 Hz), 4.59(1H, dd, J=2.93 Hz, 8.30 Hz), 5.36(2H, ABq, J=12.9 Hz), 5.37(1H, d, J=4.15 Hz), 5.56(1H, dd, J=4.15 Hz, 8.05 Hz), 6.24(1H, d, J=8.05 Hz), 7.25-7.28 and 7.30-7.39(5H, m), 7.53 and 8.26(4H, 2d, J=8.79 Hz)

Elemental analysis (as C$_{23}$H$_{19}$N$_3$O$_8$S):

Calculated: C, 55.53; H, 3.85; N, 8.45

Found: C, 55.63; H, 3.93; N, 8.35

EXAMPLE 19

Production of sodium (2R,6S,8R,9R)-4,10-dioxo-9-phenylacetamido-3-oxa-7-thia-1-azatricyclo[6,2,0,0$^{2,6}$]decane-2-carboxylate 223 mg of the isomer-B obtained in Example 18 was dissolved in a mixed solvent of 8 ml ethyl acetate and 9.5 ml of a 0.1M phosphate buffer solution of pH 7.0. While cooling this solution with ice, 178 mg of 10% (W/W) palladium carbon was added, and hydrogen gas was passed while stirring the solution. 30 minutes, 1 hour and 15 minutes and 2 hours after initiation of reaction, 89 mg of 10% (W/W) palladium carbon was added respectively, and hydrogen gas was passed for in total 2.5 hours while cooling with ice and stirring the solution. The reaction mixture was filtered; the resulting filtrate was extracted with ethyl acetate. The water layer was taken and evaporated under reduced pressure to remove the ethyl acetate, after which it was passed through an Amberlite XAD-2 column. The fraction eluted with water-ethanol (95:5) was collected and evaporated under reduced pressure to remove ethanol, after which it was lyophilized to yield 94.5 mg of the subject compound in the form of a pale yellow powder.

Melting point: 130° to 134° C. (decomposed)

SIMS m/z: 385 (MH+)

IR$\nu_{max}^{KBr}$ cm$^{-1}$: 3420, 3025, 1790, 1655, 1535, 1500, 1390, 1290, 1220, 1200, 770

NMR (270 MHz, D$_2$O)δ: 2.80(1H, dd, J=2.64 Hz, 19.1 Hz), 3.28(1H, dd, J=8.25 Hz, 19.1 Hz), 3.70(2H, ABq, J=15.2 Hz), 4.74(1H, dd, J=2.64 Hz, 8.25 Hz), 5.39(1H, d, J=3.96 Hz), 5.49(1H, d, J=3.96 Hz), 7.34-7.45(5H, m)

EXAMPLE 20

Production of (4-nitro) benzyl (2S,6R,8R,9R)-4,10-dioxo-9-phenoxyacetamido-3-oxa-7-thia-1-azatricyclo[6,2,0,0$^{2,6}$]decane-2-carboxylate:

100 mg of the compound obtained in Example 1 was dissolved in 10 ml dry dichloromethane. While cooling to −78° C., the resulting solution, after adding 102 μl N,N-dimethylaniline and 84 mg powdered phosphorus pentachloride, was stirred for 1 hour and 20 minutes. 0.2 ml dry methanol was gradually added dropwise at −78° C. in a nitrogen gas flow over a period of 5 minutes. Then the solution was stirred for 2.5 hours while increasing temperature to −35° to −30° C. While cooling with ice, the solution, after adding 3 ml water, was stirred for 40 minutes, then a 5% aqueous solution of sodium bicarbonate was added to adjust the water layer to pH 7. The organic layer was taken and dried (MgSO$_4$), then the solvent was evaporated under reduced pressure. The resulting residue was suspended in 4 ml dry dichloromethane. While cooling with ice, the resulting suspension, after adding 34 μl triethylamine and 34 μl phenoxyacethylachloride, was stirred for 45 minutes. The reaction mixture, after adding 15 ml dichloromethane, was washed with 2N hydrochloric acid and then with a saturated sodium chloride solution. After drying (MgSO$_4$) the organic layer, the solvent was evaporated under reduced pressure. The resulting residue was passed through a silica gel column and eluted with ethyl acetate-hexane (9:11), then the fraction containing the desired product was collected and concentrated under reduced pressure to yield 35 mg of the subject compound in the form of a white powder. This product was identified as the compound obtained in Example 3 by comparison of NMR spectrum.

EXAMPLE 21

Production of (4-nitro) benzyl (2S,6R,8R,9R)-9-[2-(2-chloroacetamidothiazol-4-yl)-(Z)-2-methoxyiminoacetamido]-4,10-dioxo-3-oxa-7-thia-1-azatricyclo[6,2,0,0$^{2,6}$]decane-2-carboxylate:

100 mg of the compound obtained in Example 1 was dissolved in 10 ml dry dichloromethane. While cooling to −78° C., the resulting solution, after adding 102 μl N,N-dimethylaniline and 84 mg powdered phosphorus pentachloride, was stirred for 1 hour. 0.2 ml dry methanol was gradually added dropwise at −78° C. in a nitrogen gas flow over a period of 5 minutes. Then the solution was stirred for 2 hours and 40 minutes while increasing temperature to −35° to −30° C. While cooling with ice, the solution, after adding 2 ml water, was stirred for 30 minutes, then a 5% aqueous solution of sodium bicarbonate was added to adjust the water layer to pH 7. The organic layer was taken and dried (MgSO$_4$), after which it was concentrated under reduced pressure. While cooling with ice, the resulting concentrate, after adding 56 μl triethylamine and 67 mg 2-(2-chloroacetamidothiazol-4-yl)-(Z)-2-methoxyiminoacetyl chloride hydrochloride, was stirred for 1 hour. The reaction mixture, after adding 20 ml dichloromethane, was washed with 2N hydrochloric acid and then with a saturated sodium chloride solution. After drying (MgSO$_4$) the organic layer, the solvent was evaporated under reduced pressure. The resulting residue was passed through a silica gel column and eluted with ethyl acetate-hexane (2:1), then the fraction containing the desired product was collected and concentrated under reduced pressure to yield 83 mg of the subject compound in the form of a light yellow powder.

IRν$_{max}^{KBr}$ cm$^{-1}$: 3300, 2945, 1795, 1760, 1690, 1605, 1550, 1525, 1350, 1270, 1215, 1185, 1155, 1110, 1040, 850

NMR (90 MHz, CDCl$_3$) δ: 2.93(1H, dd, J=4 Hz, 18 Hz), 3.25(1H, dd, J=8 Hz, 18 Hz), 4.07 (3H, S), 4.27(2H, S), 5.05(1H, dd, J=4 Hz, 8 Hz), 5.40(2H, Abq, J=12 Hz), 5.68(1H, d, J=4 Hz), 5.81(1H, dd, J=4 Hz, 9 Hz), 7.25(1H, d, J=9 Hz), 7.41(1H, S), 7.56 and 8.22(4H, 2d, J=9 Hz), 9.99(1H, br)

EXAMPLE 22

Production of (4-nitro) benzyl (2S,6R,8r,9R)-9-[2-(2-aminothiazol-4-yl)-(Z)-2-methoxyiminoacetamido]-4,10-dioxo-3-oxa-7-thia-1-azatricyclo[6,2,0,0$^{2,6}$]decane-2-carboxylate:

(a) 100 mg of the compound obtained in Example 1 was dissolved in 10 ml dry dichloromethane. While cooling to −78° C., the resulting solution, after adding 102 μl, N,N-dimethylaniline and 84 mg powdered phosphorus pentachloride, was stirred for 1 hour. 0.2 ml dry methanol was gradually added dropwise at −78° C. in a nitrogen gas flow over a period of 5 minutes. Then the solution was stirred for 2 hours and 45 minutes while increasing temperature to −35° to −30° C. While cooling with ice, the solution, after adding 2 ml water, was stirred for 30 minutes, then a 5% aqueous solution of sodium bicarbonate was added to adjust the water layer to a pH of about 6.5. The organic layer was taken and dried (MgSO$_4$), after which it was concentrated under reduced pressure. While cooling the resulting concentrate with ice, 3 ml of a solution in dry tetrahydrofuran of 74 mg of the active ester S-(benzothiazol-2-yl)2-(2-aminothiazol-4-yl)-(Z)-2-methoxyiminoethanethioate synthesized by the method described in Japanese published unexamined patent application No. 84293/1985 was added, and the resulting mixed solution was stirred at room temperature for 3 hours. The reaction mixture was concentrated under reduced pressure; the resulting residue was passed through a silica gel column and eluted with ethyl acetate-chloroform-methanol (10:10:1). The fraction containing the desired product was then collected and concentrated under reduced pressure to yield 53 mg of the subject compound in the form of a white powder. [α]$_D^{23}$ +147.9°(C=0.48, Ethylacetate) SIMS m/z: 563 (MH+)

IRν$_{max}^{KBr}$ cm$^{-1}$: 3350, 2960, 1795, 1760, 1680, 1605, 1525, 1350, 1270, 1215, 1185, 1045, 850

NMR (400 MHz, d$_6$-DMSO)δ: 3.04(1H, dd, J=5.62 Hz, 18.56 Hz), 3.25(1H, dd, J=9.28 Hz, 18.56 Hz), 3.83(3H, S), 5.04(1H, dd, J=5.62 Hz, 9.28 Hz), 5.40(2H, ABq, J=13.68 Hz), 5.63(1H, dd, J=4.39 Hz, 7.57 Hz), 5.80(1H, d, J=4.39 Hz), 6.76(1H, S), 7.21(2H, S), 7.72 and 8.24(4H, 2d, J=8.79 Hz), 9.68(1H, d, J=7.57 Hz)

(b) 24.5 mg of the compound obtained in Examle 21 was dissolved in a mixed solvent of 0.6 ml of N,N-dimethylformamide and 0.3 ml of a 0.1M phosphate buffer solution of pH 7.0. While cooling the resulting solution with ice, 5.5 mg sodium N-methyldithiocarbamate was added, and the solution was stirred for 1 hour and 40 minutes while cooling with ice and for 1 hour at room temperature. The reaction mixture, after adding 20 ml of ethyl acetate, was washed with water, and the organic layer was dried (MgSO$_4$), then the solvent was evaporated under reduced pressure. The resulting residue was passed through a silica gel column and eluted with ethyl acetate-chloroform-methanol (10:10:1), then the fraction containing the desired product was collected and concentrated under reduced pressure to yield 10.5 mg of the subject compound in the form of a white powder. This product was identified with the compound obtained in (a) by comparison of NMR spectrum.

EXAMPLE 23

Production of sodium (2S,6R,8R,9R)-9-[2-(2-aminothiazol-4-yl)-(Z)-2-methoxyiminoacetamido]-4,10-dioxo-3-oxa-7-thia-1-azatricyclo[6,2,0,0$^{2,6}$]-decane-2-carboxylate:

100 mg of the compound obtained in Example 22 was dissolved in a mixed solvent of 3 ml ethyl acetate and 4 ml of a 0.1M phosphate buffer solution of pH 7.0. While cooling the resulting solution with ice, 71 mg of 10% (W/W) palladium carbon was added, and hydrogen gas was passed while stirring the solution. 30 minutes, 1 hour and 15 minutes, 2 hours, 2 hours and 55 minutes and 3 hours and 50 minutes after the initiation of reaction, 35 mg of 10% (W/W) palladium carbon was added respectively, and hydrogen gas was passed through the solution for 4.5 hours while cooling the solution with ice and for 45 minutes at 10° to 13° C. (5 hours and 15 minutes in total). The reacted liquid was filtered, and the resulting filtrate was extracted with ethyl acetate. The water layer was taken and evaporated under reduced pressure to remove the ethyl acetate, after which it was passed through an Amberlite XAD-2 column. The fraction eluted with water-ethanol (95:5) was collected and evaporated under reduced pressure to remove ethanol, after which it was lyophilized to yield 45.5 mg of the subject compound in the form of a white powder.

Melting point: 187° to 191° C.(decomposed)

SIMS m/z: 450 (MH+)

IR$v_{max}^{KBr}$ cm$^{-1}$: 3350, 1780, 1660, 1650, 1530, 1380, 1290, 1190, 1030

NMR (400 MHz, D$_2$O)δ: 3.07(1H, dd, J=4.64 Hz, 19.29 Hz), 3.37(1H, dd, J=9.28 Hz, 19.29 Hz), 4.00(3H, S), 4.96(1H, dd, J=4.64 Hz, 9.28 Hz), 5.67(1H, d, J=4.15 Hz), 5.79(1H, d, J=4.15 Hz), 7.06(1H, S)

EXAMPLE 24

Production of (4-nitro) benzyl (2R,6S,8R,9R)-9-[2-(2-chloroacetamidothiazol-4-yl)-(Z)-2-methoxyiminoacetamido]-4,10-dioxo-3-oxa-7-thia-1-azatricyclo[6,2,0,0$^{2,6}$]decane-2-carboxylate:

150 mg of the isomer-B obtained in Example 18 was dissolved in 15 ml drydichloromethane. While cooling to −78° C., the resulting solution, after adding 153 μl N,N-dimethylaniline and 126 mg powdered phosphorus pentachloride, was stirred for 1 hour. 0.3 ml dry methanol was gradually added dropwise at −78° C. in a nitrogen gas flow over a period of 5 minutes. Then the solution was stirred for 2 hours and 45 minutes while incresing temperature to −35° to −30° C. While cooling with ice, the solution, after adding 3 ml water, was stirred for 30 minutes, then a 5% aqueous solution of sodium bicarbonate was added to adjust the water layer to pH 7. The organic layer was taken and dried (MgSO$_4$), after which it can concentrated under reduced pressure. While cooling with ice, the resulting concentrate, after adding 84 μl triethylamine and 100 mg 2-(2-chloroacetamido-thiazol-4-yl)-(Z)-2-methoxyiminoacetyl chloride hydrochloride, was stirred for 1 hour. The reaction mixture, after adding 25 ml dichloromethane, was washed with 2N hydrochloric acid and then with a saturated sodium chloride solution. After drying (MgSO$_4$) the organic layer, the solvent was evaporated under reduced pressure. The resulting residue was passed through a silica gel column and eluted with ethyl acetate-hexane (7:3), then the fraction containing the desired product was collected and concentrated under reduced pressure to yield 116 mg of the subject compound in the form of a light yellow powder.

IR$v_{max}^{KBr}$ cm$^{-1}$: 3280, 2940, 1810, 1760, 1690, 1605, 1550, 1530, 1345, 1315, 1270, 1210, 1180, 1110, 1040

NMR (90 MHz, CDCl$_3$)δ: 2.73(1H, dd, J=4 Hz, 18 Hz), 3.15(1H, dd, J=8 Hz, 18 Hz), 4.03(3H, S), 4.27(2H, S), 4.66(1H, dd, J=4 Hz, 8 Hz), 5.39(2H, S), 5.51(1H, d, J=4 Hz), 5.78(1H, dd, J=4 Hz, 9 Hz), 7.33(1H, S), 7.76(1H, d, J=9 Hz), 7.56 and 8.27(4H, 2d, J=9 Hz), 10.13(1H, br)

EXAMPLE 25

Production of (4-nitro) benzyl (2R,6S,8R,9R)-9-[2-(2-aminothiazol-4-yl)-(Z)-2-methoxyiminoacetamido]-4,10-dioxo-3-oxa-7-thia-1-azatricyclo[6,2,0,0$^{2,6}$]decane-2-carboxylate:

409 mg of the isomer-B obtained in Example 18 was dissolved in 40 ml dry dichloromethane. While cooling to −78° C., the resulting solution, after adding 417 μl N,N-dimethylaniline and 342 mg powdered phosphorus pentachloride, was stirred for 1 hour. 0.8 ml dry methanol was gradually added dropwise at −78° C. in a nitrogen gas flow over a period of 5 minutes. Then the solution was stirred for 2 hours and 55 minutes while increasing temperature to −35° to −30° C. While cooling with ice, the solution, after adding 8 ml water, was stirred for 30 minutes, then a 5% aqueous solution of sodium bicarbonate was added to adjust the water layer to a pH of about 6.5. The organic layer was taken and dried (MgSO$_4$), after which it was concentrated under reduced pressure. While cooling the resulting concentrate with ice, 10 ml of a solution in dry tetrahydrofuran of 303 mg of the active ester S-(benzothiazol-4-yl) 2-(2-aminothiazol-4-yl)-(Z)-2-methoxyiminoethanethioate synthesized by the method described in Japanese published unexamined patent application No. 84293/1985 was added, and the resulting solution was stirred at room temperature for 2.5 hours. The reaction mixture was concentrated under reduced pressure. The resulting residue was passed through a silica gel column and eluted with ethyl acetate-hexane (9:1), then the fraction containing the desired product was collected and concentrated under reduced pressure to yield 180 mg of the subject compound in the form of a pale yellow powder.

[α]$_D^{23}$+143.1°(C=0.174, Ethylacetate)

SIMS m/z: 563 (MH+)

IR$v_{max}^{KBr}$ cm$^{-1}$: 3350, 2960, 2855, 1805, 1760, 1675, 1600, 1520, 1350, 1270, 1210, 1180, 1115, 1030, 845

NMR (400 MHz, d$_6$-DMSO)δ: 3.07(1H, dd, J=4.39 Hz, 18.80 Hz), 3.26(1H, dd, J=8.54 Hz, 18.80 Hz), 3.84(3H, S), 4.94(1H, dd, J=4.39 Hz, 8.54 Hz), 5.44(2H, S), 5.46(1H, d, J=4.15 Hz), 5.67(1H, dd, J=4.15 Hz, 8.30 Hz), 6.77(1H, S), 7.23(2H, br), 7.71 and 8.28(4H, 2d, J=8.79 Hz), 9.73(1H, d, J=8.30 Hz)

EXAMPLE 26

Production of sodium (2R,6S,8R,9R)-9-[2-(2-aminothiazol-4-yl)-(Z)-2-methoxyiminoacetamido]-4,10-dioxo-3-oxa-7-thia-1-azatricyclo[6,2,0,0$^{2,6}$]decane-2-carboxylate:

100 mg of the compound obtained in Example 25 was dissolved in a mixed solvent of 5 ethyl acetate and 7 ml of a 0.1M phosphate buffer solution of pH 7.0. To the resulting solution 71 mg of 10% (W/W) palladium carbon was added at 10° to 12° C., the hydrogen gas was passed through the solution while stirring the solution. 30 minutes, 1 hour, 1.5 hours and 2 hours and 15 minutes after the initiation of reaction, 35 mg of 10% palladium carbon was added respectively, and hydrogen gas was passed through the solution at 10° to 12° C. for in total 3 hours while stirring the solution. The reaction mixture was filtered; the resulting filtrate was extracted with ethyl acetate. The water layer was taken and evaporated under reduced pressure to remove ethyl acetate, after which it was passed through an Amberlite XAD-2 column. The fraction eluted with water-ethanol (95:5) was collected and evaporated under reduced pressure to remove ethanol, after which it was lyophilized to yield 52 mg of the subject compound in the form of a white powder.

Melting point: 190° to 183° C.(decomposed)
SIMS m/z: 450 (MH+)
IRv$_{max}^{KBr}$ cm$^{-1}$: 3430, 1785, 1645, 1535, 1380, 1290, 1220, 1195, 1040
NMR (400 MHz, D$_2$O)δ: 2.88(1H, dd, J=2.68 Hz, 19.04 Hz), 3.29(1H, dd, J=8.30 Hz, 19.04 Hz), 3.99(3H, S), 4.85(1H, dd, J=2.68 Hz, 8.30 Hz), 5.60(2H, S), 7.03(1H, S)

What we claim is:
1. A compound of the formula:

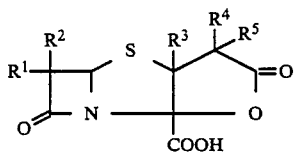

wherein R$^1$ represents hydrogen, an amino group, an acylamino group wherein the acyl moiety is derived from a carboxylic acid, or an alkyl which may be substituted by a hydroxy group; R$^2$ represents hydrogen, a methoxy group or a formylamino group and R$^3$, R$^4$ and R$^5$ independently represent hydrogen or an alkyl, its ester or its salt.

2. A compound as claimed in claim 1, which is (2S,6R,8R,9R)-4,10-dioxo-9-phenylacetamido-3-oxa-7-thia-1-azatricyclo[6,2,0,0$^{2,6}$]decane-2-carboxylic acid, its ester or its salt.

3. A compound as claimed in claim 1, which is (2S,6R,8R,9R)-4,10-dioxo-9-phenoxyacetamido-3-oxa-7-thia-1-azatricyclo[6,2,0,0$^{2,6}$]decane-2-carboxylic acid, its ester or its salt.

4. A compound as claimed in claim 1, which is (2S,6R,8R,9R)-4,10-dioxo-9-[(2R)-2-(4-ethyl-2,3-dioxo-1piperazinecarboxamide)phenylacetamido-3-oxa-7-thia-1-azatricyclo[6,2,0,0$^{2,6}$]decane-2-carboxylic acid, its ester or its salt.

5. A compound as claimed in claim 1, which is 4,10-dioxo-3-oxa-7-thia-1-azatricyclo[6,2,0,0$^{2,6}$]decane-2-carboxylic acid, its ester or its salt.

6. A compound as claimed in claim 1, which is (8R,9S)-4,10-dioxo-9-[(1R)-1-hydroxy]ethyl-3-oxa-7-thia-1-azatricyclo[6,2,0,0$^{2,6}$]decane-2-carboxylic acid, its ester, or its salt.

7. A compound as claimed in claim 1, which is (2S,6R,8R,9R)-9[2-(2-chloroacetamido-thiazol-4-yl)-(Z)-2-methoxyiminoacetamido]-4,10-dioxo-3-oxa-7-thia-1-azatricyclo[6,2,0,0$^{2,6}$]decane-2-carboxylic acid, its ester, or its salt.

8. A compound as claimed in claim 1, which is (aS,6R,8R,9R)-9[2-(2-aminothiazol-4-yl)-(Z)-2-methoxyiminoacetamido]-4,10-dioxo-3-oxa-7-thia-1-azatricyclo[6,2,0,0$^{2,6}$]decane-2-carboxylic acid, its ester or its salt.

9. A compound as claimed in claim 1, which is (2R,6S,8R,9R)-4,10-dioxo-9-phenylacetamido-3-oxa-7-thia-1-azatricyclo[6,2,0,0$^{2,6}$]decane-2-carboxylic acid, its ester or its salt.

10. A compound as claimed in claim 1, which is (2R,6S,8R,9R)-4,10-dioxo-9-phenoxyacetamido-3-oxa-7-thia-1-azatricyclo[6,2,0,0$^{2,6}$]decane-2-carboxylic acid, its ester or its salt.

11. A compound as claimed in claim 1, which is (2R,6S,8R,9R)-4,10-dioxo-9-[(2R)-2-(4-ethyl-2,3-dioxo-1-piperazinecarboxamide)phenylacetamido-3-oxa-7-thia-1-azatricyclo[6,2,0,0$^{2,6}$]decane-2-carboxylic acid, its ester or its salt.

12. A compound as claimed in claim 1, which is (2R,6S,8R,9R)-9[2-(2-chloroacetamido-thiazol-4-yl)-(Z)-2-methoxyiminoacetamido]-4,10-dioxo-3-oxa-7-thia-1-azatricyclo[6,2,0,0$^{2,6}$]decane-2-carboxylic acid, its ester, or its salt.

13. A compound as claimed in claim 1, which is (2R,6S,8R,9R)-9[2-(2-aminothiazol-4-yl)-(Z)-2-methoxyiminoacetamido]-4,10-dioxo-3-oxa-7-thia-1-azatricyclo[6,2,0,$^{2,6}$]decane-2-carboxylic acid, its ester or its salt.

14. A compound as claimed in claim 1, wherein R$^1$ is an alkyl group of one to six carbon atoms and R$^3$, R$^4$ and R$^5$ independently represent hydrogen or an alkyl group of one to six carbon atoms.

15. A compound as claimed in claim 1, wherein R$^1$ is an acylamino group in which the acyl moiety is derived from a carboxylic acid of one to six carbon atoms and R$^3$, R$^4$ and R$_5$ independently represent hydrogen or an alkyl group of one to six carbon atoms.

16. A method for producing a compound of the formula

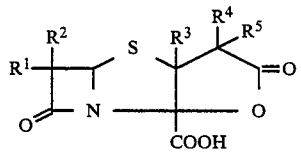

wherein R$^1$ represents hydrogen, an amino group, an acylamino group wherein the acyl moiety is derived from a carboxylic acid, or an alkyl which may be substituted by hydroxy group; R$^2$ represents hydrogen, a methoxy group or a formylamino group and R$^3$, R$^4$ and R$^5$ independently represent hydrogen or an alkyl, its ester or its salt, characterized by the cyclization of a compound of the formula

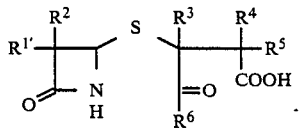

(II)

wherein R$^6$ represents a group derivable from a carboxyl group and R$^1$, R$^2$, R$^3$, R$^4$ and R$^5$ are defined as above or a compound of the formula

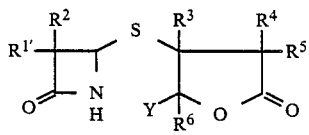

(III)

wherein Y represents a leaving group and; R$^1$, R$^2$, R$^3$, R$^4$, R$^5$ and R$^6$ are defined as above.

17. A compound of the formula

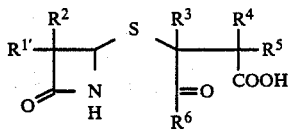

wherein $R^1$ represents hydrogen, an amino group, an acylamino group, wherein the acyl moiety is derived from a carboxylic acid, or an alkyl which may be substituted by hydroxy group; $R^2$ represents hydrogen, a methoxy group or a formylamino group and $R^3$, $R^4$ and $R^5$ independently represent hydrogen or an alkyl and $R^6$ represents a group derivable from the carboxyl group, its ester of its salt.

18. A compound of the formula

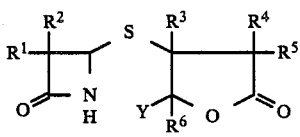

wherein Y represents a leaving group;
$R^1$ represents hydrogen, an amino group, an acylamino group wherein the acyl moeity is derived from a carboxylic acid, or an alkyl which may be substituted by hydroxy group; $R^2$ represents hydrogen, a methoxy group or a formylamino group and $R^3$, $R^4$ and $R^5$ independently represent hydrogen or an alkyl, $R^6$ represents a group derivable from the carboxyl group, its ester or its salt.

19. An antibacterial composition containing an antibacterially effective amount of a compound of the formula

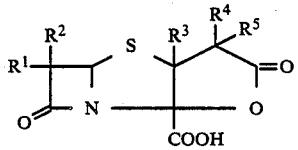

wherein $R^1$ represents hydrogen, an amino group, an acylamino group wherein the acyl moiety is derived from a carboxylic acid, or an alkyl which may be substituted by hydroxy group; $R^2$ represents hydrogen, a methoxy group or a formylamino group and $R^3$, $R^4$ and $R^5$ independently represent hydrogen or an alkyl, its ester or its salt and a carrier.

* * * * *